United States Patent
Shelton, IV et al.

(10) Patent No.: US 11,589,731 B2
(45) Date of Patent: *Feb. 28, 2023

(54) VISUALIZATION SYSTEMS USING STRUCTURED LIGHT

(71) Applicant: Ethicon LLC, Guaynabo, PR (US)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/215,235

(22) Filed: Mar. 29, 2021

(65) Prior Publication Data

US 2021/0212794 A1 Jul. 15, 2021

Related U.S. Application Data

(63) Continuation of application No. 16/729,737, filed on Dec. 30, 2019, and a continuation of application No.
(Continued)

(51) Int. Cl.
*A61B 90/30* (2016.01)
*A61B 1/00* (2006.01)
(Continued)

(52) U.S. Cl.
CPC ........ *A61B 1/000094* (2022.02); *A61B 1/009* (2022.02); *A61B 1/00194* (2022.02);
(Continued)

(58) Field of Classification Search
CPC ... A61B 90/37; A61B 90/30; A61B 2090/367; G06T 17/00; G06T 2210/41
See application file for complete search history.

(56) References Cited

U.S. PATENT DOCUMENTS

| 4,753,641 A | 6/1988 | Vaslow |
| 4,785,180 A | 11/1988 | Dietrich et al. |

(Continued)

FOREIGN PATENT DOCUMENTS

| CN | 109011149 A | 12/2018 |
| DE | 102015115903 A1 | 3/2017 |

(Continued)

OTHER PUBLICATIONS

Kurata et al. "Time-of-flight Near-infrared Spectroscopy for Non-destructive Measurement of Internal Quality in Grapefruit," J. Amer. Soc. Hort. Sci. 138(3): 225-228, 2013.
(Continued)

*Primary Examiner* — Said Broome

(57) ABSTRACT

A visualization system including multiple light sources, an image sensor configured to detect imaging data from the multiple light sources, and a control circuit is disclosed. At least one of the light sources is configured to emit a pattern of structured light. The control circuit is configured to receive the imaging data from the image sensor, generate a three-dimensional digital representation of the anatomical structure from the pattern of structured light detected by the imaging data, obtain metadata from the imaging data, overlay the metadata on the three-dimensional digital representation, receive updated imaging data from the image sensor, and generate an updated three-dimensional digital representation of the anatomical structure based on the updated imaging data. The visualization system can be communicatively coupled to a situational awareness module configured to determine a surgical scenario based on input signals from multiple surgical devices.

24 Claims, 41 Drawing Sheets

Related U.S. Application Data

16/729,778, filed on Dec. 30, 2019, and a continuation of application No. 16/729,744, filed on Dec. 30, 2019, now Pat. No. 11,219,501.

(51) Int. Cl.

| | | |
|---|---|---|
| *A61B 90/00* | (2016.01) | |
| *G06T 7/521* | (2017.01) | |
| *G06T 17/00* | (2006.01) | |
| *A61B 1/005* | (2006.01) | |
| *A61B 1/04* | (2006.01) | |
| *A61B 1/06* | (2006.01) | |
| *A61B 34/30* | (2016.01) | |

(52) U.S. Cl.
CPC ............ *A61B 1/046* (2022.02); *A61B 1/0605* (2022.02); *A61B 90/30* (2016.02); *A61B 90/37* (2016.02); *G06T 7/521* (2017.01); *G06T 17/00* (2013.01); *A61B 34/30* (2016.02); *A61B 2090/367* (2016.02); *A61B 2090/371* (2016.02); *A61B 2090/373* (2016.02); *G06T 2210/41* (2013.01)

(56) References Cited

U.S. PATENT DOCUMENTS

| | | |
|---|---|---|
| 4,986,262 A | 1/1991 | Saito |
| 5,460,182 A | 10/1995 | Goodman et al. |
| 5,609,562 A | 3/1997 | Kaali |
| 6,350,233 B1 | 2/2002 | Lubowski |
| 6,386,758 B2 | 5/2002 | Loser |
| 6,632,183 B2 | 10/2003 | Bowman et al. |
| 6,804,012 B2 | 10/2004 | Gombert |
| 6,869,430 B2 | 3/2005 | Balbierz et al. |
| 6,951,535 B2 | 10/2005 | Ghodoussi et al. |
| 7,314,048 B2 | 1/2008 | Couture et al. |
| 7,477,931 B2 | 1/2009 | Hoyt |
| 7,516,675 B2 | 4/2009 | Kurtz et al. |
| 7,726,171 B2 | 6/2010 | Langlotz et al. |
| 7,740,623 B2 | 6/2010 | Nayak et al. |
| 7,766,210 B2 | 8/2010 | Shelton, IV et al. |
| 7,770,775 B2 | 8/2010 | Shelton, IV et al. |
| 7,798,385 B2 | 9/2010 | Boyden et al. |
| 7,810,691 B2 | 10/2010 | Boyden et al. |
| 7,901,353 B2 | 3/2011 | Vayser et al. |
| 7,905,840 B2 | 3/2011 | Pimenta et al. |
| 7,975,894 B2 | 7/2011 | Boyden et al. |
| 8,041,089 B2 | 10/2011 | Drumm et al. |
| 8,063,883 B2 | 11/2011 | Senft et al. |
| 8,073,528 B2 | 12/2011 | Zhao et al. |
| 8,079,950 B2 | 12/2011 | Stern et al. |
| 8,142,450 B2 | 3/2012 | Harris et al. |
| 8,161,977 B2 | 4/2012 | Shelton, IV et al. |
| 8,224,484 B2 | 7/2012 | Swarup et al. |
| 8,231,639 B2 | 7/2012 | Bolduc et al. |
| 8,523,043 B2 | 9/2013 | Ullrich et al. |
| 8,632,468 B2 | 1/2014 | Glossop et al. |
| 8,652,148 B2 | 2/2014 | Zuhars |
| 8,706,211 B2 | 4/2014 | Dacey, Jr. et al. |
| 8,755,576 B2 | 6/2014 | Taerum |
| 8,763,879 B2 | 7/2014 | Shelton, IV et al. |
| 8,820,603 B2 | 9/2014 | Shelton, IV et al. |
| 8,840,616 B2 | 9/2014 | Wilkinson et al. |
| 8,932,208 B2 | 1/2015 | Kendale et al. |
| 8,934,003 B2 | 1/2015 | Popovic et al. |
| 8,989,528 B2 | 3/2015 | Udd |
| 8,992,558 B2 | 3/2015 | Stone et al. |
| 9,005,118 B2 | 4/2015 | Selover et al. |
| 9,044,230 B2 | 6/2015 | Morgan et al. |
| 9,064,173 B2 | 6/2015 | Redden |
| 9,072,501 B2 | 7/2015 | Menchaca et al. |
| 9,072,535 B2 | 7/2015 | Shelton, IV et al. |
| 9,119,670 B2 | 9/2015 | Yang et al. |
| 9,141,868 B2 | 9/2015 | Xu et al. |
| 9,161,817 B2 | 10/2015 | Olson et al. |
| 9,161,820 B2 | 10/2015 | Mark et al. |
| 9,179,822 B2 | 11/2015 | Kitamura et al. |
| 9,241,693 B2 | 1/2016 | Taylor et al. |
| 9,254,103 B2 | 2/2016 | Krishnaswamy et al. |
| 9,259,290 B2 | 2/2016 | Jenkins et al. |
| 9,265,587 B2 | 2/2016 | Vancamberg et al. |
| 9,274,047 B2 | 3/2016 | Velten et al. |
| 9,282,878 B2 | 3/2016 | Grey et al. |
| 9,295,773 B2 | 3/2016 | Prosl et al. |
| 9,326,770 B2 | 5/2016 | Shelton, IV et al. |
| 9,345,389 B2 | 5/2016 | Nie et al. |
| 9,402,726 B2 | 8/2016 | Linderman et al. |
| 9,480,534 B2 | 11/2016 | Bowling et al. |
| 9,561,019 B2 | 2/2017 | Mihailescu et al. |
| 9,561,082 B2 | 2/2017 | Yen et al. |
| 9,597,054 B2 | 3/2017 | Kudavelly et al. |
| 9,649,109 B2 | 5/2017 | Ranucci et al. |
| 9,720,076 B2 | 8/2017 | Guo et al. |
| 9,730,690 B2 | 8/2017 | Shanley et al. |
| 9,788,851 B2 | 10/2017 | Dannaher et al. |
| 9,801,685 B2 | 10/2017 | Nguyen et al. |
| 9,855,317 B2 | 1/2018 | Bright |
| 9,857,167 B2 | 1/2018 | Jovanovski et al. |
| 9,883,857 B2 | 2/2018 | Shluzas et al. |
| 9,901,409 B2 | 2/2018 | Yang et al. |
| 9,918,640 B2 | 3/2018 | Ntziachristos et al. |
| 9,987,019 B2 | 6/2018 | Sato |
| 10,010,326 B2 | 7/2018 | Sato |
| 10,022,199 B2 | 7/2018 | Gassner et al. |
| 10,045,763 B2 | 8/2018 | Sato |
| 10,068,173 B2 | 9/2018 | Vayser et al. |
| 10,070,929 B2 | 9/2018 | Tanji |
| 10,085,611 B2 | 10/2018 | Yabe et al. |
| 10,123,706 B2 | 11/2018 | Elbaz et al. |
| 10,136,959 B2 | 11/2018 | Mintz et al. |
| 10,143,470 B2 | 12/2018 | Sato |
| 10,170,205 B2 | 1/2019 | Curd et al. |
| 10,194,981 B2 | 2/2019 | Margallo Balbas et al. |
| 10,194,990 B2 | 2/2019 | Amanatullah et al. |
| 10,219,738 B2 | 3/2019 | Monty et al. |
| 10,255,723 B2 | 4/2019 | Thomas et al. |
| 10,314,463 B2 | 6/2019 | Agrawal et al. |
| 10,357,253 B2 | 7/2019 | Sato |
| 10,390,835 B2 | 8/2019 | Williams |
| 10,433,911 B2 | 10/2019 | Wang et al. |
| 10,470,763 B2 | 11/2019 | Yates et al. |
| 10,506,991 B2 | 12/2019 | Govari |
| 10,510,149 B2 | 12/2019 | Cutu et al. |
| 10,512,518 B2 | 12/2019 | Vayser et al. |
| 10,531,074 B2 | 1/2020 | Wilson et al. |
| 10,546,423 B2 * | 1/2020 | Jones .................... G06F 3/0346 |
| 10,548,679 B2 | 2/2020 | Carlson et al. |
| 10,561,465 B2 | 2/2020 | Scholl et al. |
| 10,576,246 B2 | 3/2020 | Fischell et al. |
| 10,588,699 B2 | 3/2020 | Richmond et al. |
| 10,666,928 B2 | 5/2020 | Liu |
| 10,687,797 B2 | 6/2020 | Stone et al. |
| 10,695,166 B2 | 6/2020 | Willis et al. |
| 10,702,186 B2 | 7/2020 | Amies et al. |
| 10,704,093 B2 | 7/2020 | Deng et al. |
| 10,743,868 B2 | 8/2020 | Shelton, IV et al. |
| 10,792,034 B2 | 10/2020 | Scheib et al. |
| 10,806,518 B2 | 10/2020 | Amanatullah |
| 10,813,700 B2 | 10/2020 | Amanatullah |
| 10,861,197 B2 | 12/2020 | Kobayashi |
| 10,866,783 B2 | 12/2020 | Atarot et al. |
| 10,881,458 B2 | 1/2021 | Fischell et al. |
| 10,898,064 B2 | 1/2021 | Atarot et al. |
| 10,925,598 B2 | 2/2021 | Scheib et al. |
| 10,945,787 B2 | 3/2021 | Fischell et al. |
| 10,945,796 B2 | 3/2021 | Popovic et al. |
| 10,973,519 B2 | 4/2021 | Weir et al. |
| 10,980,420 B2 | 4/2021 | Fengler et al. |
| 10,986,999 B2 | 4/2021 | Frangioni et al. |
| 11,000,270 B2 | 5/2021 | Scheib et al. |
| 11,006,100 B1 | 5/2021 | Douglas |
| 11,013,563 B2 | 5/2021 | Shelton, IV et al. |
| 11,020,016 B2 | 6/2021 | Wallace et al. |

(56) References Cited

U.S. PATENT DOCUMENTS

| | | |
|---|---|---|
| 11,058,501 B2 | 7/2021 | Tokarchuk et al. |
| 11,100,631 B2 | 8/2021 | Yates et al. |
| 11,298,128 B2 | 4/2022 | Messerly et al. |
| 2001/0012327 A1 | 8/2001 | Loser |
| 2003/0069591 A1 | 4/2003 | Carson et al. |
| 2004/0082842 A1 | 4/2004 | Lumba et al. |
| 2004/0106916 A1 | 6/2004 | Quaid et al. |
| 2004/0147926 A1 | 7/2004 | Iversen |
| 2004/0176751 A1 | 9/2004 | Weitzner et al. |
| 2004/0230199 A1 | 11/2004 | Jansen et al. |
| 2005/0113846 A1 | 5/2005 | Carson |
| 2005/0124975 A1 | 6/2005 | Law |
| 2005/0167621 A1 | 8/2005 | Zeng et al. |
| 2005/0177181 A1 | 8/2005 | Kagan et al. |
| 2005/0279354 A1 | 12/2005 | Deutsch et al. |
| 2006/0013454 A1 | 1/2006 | Flewelling et al. |
| 2006/0079841 A1 | 4/2006 | Duff et al. |
| 2006/0206007 A1 | 9/2006 | Bala |
| 2006/0224045 A1 | 10/2006 | Whipple et al. |
| 2006/0293557 A1 | 12/2006 | Chuanggui et al. |
| 2007/0014784 A1 | 1/2007 | Nayak et al. |
| 2007/0019781 A1 | 1/2007 | Haras |
| 2007/0040906 A1 | 2/2007 | Iketani |
| 2007/0093748 A1 | 4/2007 | Nayak et al. |
| 2007/0100210 A1 | 5/2007 | Selover et al. |
| 2007/0123912 A1 | 5/2007 | Carson |
| 2007/0156021 A1 | 7/2007 | Morse et al. |
| 2007/0172472 A1 | 7/2007 | Nayak |
| 2007/0175955 A1 | 8/2007 | Shelton et al. |
| 2007/0239149 A1 | 10/2007 | Lieponis |
| 2007/0265495 A1 | 11/2007 | Vayser |
| 2008/0001919 A1 | 1/2008 | Pascucci |
| 2008/0004633 A1 | 1/2008 | Arata et al. |
| 2008/0077158 A1 | 3/2008 | Haider et al. |
| 2008/0144906 A1* | 6/2008 | Allred ............. A61B 5/062 382/131 |
| 2008/0151233 A1 | 6/2008 | Blanke et al. |
| 2008/0194930 A1 | 8/2008 | Harris et al. |
| 2008/0228104 A1 | 9/2008 | Uber et al. |
| 2008/0269596 A1 | 10/2008 | Revie et al. |
| 2008/0319491 A1 | 12/2008 | Schoenefeld |
| 2009/0000627 A1 | 1/2009 | Quaid et al. |
| 2009/0234223 A1 | 9/2009 | Onoda et al. |
| 2010/0030231 A1 | 2/2010 | Revie et al. |
| 2010/0081875 A1 | 4/2010 | Fowler et al. |
| 2010/0087755 A1 | 4/2010 | Boezaart |
| 2010/0137882 A1 | 6/2010 | Quaid, III |
| 2010/0152539 A1 | 6/2010 | Ghabrial et al. |
| 2010/0280493 A1 | 11/2010 | Nayak |
| 2011/0014181 A1 | 1/2011 | Thornton |
| 2011/0071531 A1 | 3/2011 | Carson |
| 2011/0082369 A1 | 4/2011 | Mohr et al. |
| 2011/0201881 A1 | 8/2011 | Emch |
| 2011/0257611 A1 | 10/2011 | Locke et al. |
| 2011/0257661 A1 | 10/2011 | Choi et al. |
| 2011/0306985 A1 | 12/2011 | Inoue et al. |
| 2012/0004894 A1 | 1/2012 | Butler et al. |
| 2012/0046668 A1 | 2/2012 | Gantes |
| 2012/0143341 A1 | 6/2012 | Zipnick |
| 2012/0165837 A1 | 6/2012 | Belman et al. |
| 2012/0265022 A1 | 10/2012 | Menn |
| 2012/0300051 A1 | 11/2012 | Daigo et al. |
| 2013/0035583 A1 | 2/2013 | Park et al. |
| 2013/0172902 A1 | 7/2013 | Lightcap et al. |
| 2013/0211244 A1 | 8/2013 | Nathaniel |
| 2013/0274596 A1 | 10/2013 | Azizian et al. |
| 2013/0274673 A1 | 10/2013 | Fischell et al. |
| 2013/0274674 A1 | 10/2013 | Fischell et al. |
| 2013/0296712 A1 | 11/2013 | Durvasula |
| 2014/0005685 A1 | 1/2014 | Modrow et al. |
| 2014/0024945 A1 | 1/2014 | Mung et al. |
| 2014/0035762 A1 | 2/2014 | Shelton, IV et al. |
| 2014/0039520 A1 | 2/2014 | Haider et al. |
| 2014/0114180 A1* | 4/2014 | Jain ............. A61B 6/481 600/424 |
| 2014/0163359 A1 | 6/2014 | Sholev et al. |
| 2014/0163664 A1 | 6/2014 | Goldsmith |
| 2014/0171793 A1 | 6/2014 | Lin et al. |
| 2014/0175150 A1 | 6/2014 | Shelton, IV et al. |
| 2014/0179997 A1* | 6/2014 | von Grunberg ....... A61B 1/042 600/102 |
| 2014/0336461 A1 | 11/2014 | Reiter et al. |
| 2014/0378843 A1 | 12/2014 | Valdes et al. |
| 2015/0018999 A1 | 1/2015 | Lee et al. |
| 2015/0025548 A1 | 1/2015 | Franklin et al. |
| 2015/0032140 A1 | 1/2015 | Khouri |
| 2015/0051460 A1 | 2/2015 | Saxena et al. |
| 2015/0066107 A1 | 3/2015 | Richter et al. |
| 2015/0133909 A1 | 5/2015 | van der Weide et al. |
| 2015/0145966 A1 | 5/2015 | Krieger et al. |
| 2015/0223903 A1 | 8/2015 | Bell et al. |
| 2015/0238276 A1 | 8/2015 | Atarot et al. |
| 2015/0245878 A1 | 9/2015 | Jaramaz et al. |
| 2015/0297177 A1 | 10/2015 | Boctor et al. |
| 2015/0305650 A1 | 10/2015 | Hunter et al. |
| 2015/0366628 A1 | 12/2015 | Ingmanson |
| 2016/0000516 A1 | 1/2016 | Cheng et al. |
| 2016/0007827 A1 | 1/2016 | Frimer et al. |
| 2016/0014328 A1 | 1/2016 | Rokutanda |
| 2016/0022146 A1 | 1/2016 | Piron et al. |
| 2016/0038004 A1 | 2/2016 | Tanaka |
| 2016/0086380 A1 | 3/2016 | Vayser et al. |
| 2016/0183841 A1 | 6/2016 | Duindam et al. |
| 2016/0206204 A1 | 7/2016 | Matsuda et al. |
| 2016/0228090 A1 | 8/2016 | Boctor et al. |
| 2016/0235304 A1 | 8/2016 | Tzoumas et al. |
| 2016/0256101 A1 | 9/2016 | Aharoni et al. |
| 2016/0331467 A1 | 11/2016 | Slamin et al. |
| 2016/0346034 A1 | 12/2016 | Arya et al. |
| 2017/0007350 A1 | 1/2017 | Popovic et al. |
| 2017/0020613 A1 | 1/2017 | Kang et al. |
| 2017/0055819 A1 | 3/2017 | Hansen et al. |
| 2017/0059408 A1 | 3/2017 | Korner et al. |
| 2017/0071475 A1 | 3/2017 | Irisawa |
| 2017/0079530 A1 | 3/2017 | DiMaio et al. |
| 2017/0165008 A1 | 6/2017 | Finley |
| 2017/0172382 A1 | 6/2017 | Nir et al. |
| 2017/0172662 A1 | 6/2017 | Panescu et al. |
| 2017/0189006 A1 | 7/2017 | Shluzas et al. |
| 2017/0197028 A1 | 7/2017 | Goldsmith |
| 2017/0202624 A1 | 7/2017 | Atarot et al. |
| 2017/0238962 A1 | 8/2017 | Hansen et al. |
| 2017/0251900 A1 | 9/2017 | Hansen et al. |
| 2017/0258526 A1 | 9/2017 | Lang |
| 2017/0265943 A1 | 9/2017 | Sela et al. |
| 2017/0296213 A1 | 10/2017 | Swensgard et al. |
| 2017/0304007 A1 | 10/2017 | Piron et al. |
| 2017/0312032 A1 | 11/2017 | Amanatullah et al. |
| 2017/0366773 A1 | 12/2017 | Kiraly et al. |
| 2017/0367580 A1 | 12/2017 | DiMaio et al. |
| 2018/0014777 A1 | 1/2018 | Amir et al. |
| 2018/0014851 A1 | 1/2018 | Hansen et al. |
| 2018/0214016 A1 | 8/2018 | Thommen et al. |
| 2018/0247153 A1 | 8/2018 | Ganapati et al. |
| 2018/0271603 A1 | 9/2018 | Nir et al. |
| 2018/0333210 A1 | 11/2018 | Nijkamp et al. |
| 2018/0343381 A1 | 11/2018 | Kobayashi et al. |
| 2018/0344140 A1 | 12/2018 | Aizenfeld |
| 2018/0368883 A1 | 12/2018 | Rossa et al. |
| 2019/0008579 A1 | 1/2019 | Begg et al. |
| 2019/0022418 A1 | 1/2019 | Fishman |
| 2019/0046276 A1 | 2/2019 | Inglese et al. |
| 2019/0053691 A1 | 2/2019 | Hansen et al. |
| 2019/0053872 A1 | 2/2019 | Meglan |
| 2019/0069824 A1 | 3/2019 | Darty et al. |
| 2019/0076186 A1 | 3/2019 | Fischell et al. |
| 2019/0099070 A1 | 4/2019 | Mark et al. |
| 2019/0099226 A1 | 4/2019 | Hallen |
| 2019/0104919 A1 | 4/2019 | Shelton, IV et al. |
| 2019/0110924 A1 | 4/2019 | Moreno et al. |
| 2019/0117319 A1 | 4/2019 | Cima et al. |
| 2019/0142524 A1 | 5/2019 | Hladio et al. |
| 2019/0175272 A1 | 6/2019 | Khan et al. |
| 2019/0180865 A1 | 6/2019 | Kashima et al. |

(56) References Cited

U.S. PATENT DOCUMENTS

| | | |
|---|---|---|
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200998 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201102 A1 | 7/2019 | Shelton, IV et al. |
| 2019/0201120 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0205567 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0208641 A1 | 7/2019 | Yates et al. |
| 2019/0247050 A1 | 8/2019 | Goldsmith |
| 2019/0269476 A1 | 9/2019 | Bowling et al. |
| 2019/0293554 A1 | 9/2019 | Nakao et al. |
| 2019/0307524 A1 | 10/2019 | Popovic |
| 2019/0311542 A1 | 10/2019 | Douglas et al. |
| 2019/0320117 A1 | 10/2019 | Wu et al. |
| 2019/0320878 A1 | 10/2019 | Duindam et al. |
| 2019/0321118 A1 | 10/2019 | Genova et al. |
| 2019/0388157 A1 | 12/2019 | Shameli et al. |
| 2020/0008879 A1 | 1/2020 | Popovic et al. |
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015904 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015924 A1 | 1/2020 | Scheib et al. |
| 2020/0015925 A1 | 1/2020 | Scheib |
| 2020/0018844 A1 | 1/2020 | Fridman et al. |
| 2020/0037858 A1 | 2/2020 | Pedreira de Cerqueira Filho |
| 2020/0038112 A1 | 2/2020 | Amanatullah et al. |
| 2020/0060725 A1 | 2/2020 | Sato |
| 2020/0121245 A1 | 4/2020 | Barclay et al. |
| 2020/0281662 A1 | 9/2020 | Cong et al. |
| 2020/0289205 A1 | 9/2020 | Scheib et al. |
| 2020/0289216 A1 | 9/2020 | Denlinger et al. |
| 2020/0289217 A1 | 9/2020 | Denlinger et al. |
| 2020/0289219 A1 | 9/2020 | Denlinger et al. |
| 2020/0289220 A1 | 9/2020 | Denlinger et al. |
| 2020/0289221 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0289229 A1 | 9/2020 | Denlinger et al. |
| 2020/0289230 A1 | 9/2020 | Denlinger et al. |
| 2020/0291476 A1 | 9/2020 | Deng et al. |
| 2020/0315721 A1 | 10/2020 | Rabindran et al. |
| 2020/0367972 A1 | 11/2020 | Zhang et al. |
| 2020/0397266 A1 | 12/2020 | Hufford |
| 2020/0405395 A1 | 12/2020 | Gullotti et al. |
| 2021/0068908 A1 | 3/2021 | Thienphrapa et al. |
| 2021/0137634 A1 | 5/2021 | Lang |
| 2021/0196098 A1 | 7/2021 | Shelton, IV et al. |
| 2021/0196108 A1 | 7/2021 | Shelton, IV |
| 2021/0196109 A1 | 7/2021 | Shelton, IV et al. |
| 2021/0196381 A1 | 7/2021 | Eckert et al. |
| 2021/0196382 A1 | 7/2021 | Mumaw et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0196424 A1 | 7/2021 | Shelton, IV et al. |
| 2021/0196425 A1 | 7/2021 | Shelton, IV et al. |
| 2021/0199557 A1 | 7/2021 | Shelton, IV et al. |
| 2021/0205019 A1 | 7/2021 | Shelton, IV et al. |
| 2021/0212792 A1 | 7/2021 | Shelton, IV et al. |
| 2021/0259660 A1 | 8/2021 | Bharat et al. |
| 2021/0259789 A1 | 8/2021 | Wright et al. |
| 2021/0275251 A1 | 9/2021 | Shelton, IV et al. |
| 2021/0275252 A1 | 9/2021 | Shelton, IV et al. |
| 2021/0282861 A1 | 9/2021 | Eckert et al. |
| 2021/0307835 A1 | 10/2021 | Shelton, IV et al. |
| 2021/0307865 A1 | 10/2021 | Shelton, IV et al. |
| 2021/0307866 A1 | 10/2021 | Shelton, IV et al. |
| 2021/0307867 A1 | 10/2021 | Shelton, IV et al. |
| 2021/0307868 A1 | 10/2021 | Shelton, IV et al. |
| 2021/0307869 A1 | 10/2021 | Shelton, IV et al. |
| 2021/0307870 A1 | 10/2021 | Shelton, IV et al. |
| 2022/0000559 A1 | 1/2022 | Leonard et al. |
| 2022/0000565 A1 | 1/2022 | Gururaj et al. |
| 2022/0047259 A1 | 2/2022 | Prior et al. |
| 2022/0133412 A1 | 5/2022 | Tolkowsky et al. |

FOREIGN PATENT DOCUMENTS

| | | | |
|---|---|---|---|
| EP | 2754383 | A2 | 7/2014 |
| JP | 2006280591 | A | 10/2006 |
| JP | 4106991 | B2 | 6/2008 |
| KR | 20120068597 | A | 6/2012 |
| WO | WO-2008033133 | A2 | 3/2008 |
| WO | WO-2013093391 | A1 | 6/2013 |
| WO | WO-2013163391 | A1 | 10/2013 |
| WO | WO-2015135058 | A1 | 9/2015 |
| WO | WO-2018200767 | A1 | 11/2018 |
| WO | WO-2019130085 | A1 | 7/2019 |
| WO | WO-2020116991 | A1 | 6/2020 |

OTHER PUBLICATIONS

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

Elhajj, et al., "Sleeve Gastrectomy Surgical Assistive Instrument for Accurate Remnant Stomach Volume," ASME, J. Med. Devices, vol. 4, pp. 1-10, Jun. 2010.

Brecht, Hans-Peter et al., "Whole-body three-dimensional optoacoustic tomography system for small animals," Journal of Biomedical Optics, vol. 14, No. 6, 064007-1-064007-7 (2009).

Ge, Jiawei et al., "Landmark-Guided Deformable Image Registration for Supervised Autonomous Robotic Tumor Resection," Advances in Intelligent Data Analysis XIX, LNCS, Springer International Publishing, pp. 320-328, Oct. 10, 2019.

\* cited by examiner

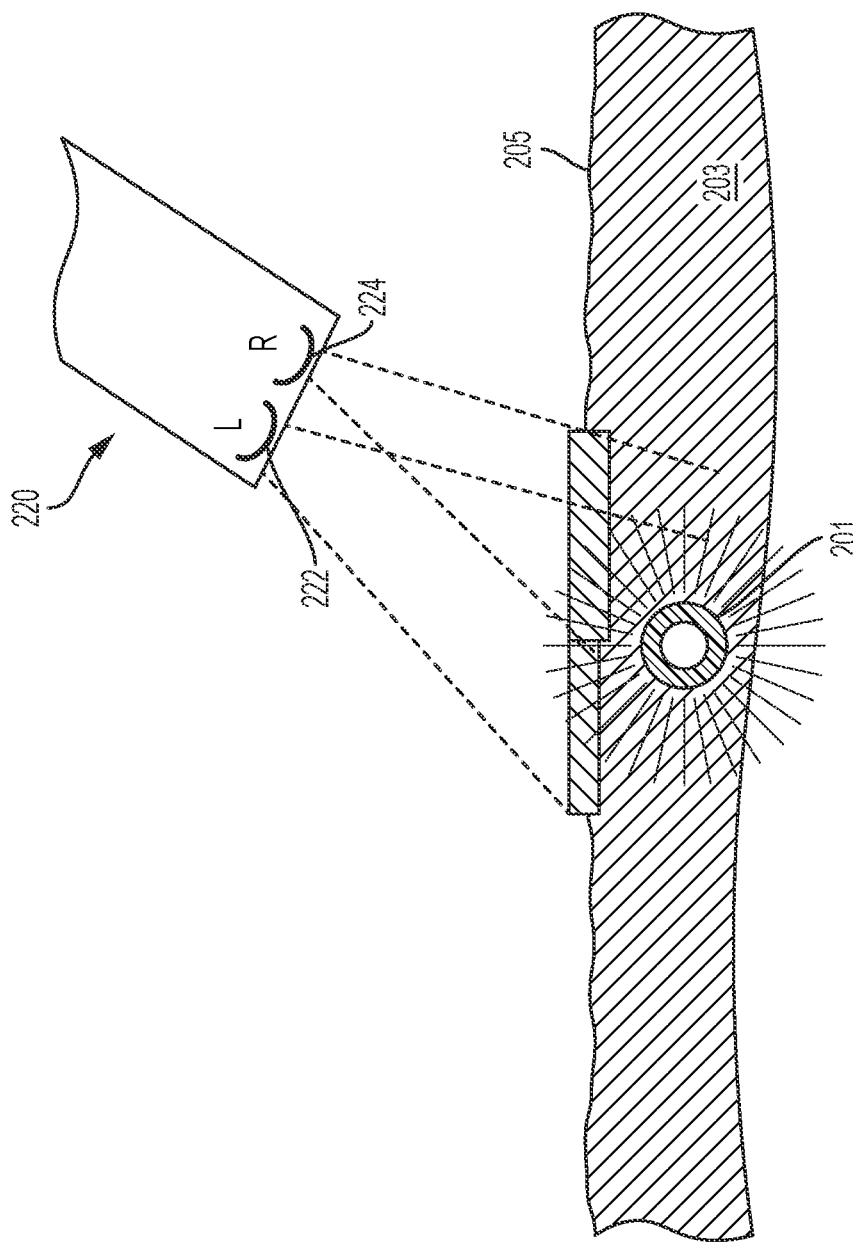

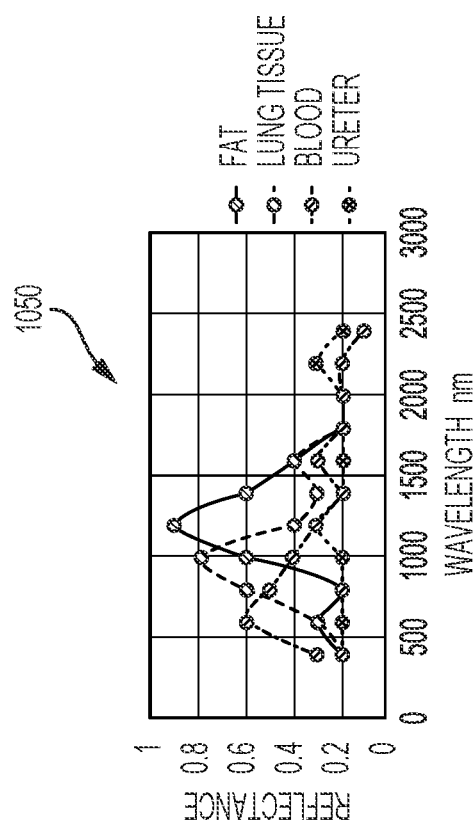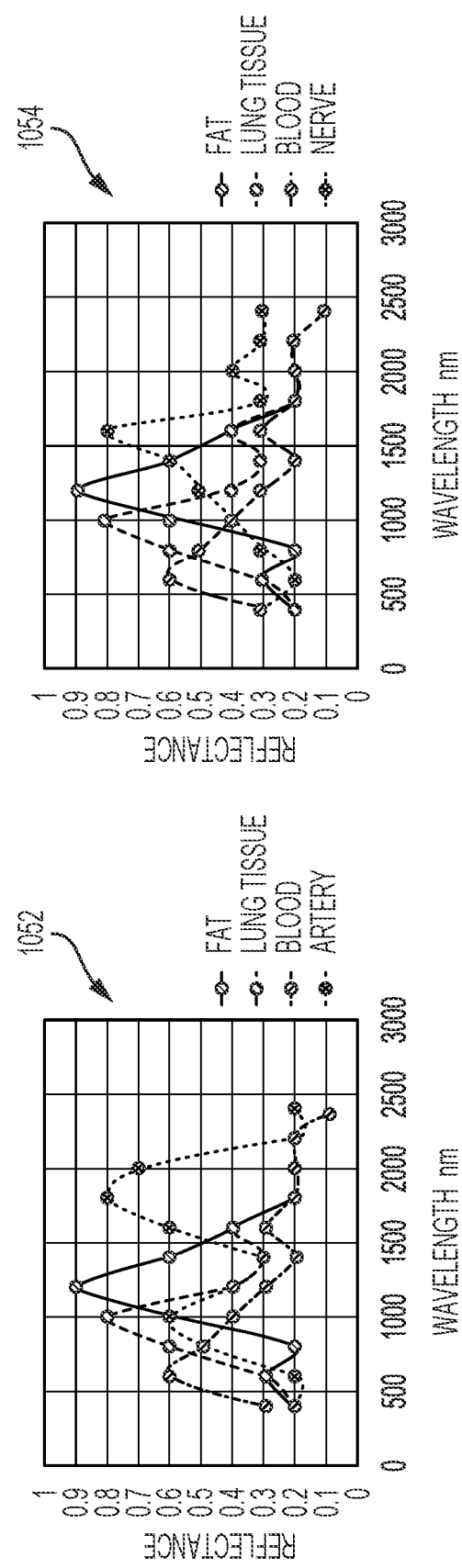

| WHAT THE HUB KNOWS | TYPE OF DATA | PROCEDURE STEP |
|---|---|---|
| THORACIC PROCEDURE | SELECT PATIENT DATA 2502 | PULL ELECTRONIC MEDICAL RECORDS |
| NOT A WEDGE PROCEDURE | SCAN PRODUCTS 2504 | SCAN INCOMING SUPPLIES |
| CONFIRM PATIENT | UNIQUE ID 2506 | SCAN PATIENT BAND |
| VATS | SMOKE EVAC. DATA / INSUFFLATION DATA / SCOPE DATA 2508 | TURN ON HUB AUXILIARY EQUIPMENT |
| CONFIRM PATIENT IS IN O.R. | EKG DATA 2510 | ATTACH EKG |
| PATIENT UNDER | EKG, BP AND VENTILATOR DATA 2512 | INDUCE ANESTHESIA |
| PROCEDURE BEGINS | VENTILATOR DATA 2514 | COLLAPSE LUNG |
| CONFIRM LOBECTOMY vs. SEGMENTECTOMY LAP PORTION STARTS | SCOPE DATA 2516 | SCOPE IMAGE |

| WHAT THE HUB KNOWS | TYPE OF DATA | PROCEDURE STEP |
|---|---|---|
| DISSECT TO MOBILIZE LUNG | GENERATOR DATA 2518 | DISSECTION |
| LIGATE ARTERY & VEIN | STAPLER DATA 2520 | LIGATION |
| TRANSECT PARENCHYMA | STAPLER & CARTRIDGE DATA 2522 | SEGMENTECTOMY |
| DISSECT NODES | LEAK TEST | |
| | GENERATOR DATA 2524 | NODE DISSECTION |
| PATIENT EMERGENCE | GENERATOR / VENTILATOR DATA 2526 | REVERSE ANESTHESIA |
| PATIENT TRANSFER TO RECOVERY ROOM | LOSS OF EKG DATA / LOSS OF BP DATA 2528 | REMOVE MONITORS |

FIG. 21

VISUALIZATION SYSTEMS USING STRUCTURED LIGHT

CROSS-REFERENCE TO RELATED APPLICATIONS

This application is a continuation patent application claiming priority under 35 U.S.C. § 120 to U.S. patent application Ser. No. 16/729,744, titled VISUALIZATION SYSTEMS USING STRUCTURED LIGHT, filed Dec. 30, 2019, which issued on Jan. 11, 2022 as U.S. Pat. No. 11,219,501, the disclosure of which is herein incorporated by reference in its entirety.

This application is also a continuation patent application claiming priority under 35 U.S.C. § 120 to U.S. patent application Ser. No. 16/729,778, titled SYSTEM AND METHOD FOR DETERMINING, ADJUSTING, AND MANAGING RESECTION MARGIN ABOUT A SUBJECT TISSUE, filed Dec. 30, 2019, the disclosure of which is herein incorporated by reference in its entirety.

This application is also a continuation patent application claiming priority under 35 U.S.C. § 120 to U.S. patent application Ser. No. 16/729,737, titled ADAPTIVE SURGICAL SYSTEM CONTROL ACCORDING TO SURGICAL SMOKE CLOUD CHARACTERISTICS, filed Dec. 30, 2019, the disclosure of which is herein incorporated by reference in its entirety.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In one general aspect, a surgical visualization system comprising a first light source configured to emit a first pattern of structured light at a first wavelength, a second light source configured to emit a second pattern of structured light at a second wavelength that is different than the first wavelength, an image sensor configured to detect the first pattern of structured light and the second pattern of structured light on an anatomical structure, and a control circuit is disclosed. The control circuit is configured to receive first imaging data from the image sensor. The first imaging data is indicative of an outer surface contour of the anatomical structure from the first pattern of structured light detected by the image sensor. The control circuit is further configured to receive second imaging data from the image sensor. The second imaging data is indicative of a subsurface contour of the anatomical structure from the second pattern of structured light. The control circuit is further configured to generate a three-dimensional digital representation of the anatomical structure including the outer surface contour and the subsurface contour.

In another general aspect, a non-transitory computer-readable medium storing computer readable instructions, which when executed, cause a machine to detect, by an image sensor, a first pattern of structured light on an anatomical surface contour and a second pattern of structured light on a subsurface contour of the anatomical surface contour is disclosed. The non-transitory computer-readable medium storing computer readable instructions, which when executed, further cause the machine to transmit, to a control circuit, first imaging data indicative of the first pattern of structured light and second imaging data indicative of the second pattern of structured light. The non-transitory computer-readable medium storing computer readable instructions, which when executed, further cause the machine to process, by the control circuit, the first imaging data and the second imaging data. The non-transitory computer-readable medium storing computer readable instructions, which when executed, further cause the machine to generate, by the control circuit a three-dimensional digital representation of an anatomical structure including the anatomical surface contour and the subsurface contour. The non-transitory computer-readable medium storing computer readable instructions, which when executed, further cause the machine to transmit, to a monitor, the three-dimensional digital representation of the anatomical structure.

In yet another general aspect, a surgical system comprising a situational awareness module configured to determine a surgical scenario based on input signals from multiple surgical devices is disclosed. The surgical system further comprises a visualization system comprising a plurality of light sources, an image sensor configured to detect imaging data from the plurality of light sources, and a control circuit communicatively coupled to the situational awareness module. At least one of the plurality of light sources is configured to emit a pattern of structured light onto an anatomical structure. The control circuit is configured to receive the imaging data from the image sensor, generate a three-dimensional digital representation of the anatomical structure from the pattern of structured light detected by the imaging data, obtain metadata from the imaging data, overlay the metadata on the three-dimensional digital representation, receive updated imaging data from the image sensor, generate an updated three-dimensional digital representation of the anatomical structure based on the updated imaging data, and in response to a surgical scenario determined by the situational awareness module, update the overlaid metadata on the updated three-dimensional digital representation of the anatomical structure.

FIGURES

The novel features of the various aspects are set forth with particularity in the appended claims. The described aspects, however, both as to organization and methods of operation, may be best understood by reference to the following description, taken in conjunction with the accompanying drawings in which:

FIG. 6 is a schematic of a surgical visualization system including a three-dimensional camera, wherein the surgical visualization system is configured to identify a critical structure that is embedded within tissue, according to at least one aspect of the present disclosure.

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

FIGS. 13C-13E depict illustrative hyperspectral identifying signatures to differentiate anatomy from obscurants, wherein FIG. 13C is a graphical representation of a ureter signature versus obscurants, FIG. 13D is a graphical representation of an artery signature versus obscurants, and FIG. 13E is a graphical representation of a nerve signature versus obscurants, according to at least one aspect of the present disclosure.

Figure 14:
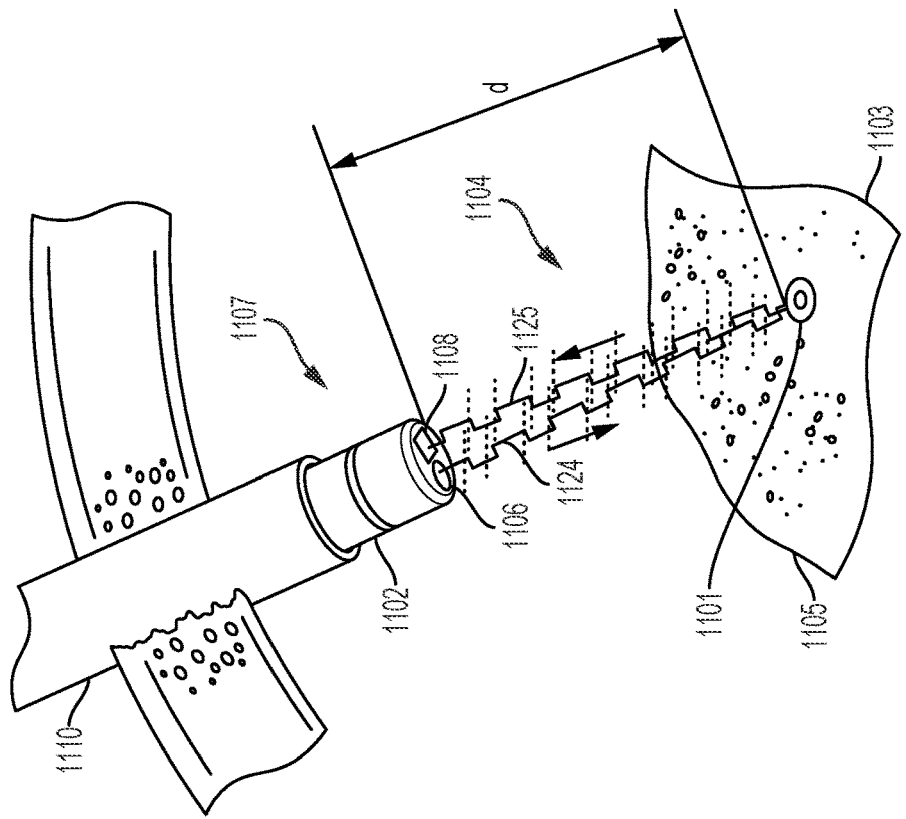

FIG. 14 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 15:
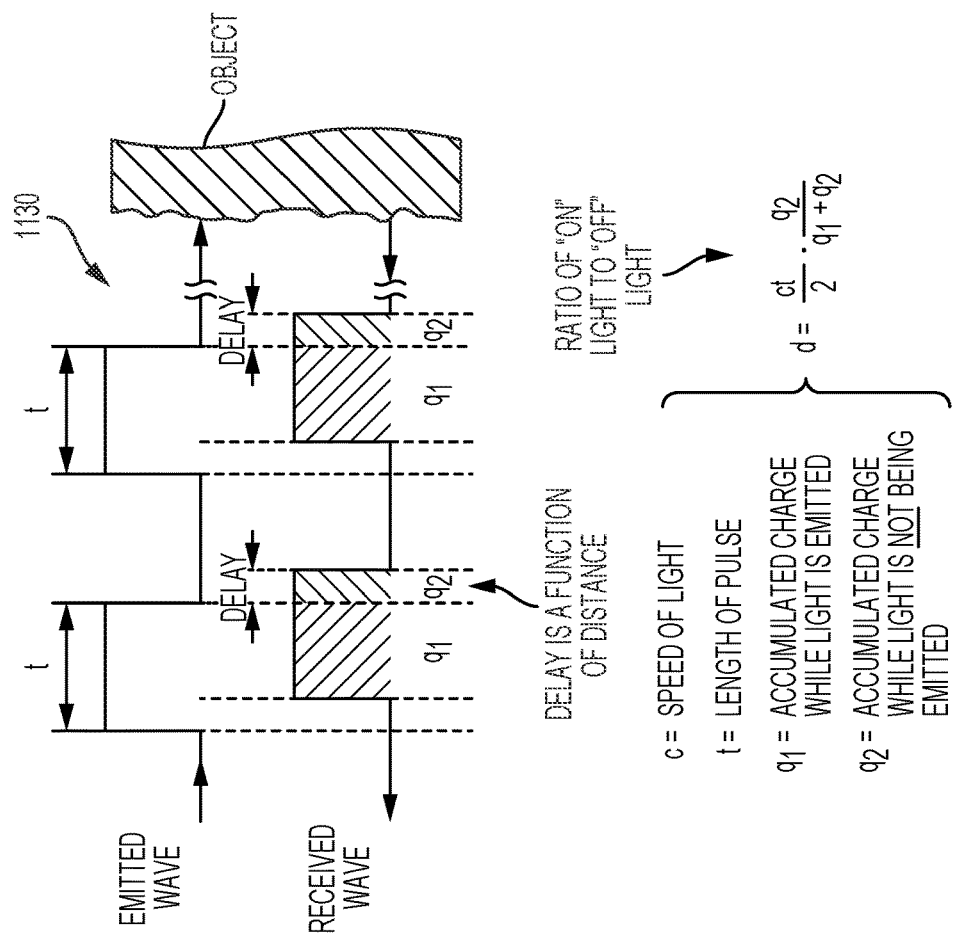

FIG. 15 is a schematic of an emitted wave, a received wave, and a delay between the emitted wave and the received wave of the NIR time-of-flight measurement system of FIG. 17A, according to at least one aspect of the present disclosure.

Figure 16:
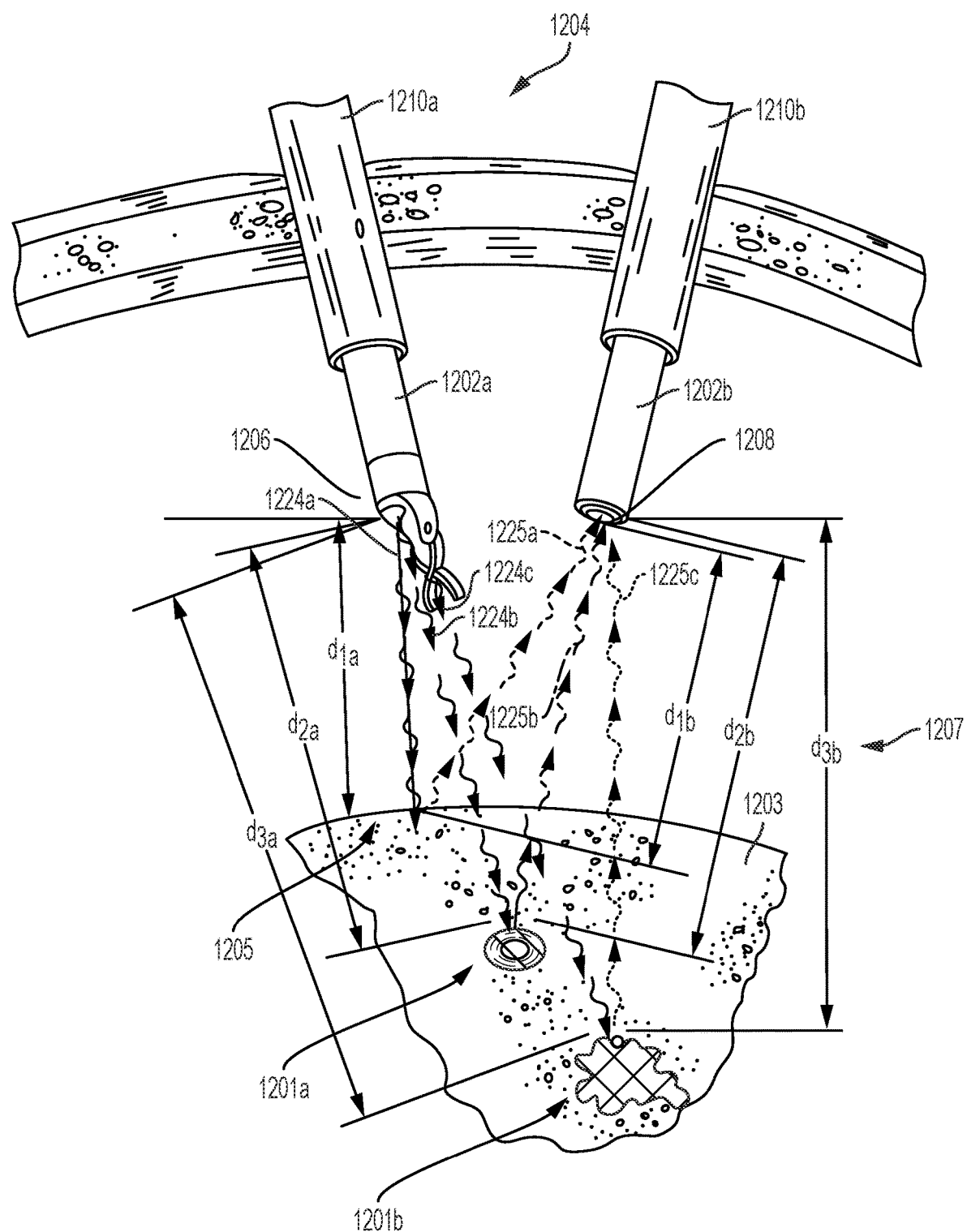

FIG. 16 illustrates a NIR time-of-flight measurement system configured to sense a distance to different structures, the time-of-flight measurement system including a transmitter (emitter) and a receiver (sensor) on separate devices, according to at least one aspect of the present disclosure.

Figure 17:
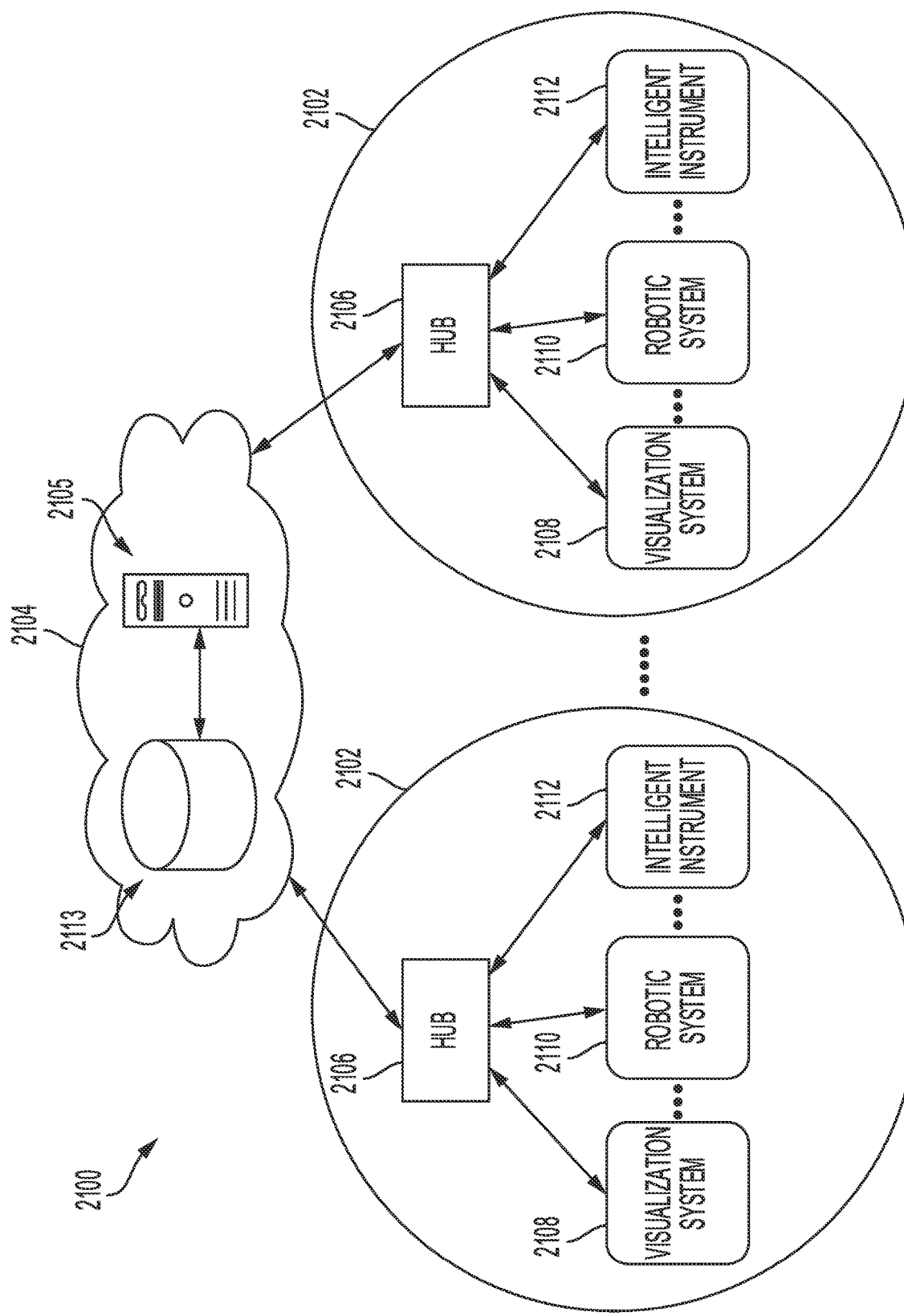

FIG. 17 is a block diagram of a computer-implemented interactive surgical system, according to at least one aspect of the present disclosure.

Figure 18:
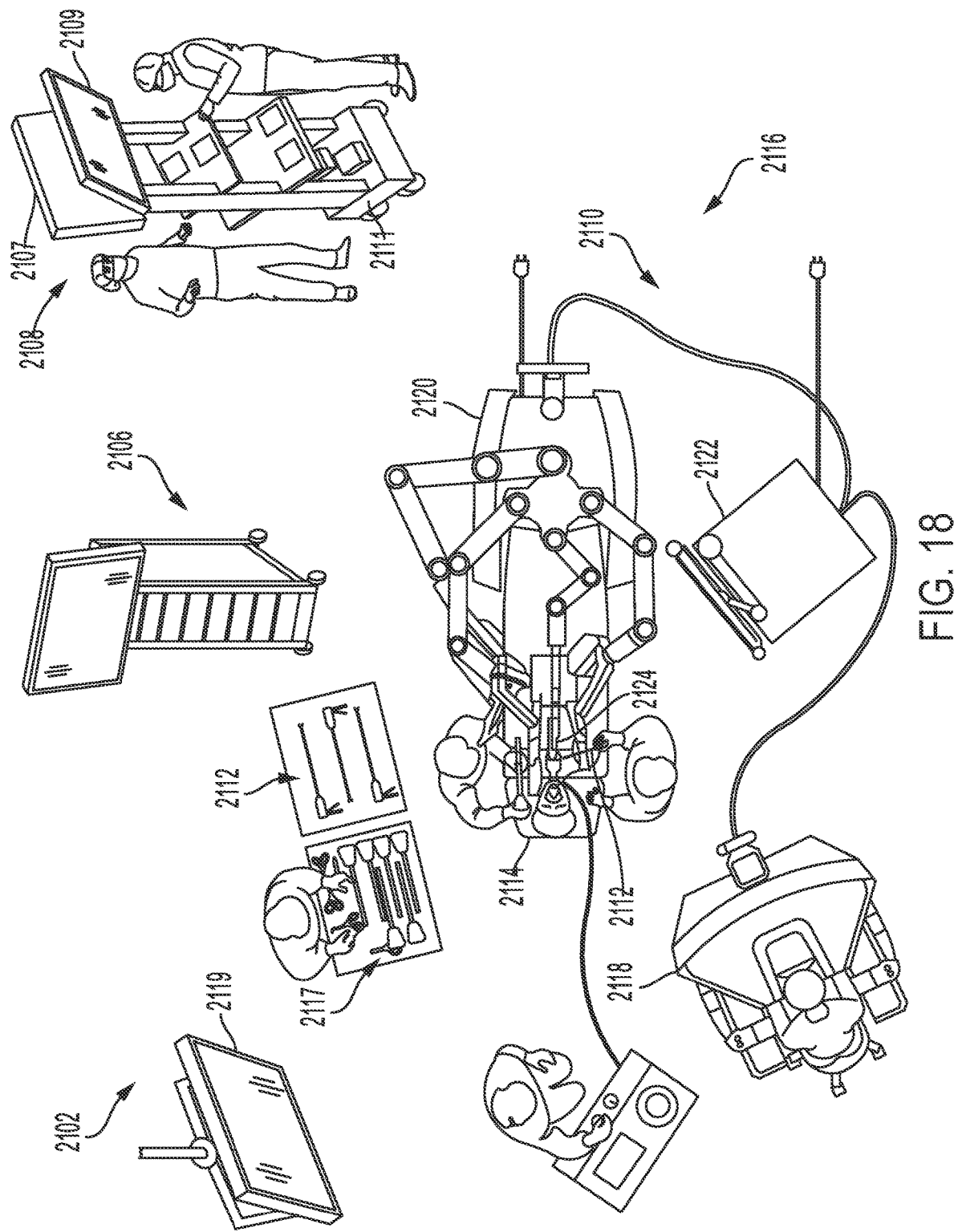

FIG. 18 is a surgical system being used to perform a surgical procedure in an operating room, according to at least one aspect of the present disclosure.

Figure 19:
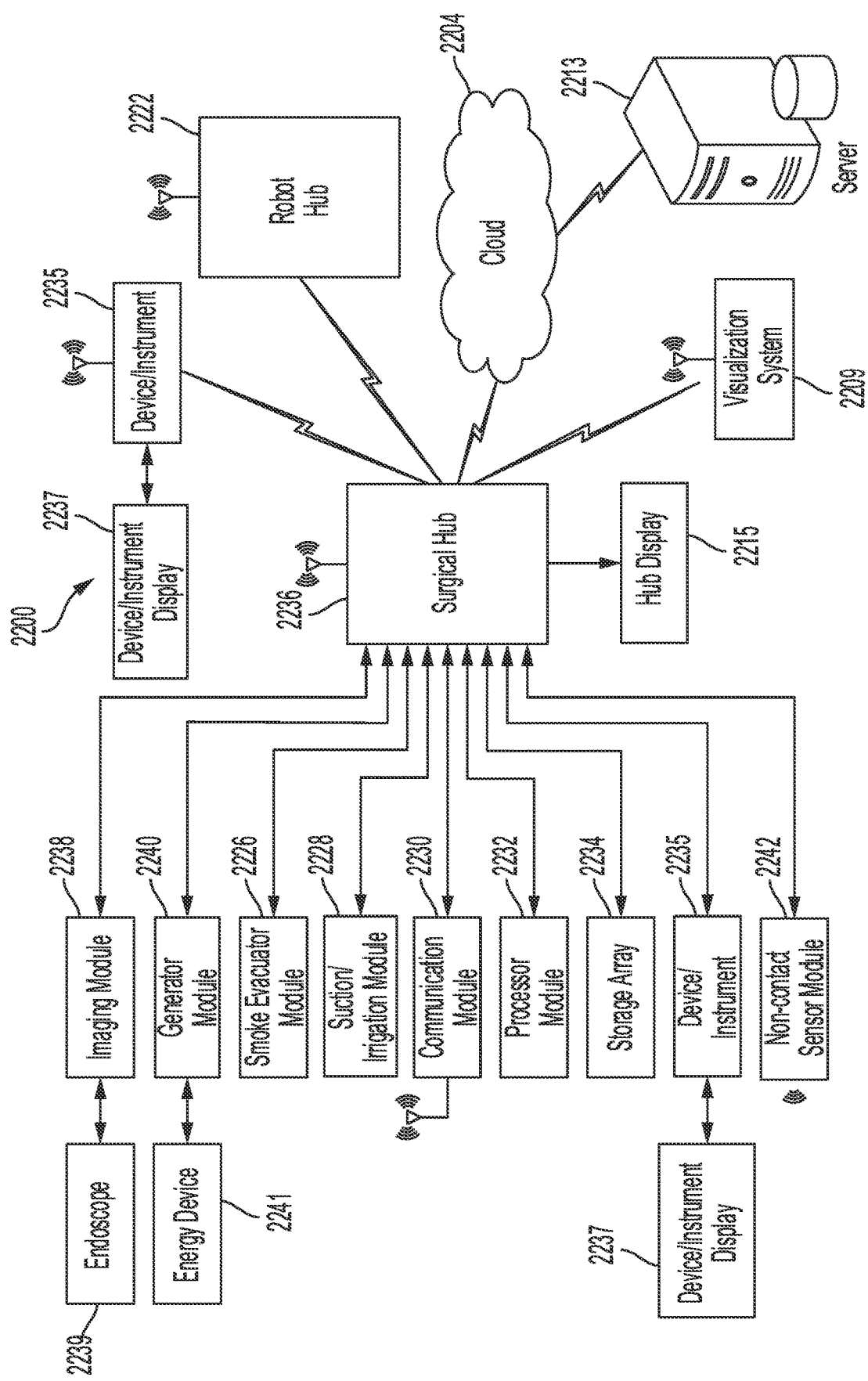

FIG. 19 illustrates a computer-implemented interactive surgical system, according to at least one aspect of the present disclosure.

Figure 20:
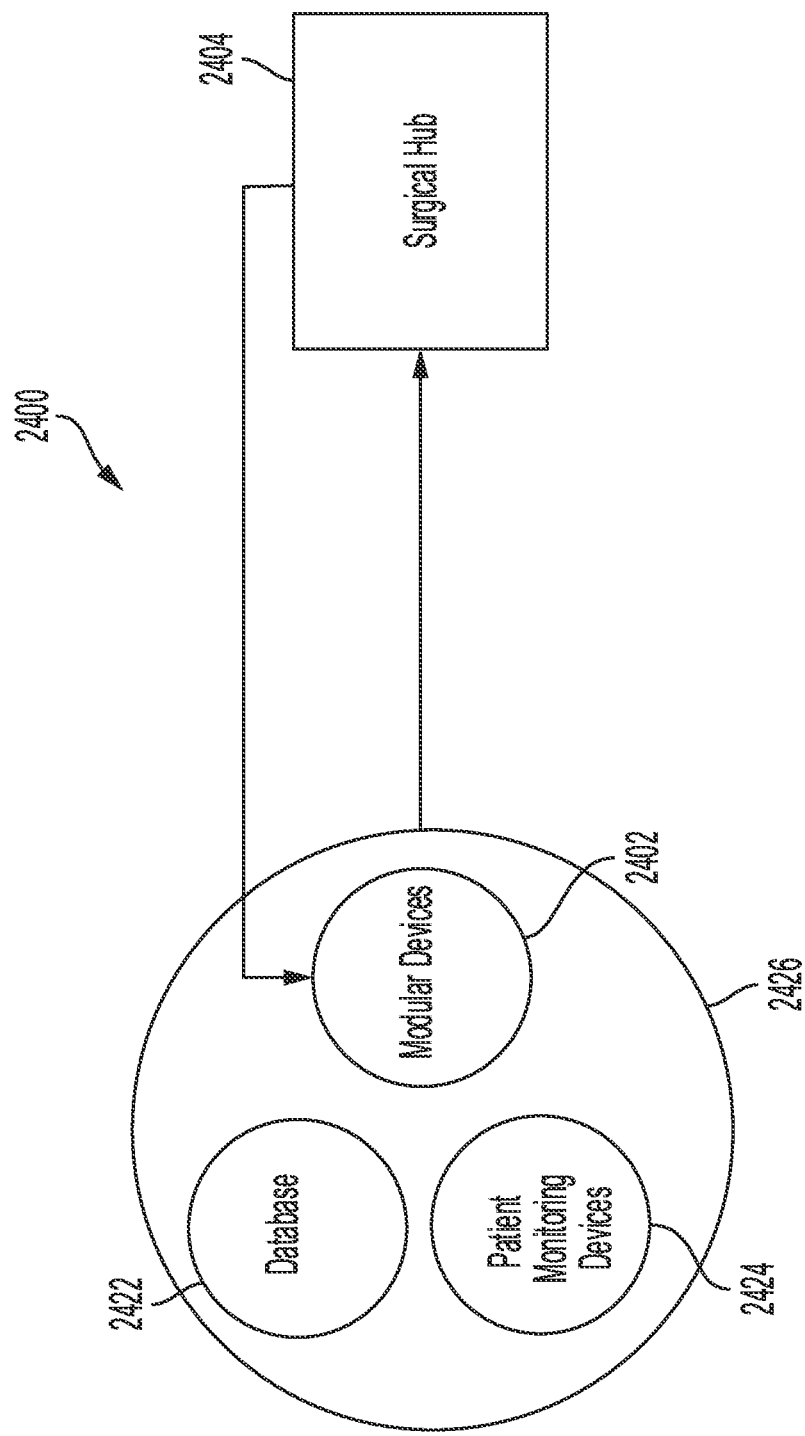

FIG. 20 illustrates a diagram of a situationally aware surgical system, according to at least one aspect of the present disclosure.

FIG. 21 illustrates a timeline depicting situational awareness of a hub, according to at least one aspect of the present disclosure.

Figure 22:
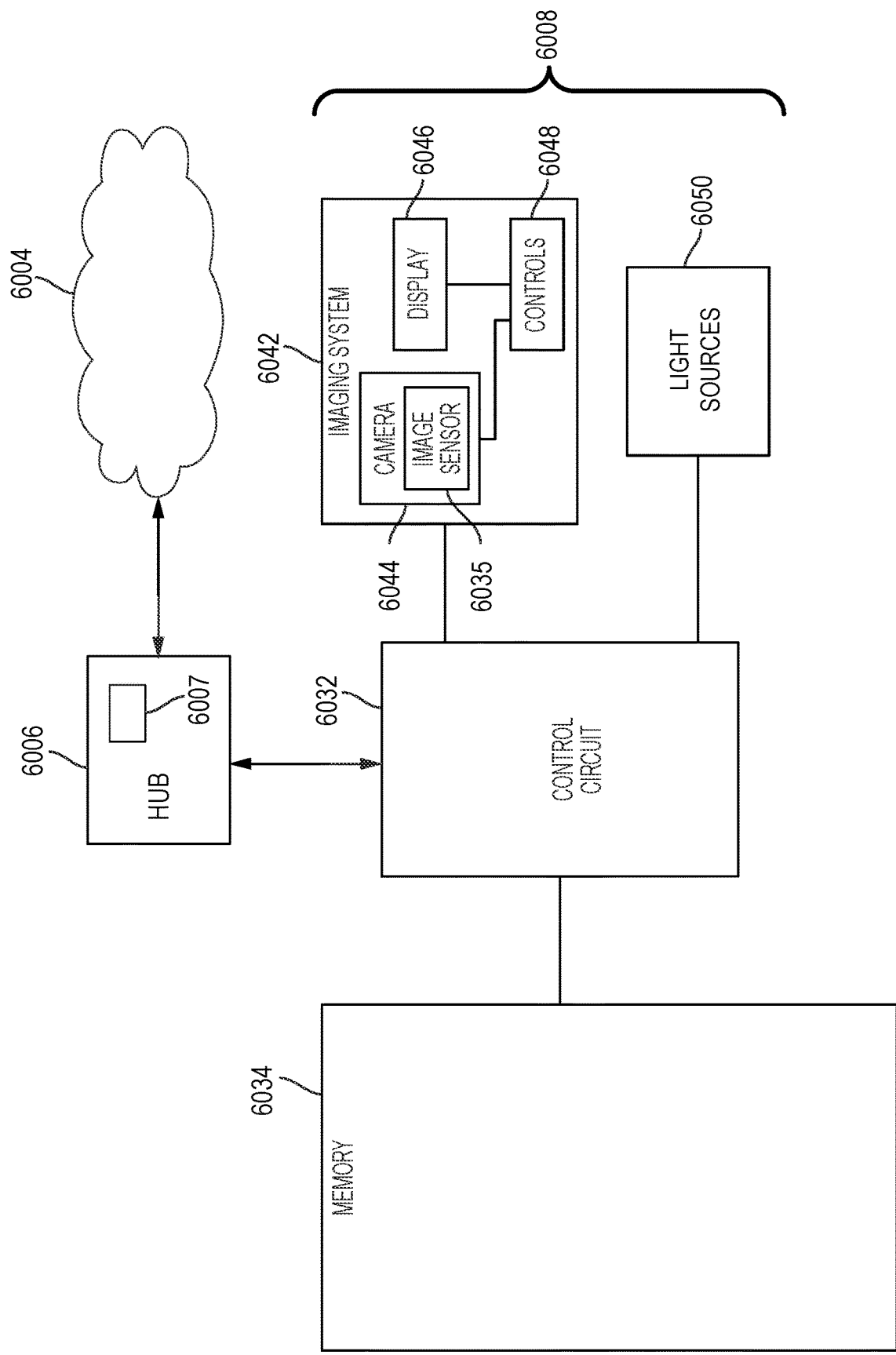

FIG. 22 is a schematic showing portions of a computer-implemented interactive surgical system including an adaptive surgical visualization system, according to at least one aspect of the present disclosure.

Figure 23:
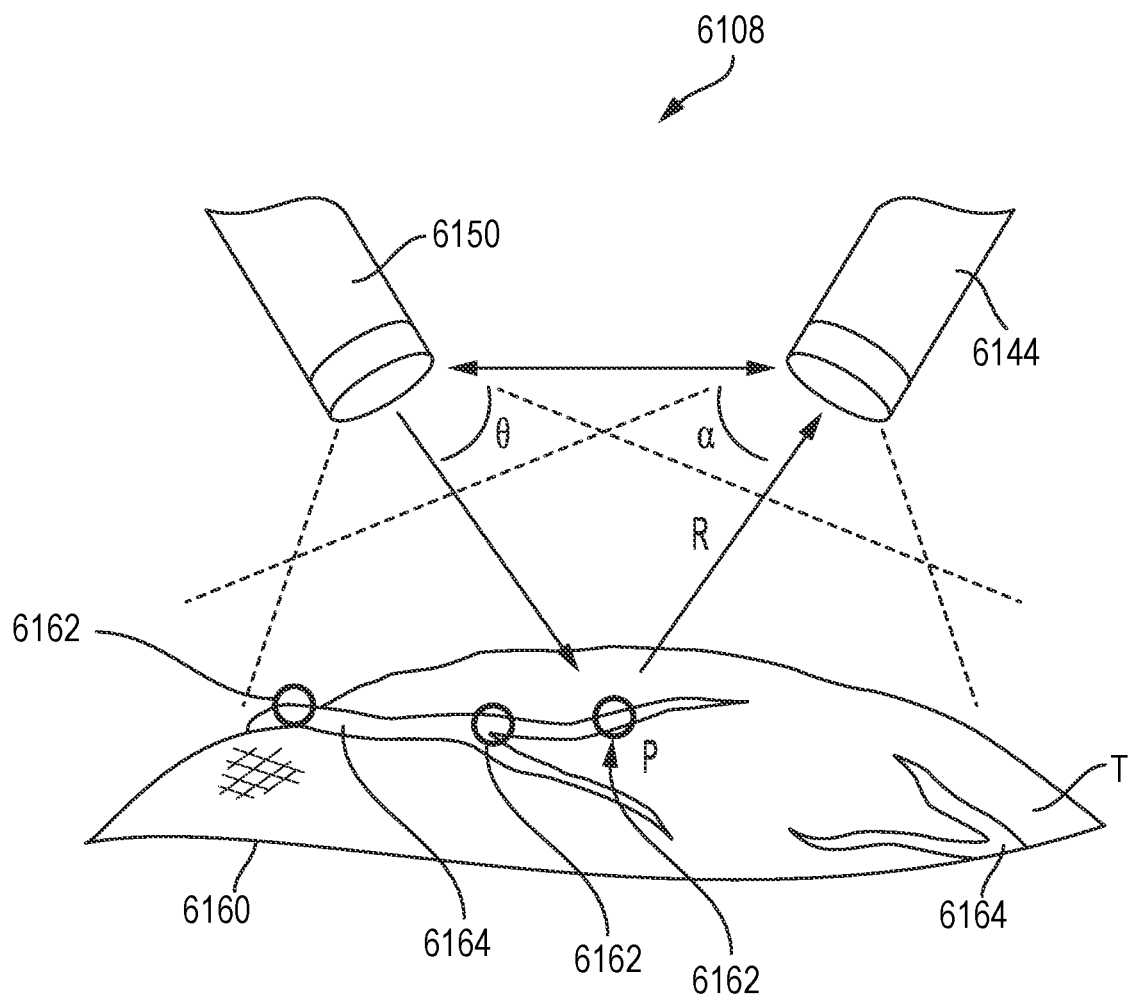

FIG. 23 is a schematic of a surgical visualization system including a structured light projector and a camera, according to at least one aspect of the present disclosure.

Figure 24:
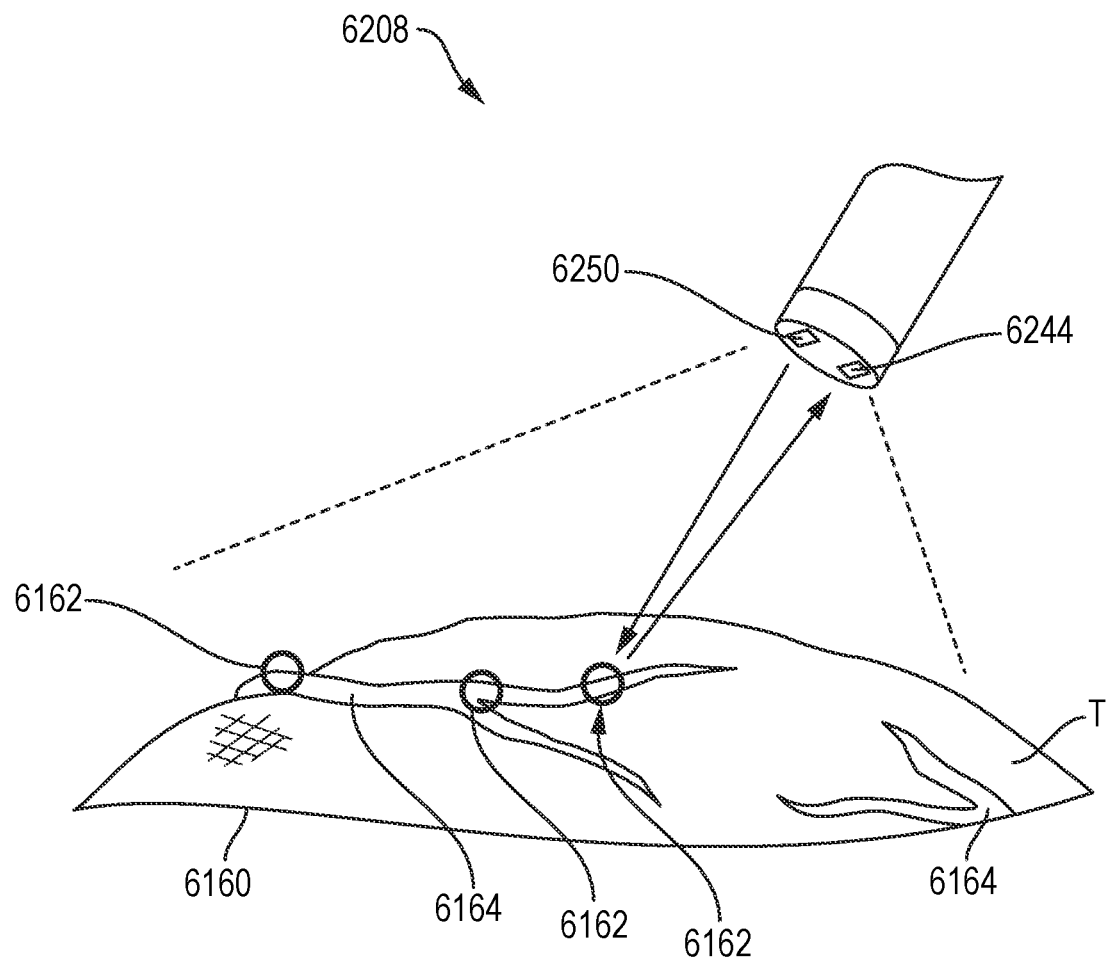

FIG. 24 is a schematic of a surgical visualization system including a surgical device including a structured light projector and a camera, according to at least one aspect of the present disclosure.

Figure 25A:
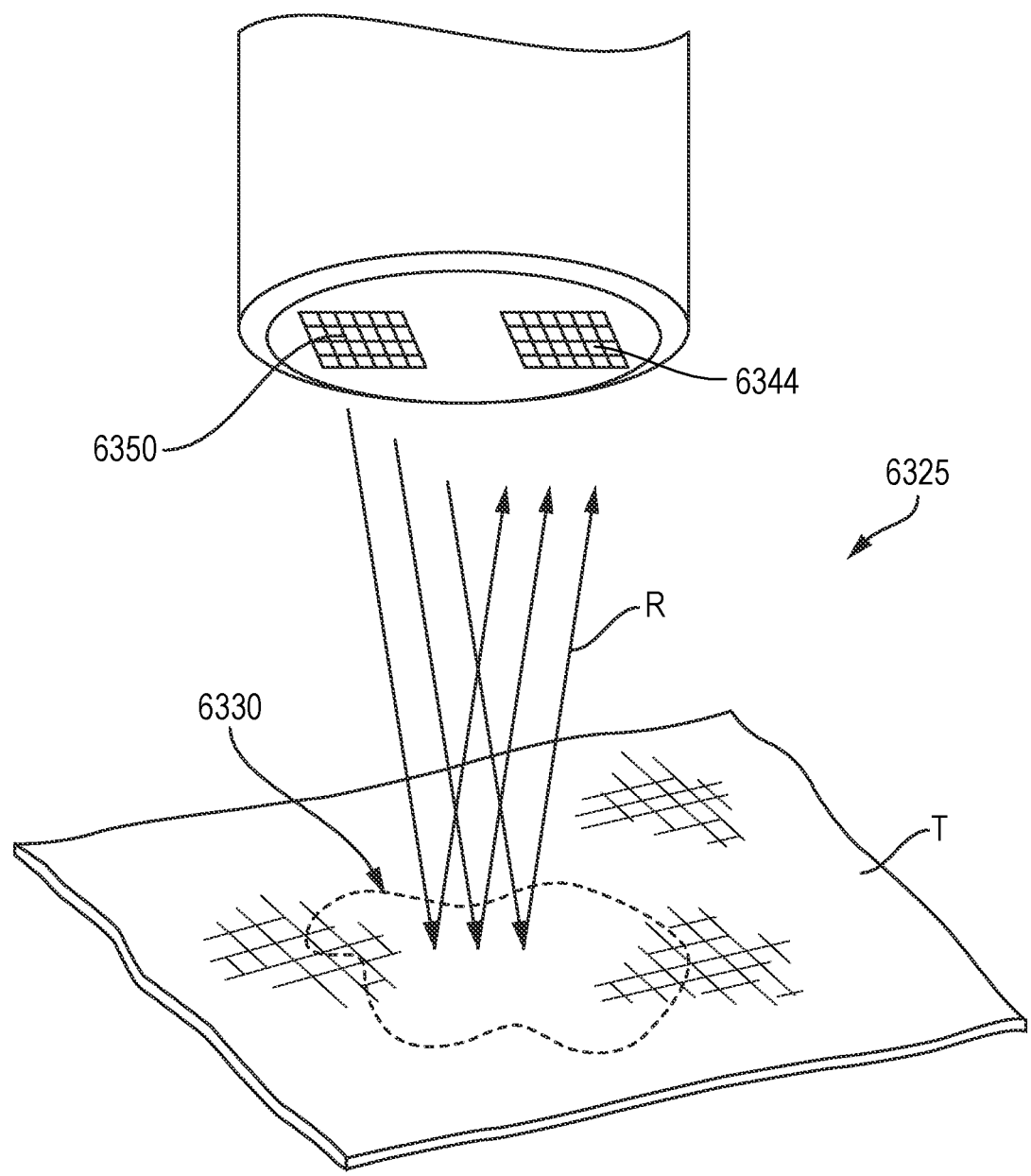

FIG. 25A is a schematic of a surgical device for visualizing tissue and depicting an expected refractivity, according to at least one aspect of the present disclosure.

Figure 25B:
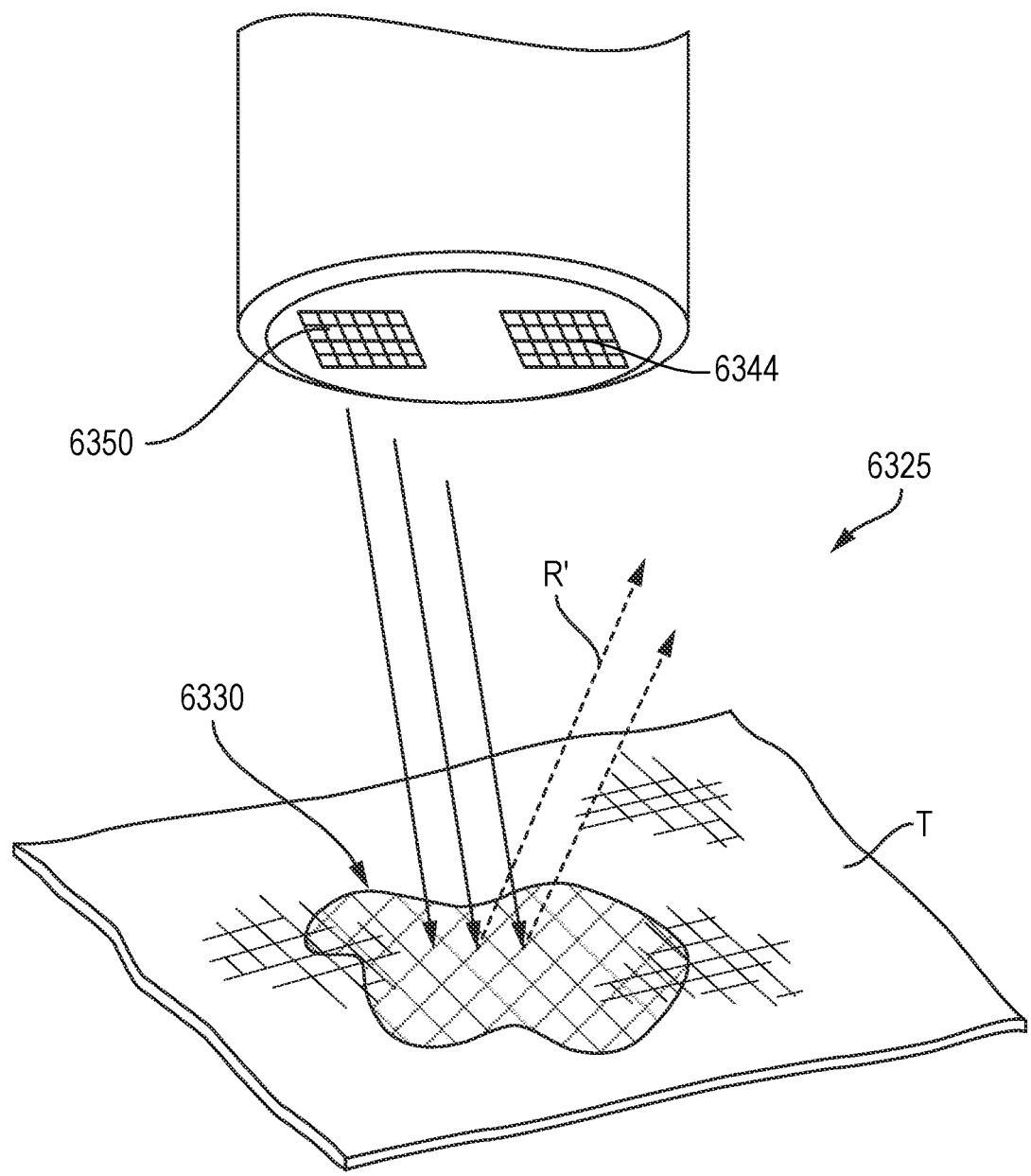

FIG. 25B is a schematic of the surgical device of FIG. 25A depicting the actual refractivity, according to at least one aspect of the present disclosure.

Figure 26:
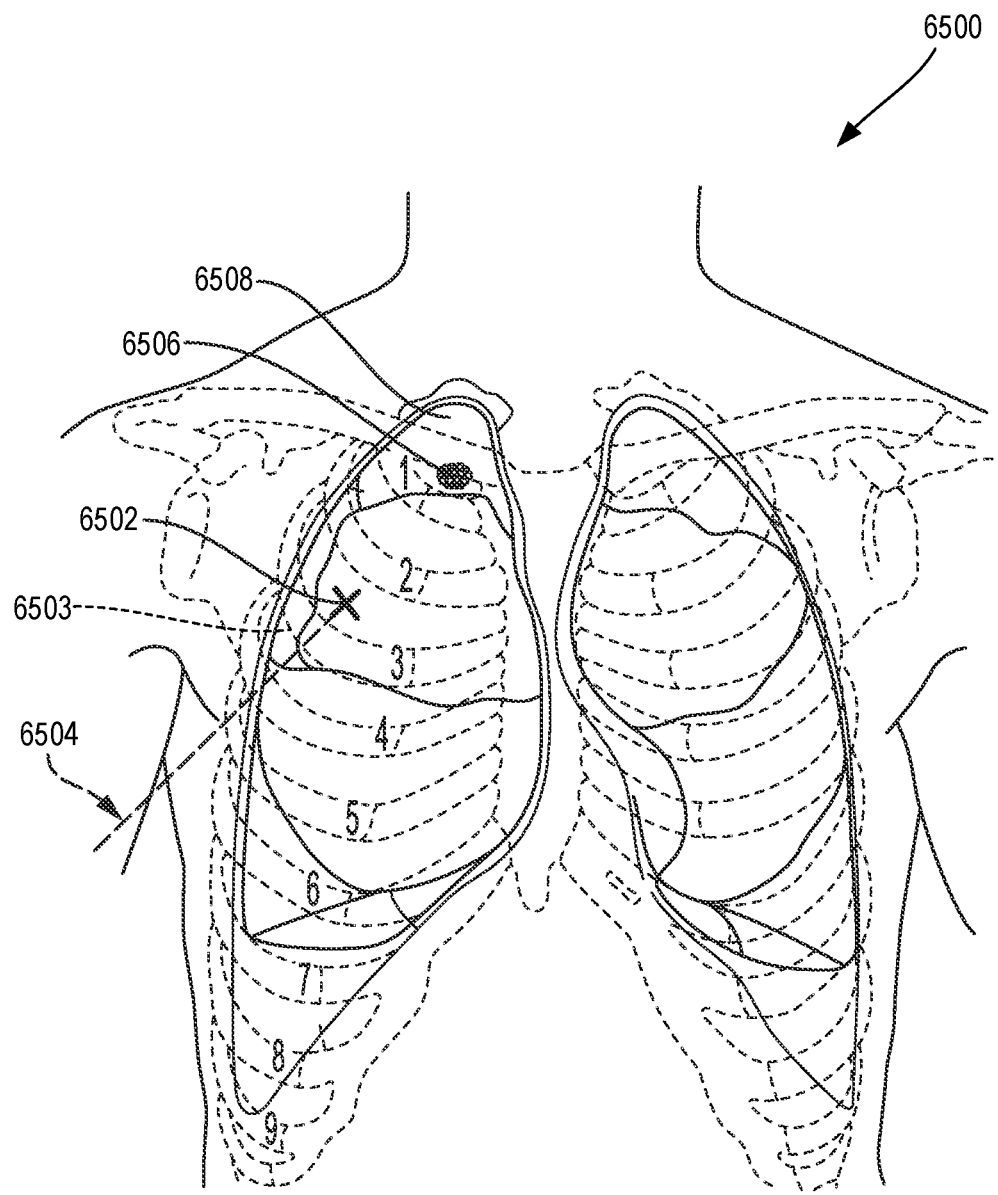

FIG. 26 is a diagram of a surgical instrument access path for a video-assisted thoracoscopic surgery (VATS) procedure, in accordance with at least one aspect of the present disclosure.

Figure 27:
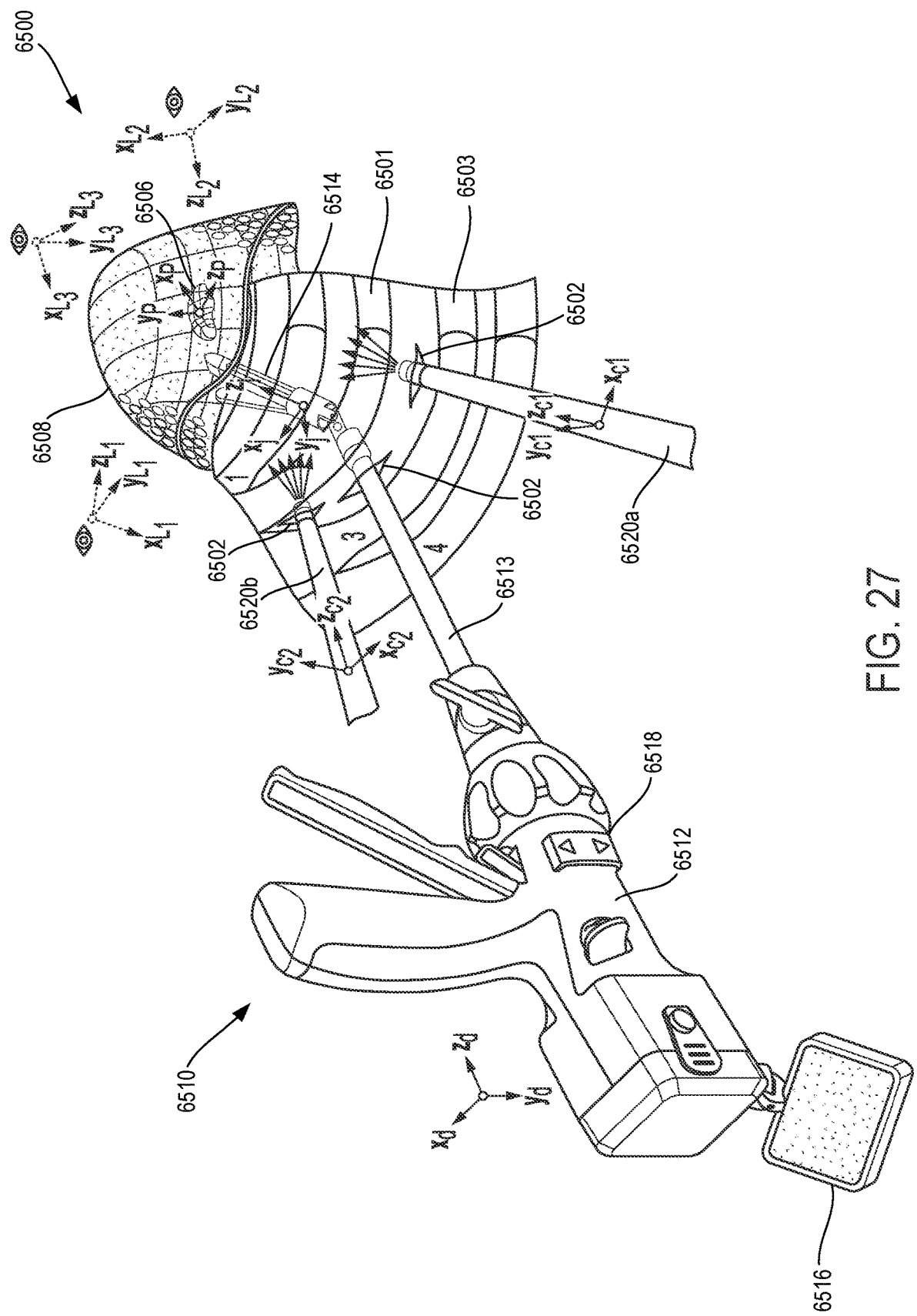

FIG. 27 is a diagram of various coordinate systems associated with a VATS procedure, in accordance with at least one aspect of the present disclosure.

Figure 28:
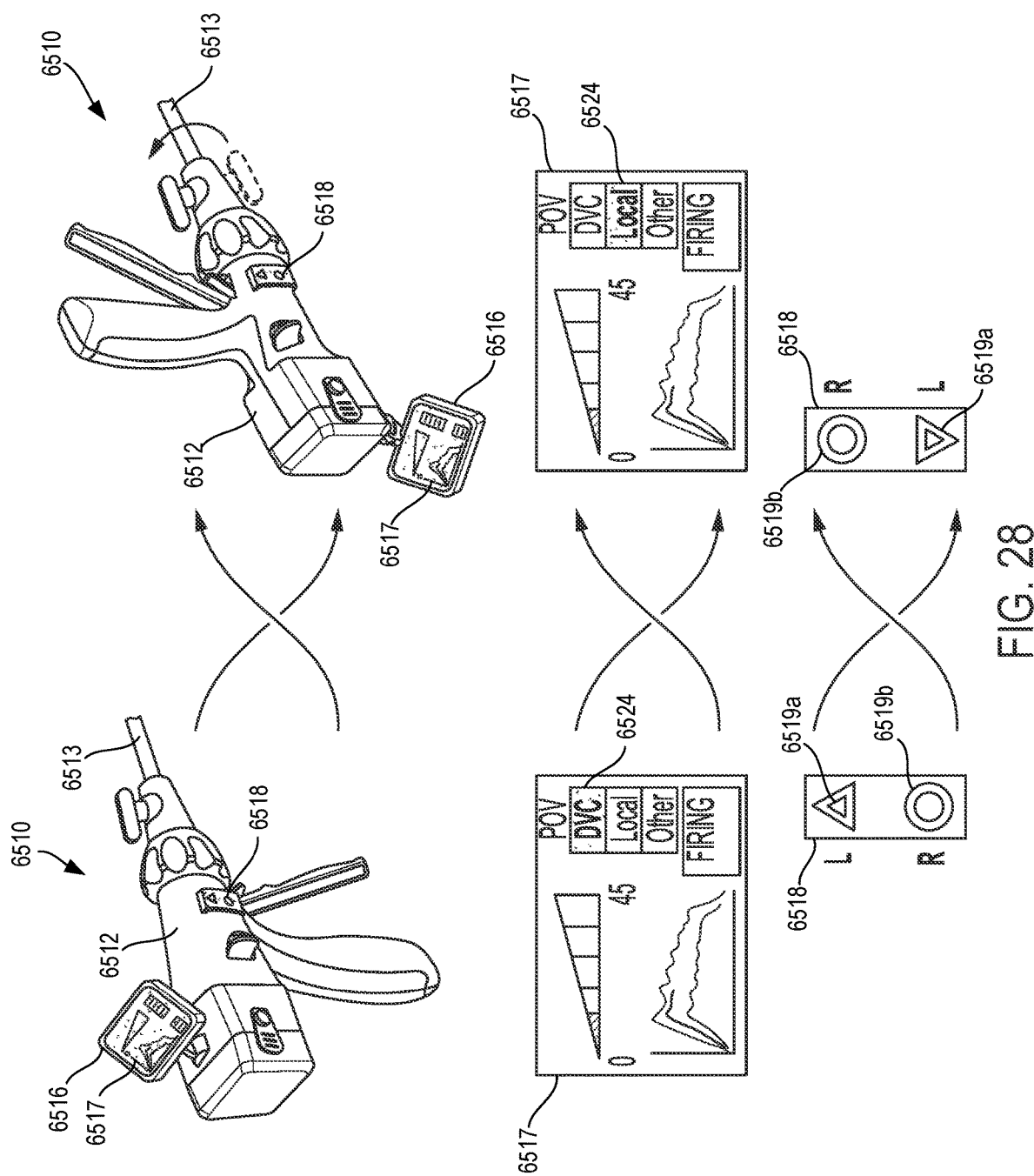

FIG. 28 is a diagram depicting the change in orientation of a display and user controls in response to a change in orientation of the surgical instrument, in accordance with at least one aspect of the present disclosure.

Figure 29:
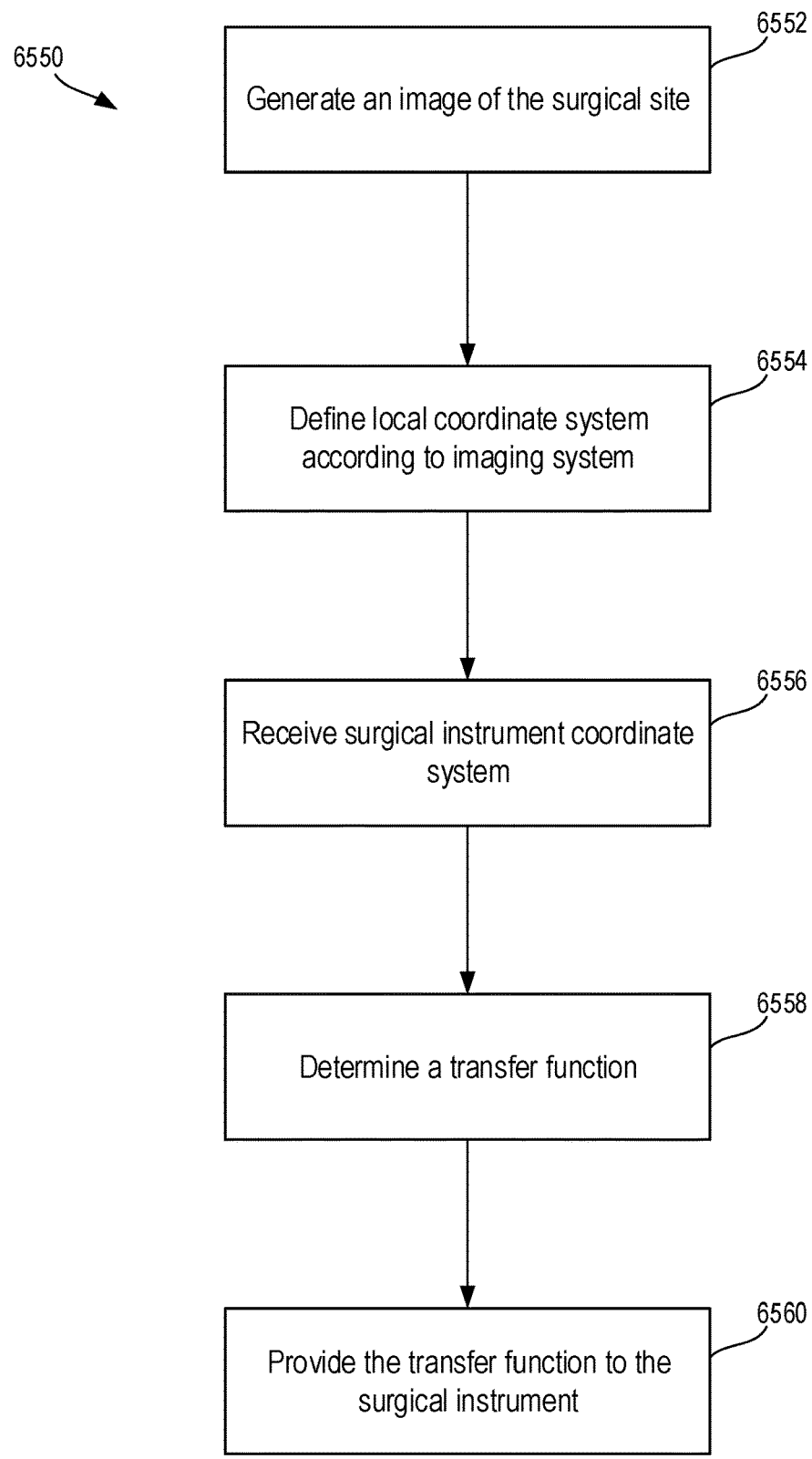

FIG. 29 is a logic flow diagram of a process of adjusting a display and/or user control according to a displayed coordinate system, in accordance with at least one aspect of the present disclosure.

Figure 30:
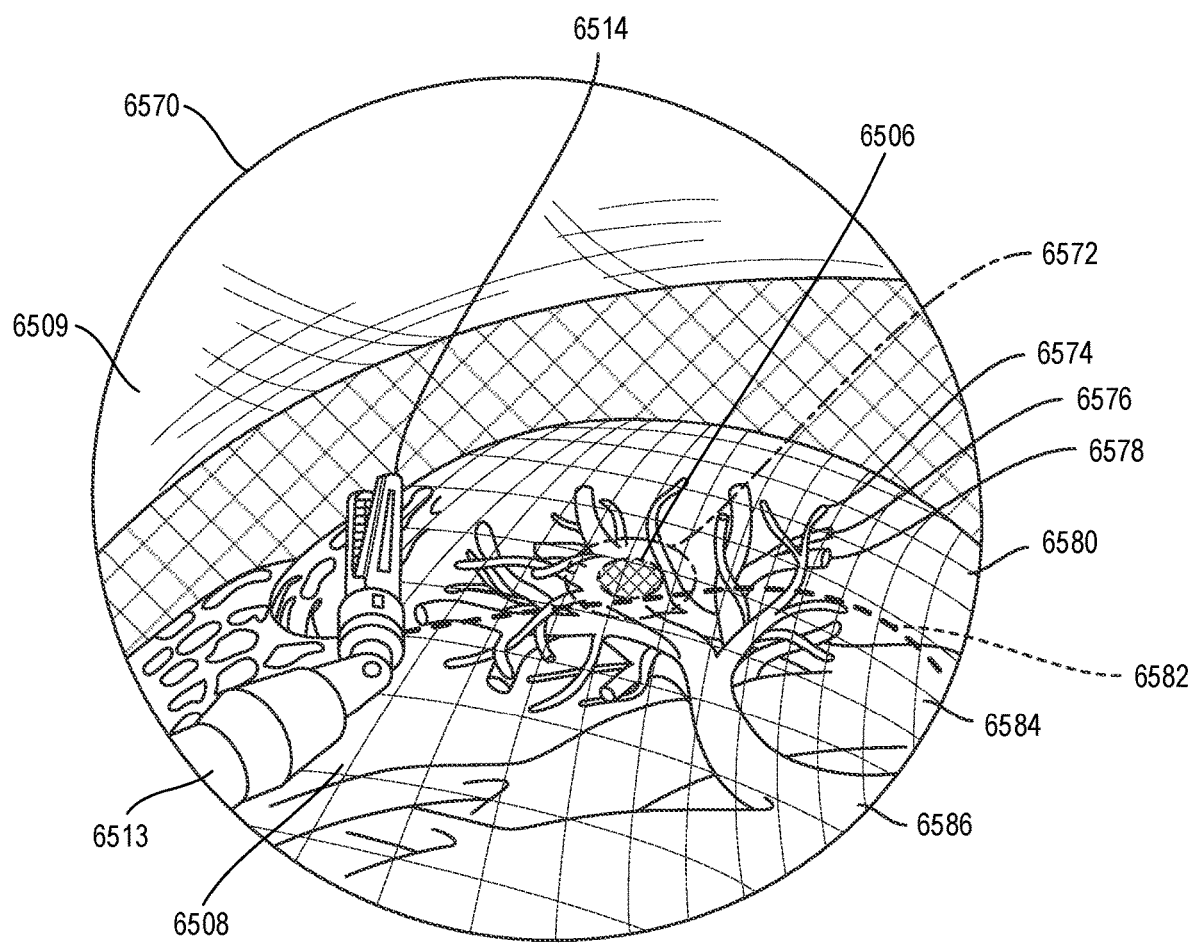

FIG. 30 depicts a camera view of the surgical procedure of FIG. 27, in accordance with at least one aspect of the present disclosure.

Figure 31:
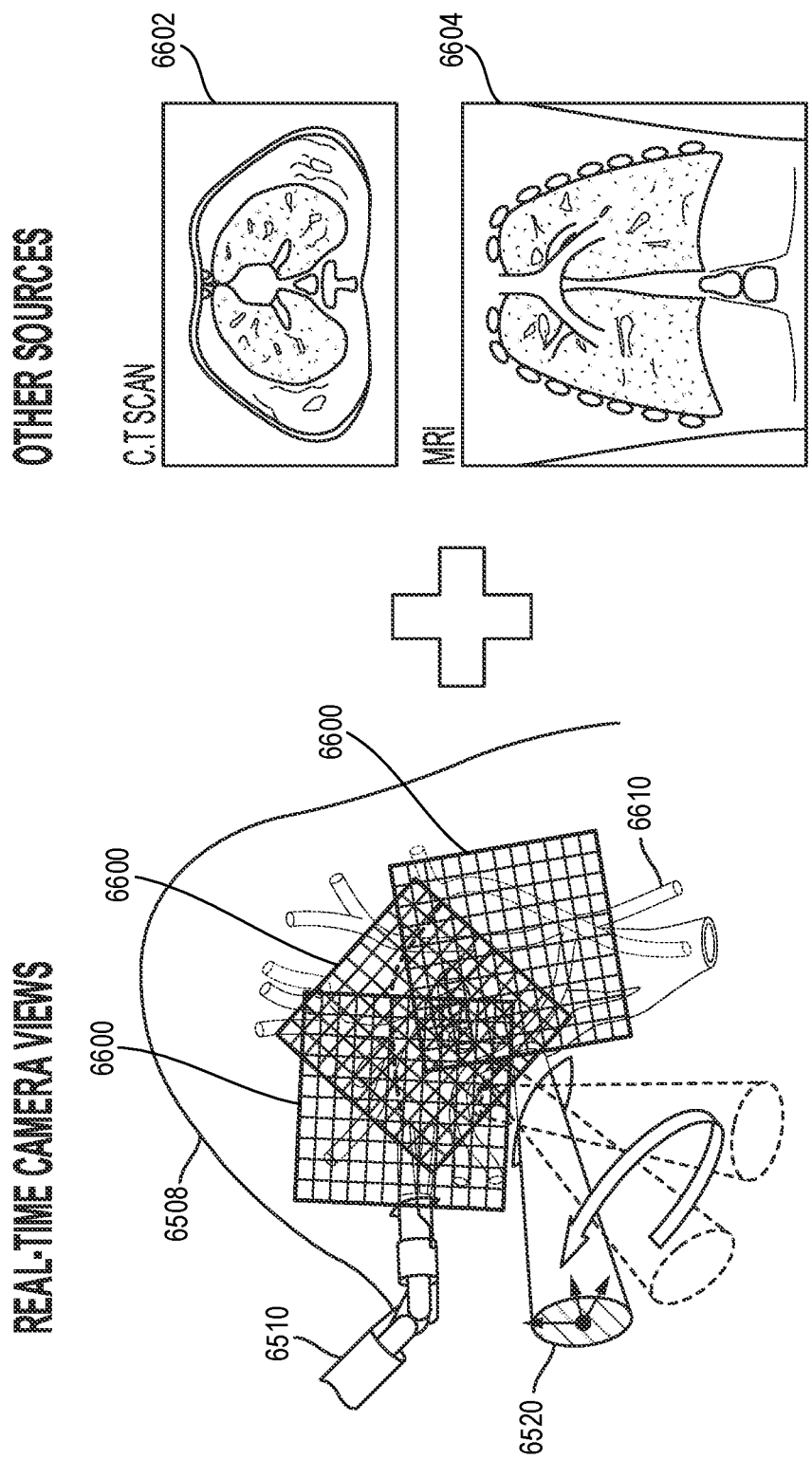

FIG. 31 is a diagram of image sources from which a three-dimensional (3D) representation of a surgical site can be generated, in accordance with at least one aspect of the present disclosure.

Figure 32:
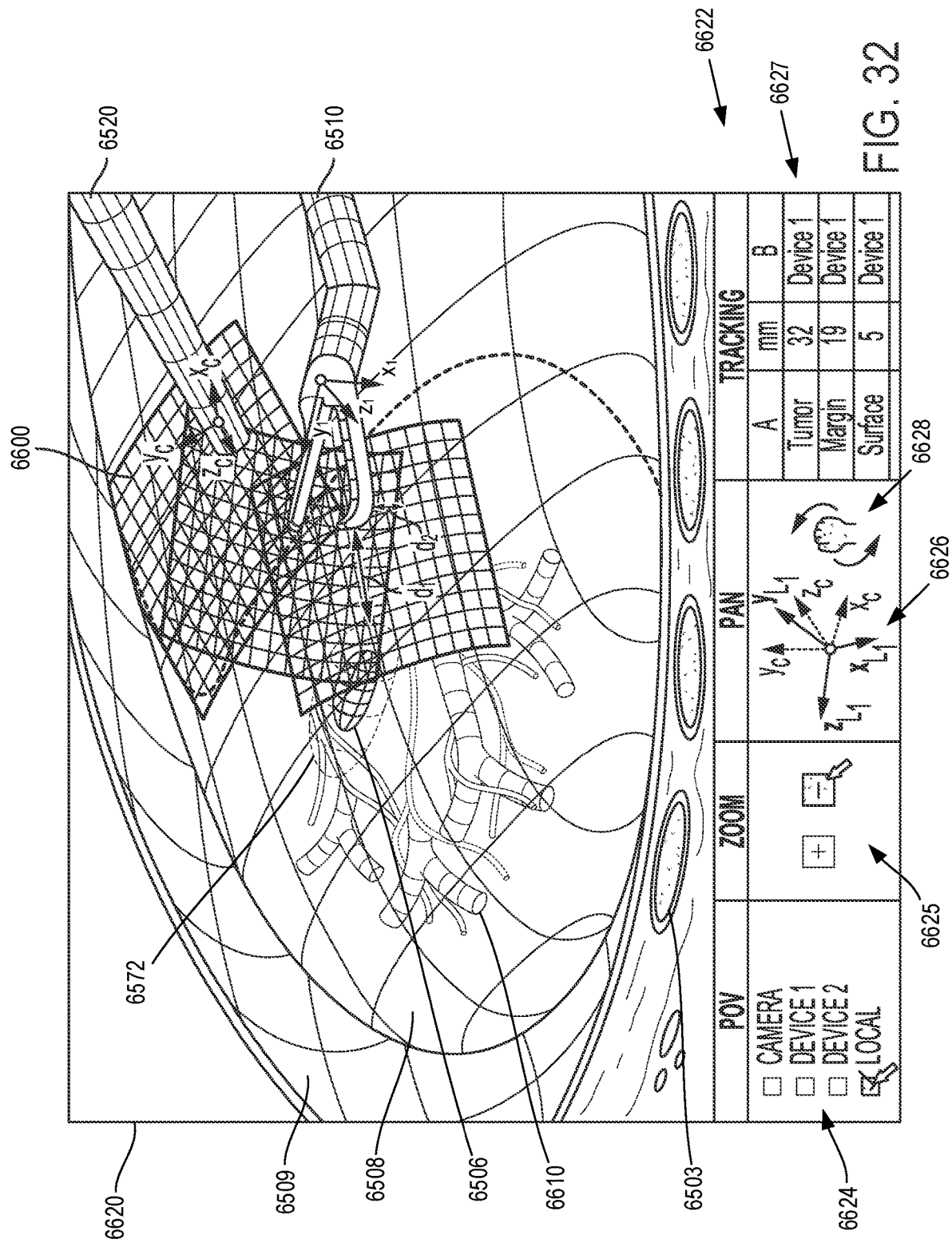

FIG. 32 is a visualization display and graphical user interface (GUI) of the surgical procedure of FIG. 27 provided by an imaging system, in accordance with at least one aspect of the present disclosure.

Figure 33:
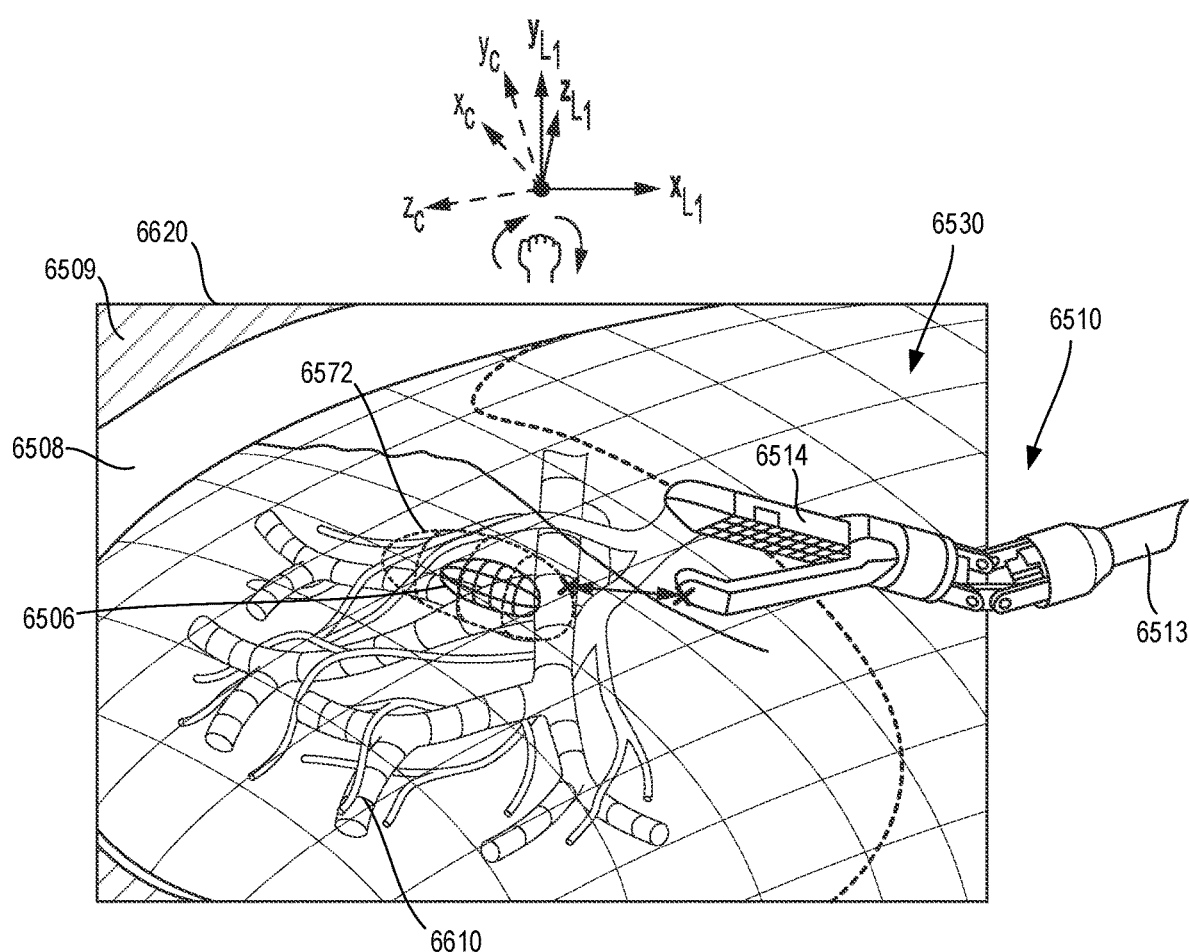

FIG. 33 is the visualization display of FIG. 32 adjusted to a first point of view (POV), in accordance with at least one aspect of the present disclosure.

Figure 34:
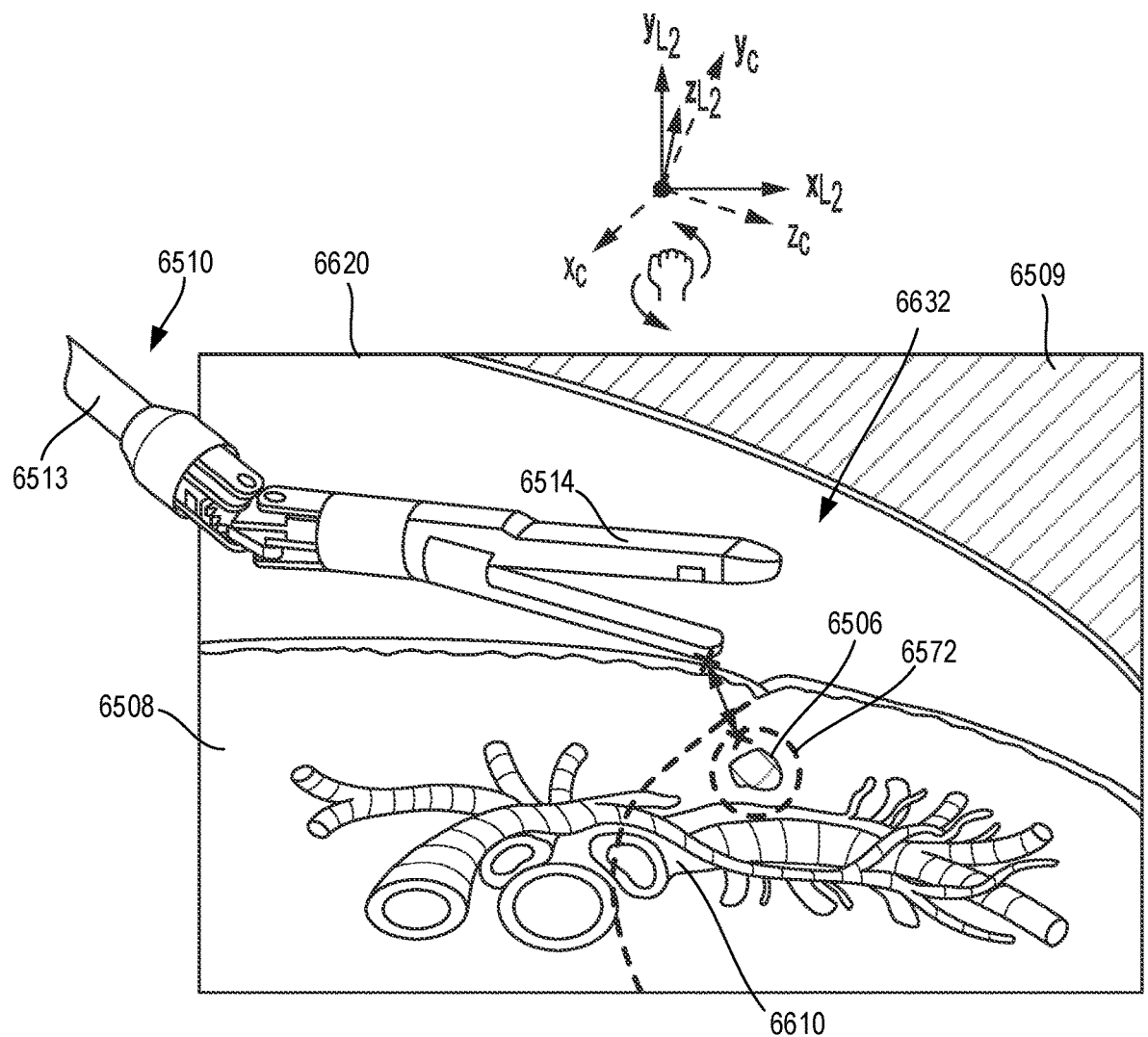

FIG. 34 is the visualization display of FIG. 32 adjusted to a second POV, in accordance with at least one aspect of the present disclosure.

Figure 35:
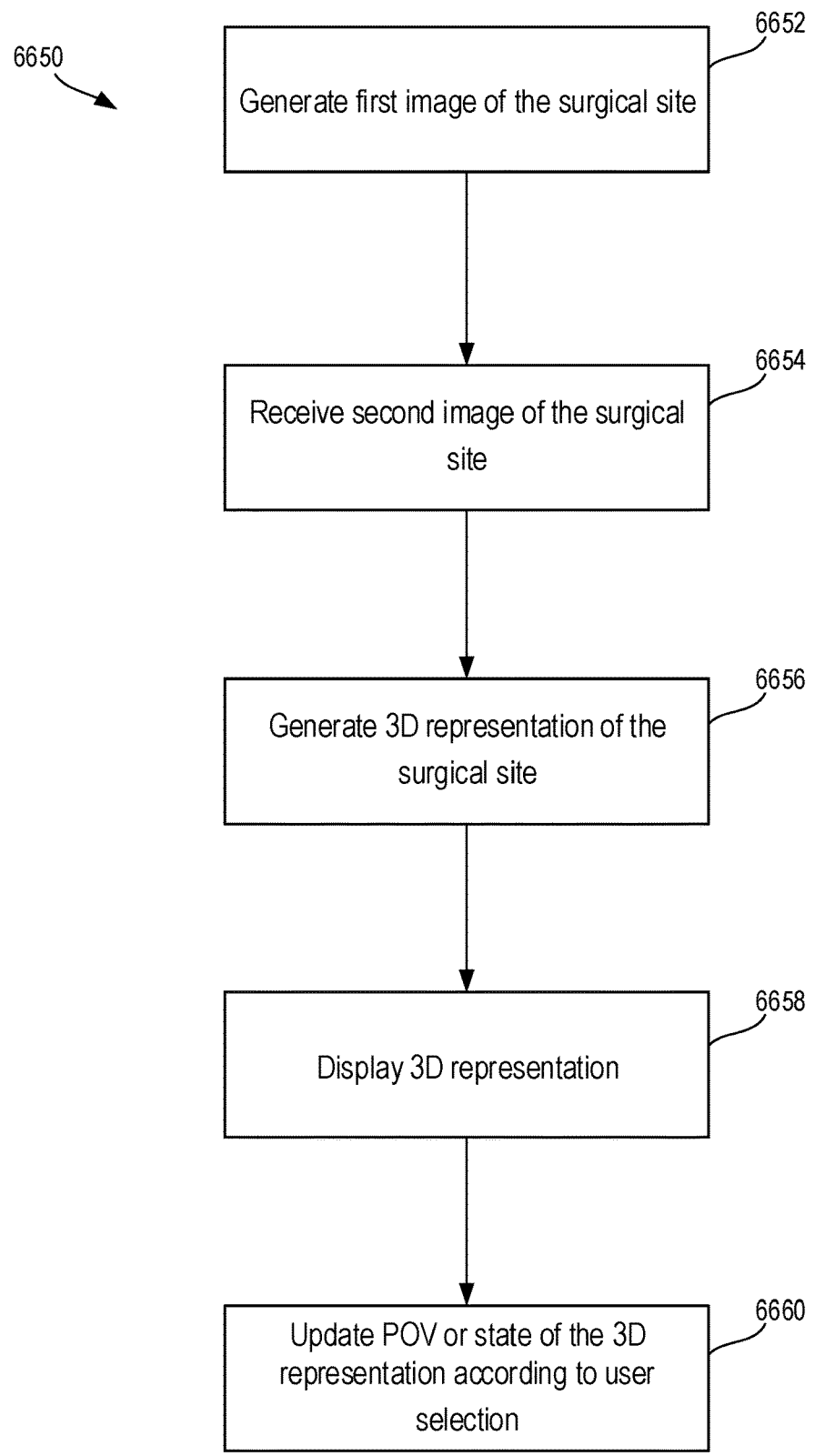

FIG. 35 is a logic flow diagram of a process of controlling a visualization display, in accordance with at least one aspect of the present disclosure.

Figure 36:
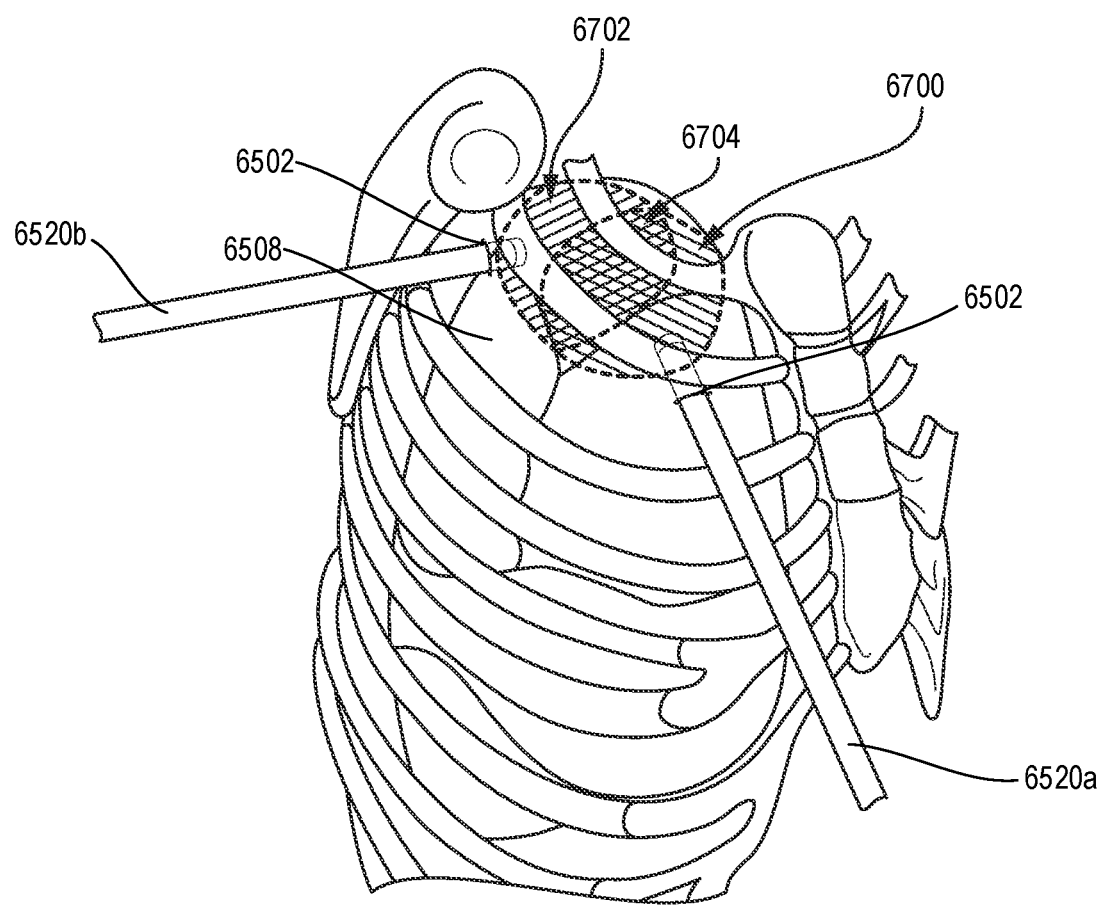

FIG. 36 is a diagram of a VATS procedure utilizing two cameras, in accordance with at least one aspect of the present disclosure.

Figure 37:
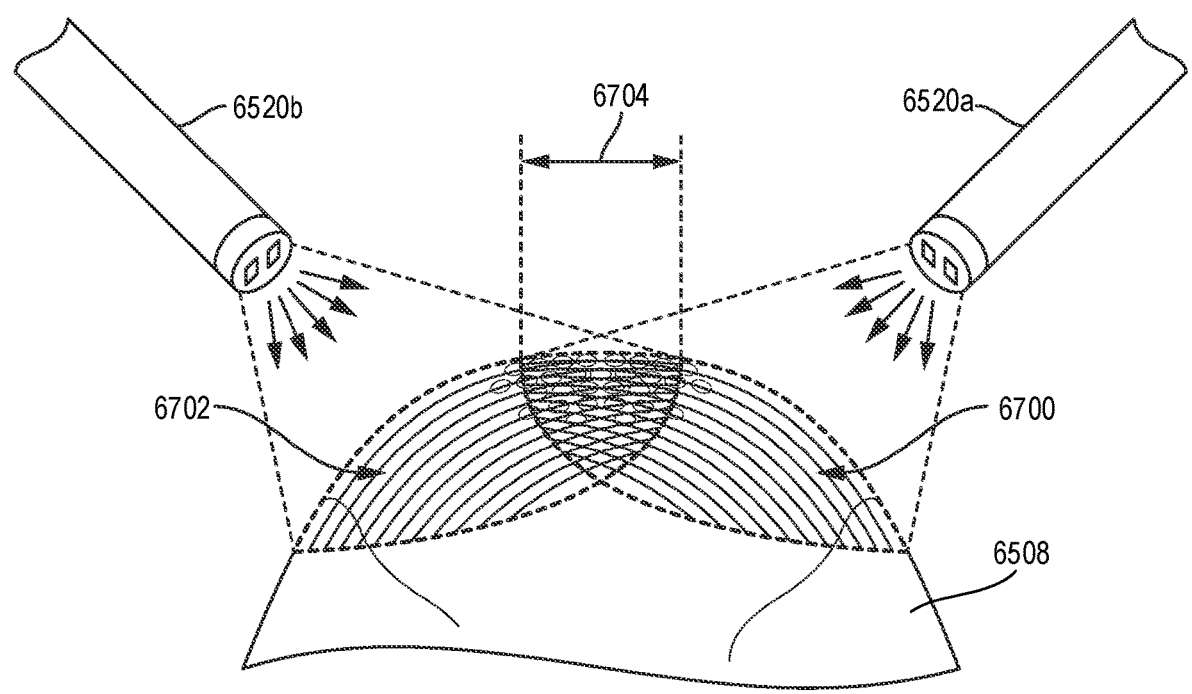

FIG. 37 is a diagram of a lung being imaged during the VATS procedure of FIG. 36, in accordance with at least one aspect of the present disclosure.

Figure 38:
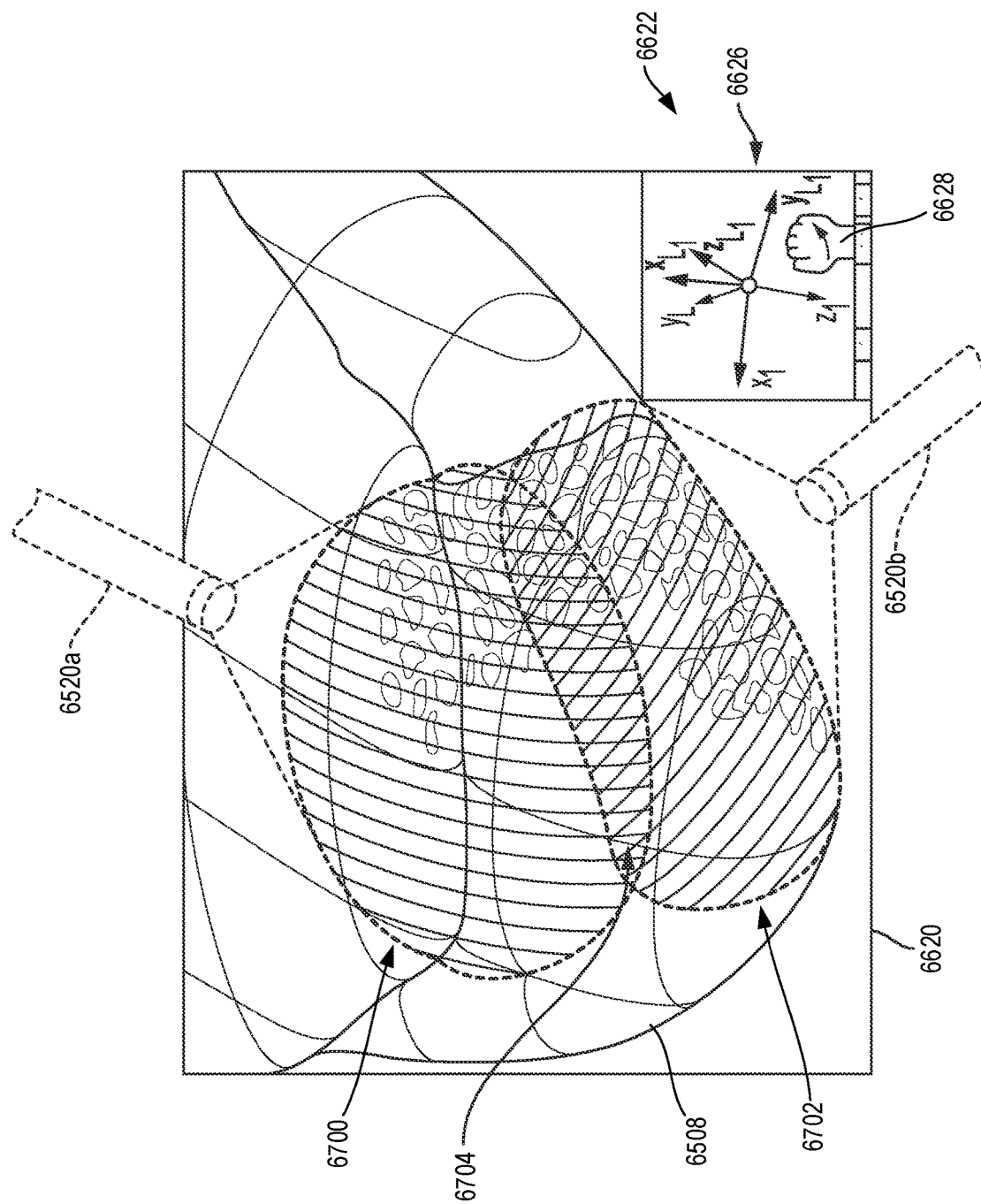

FIG. 38 is a visualization display and GUI of the VATS procedure of FIGS. 36 and 37, in accordance with at least one aspect of the present disclosure.

Figure 39:
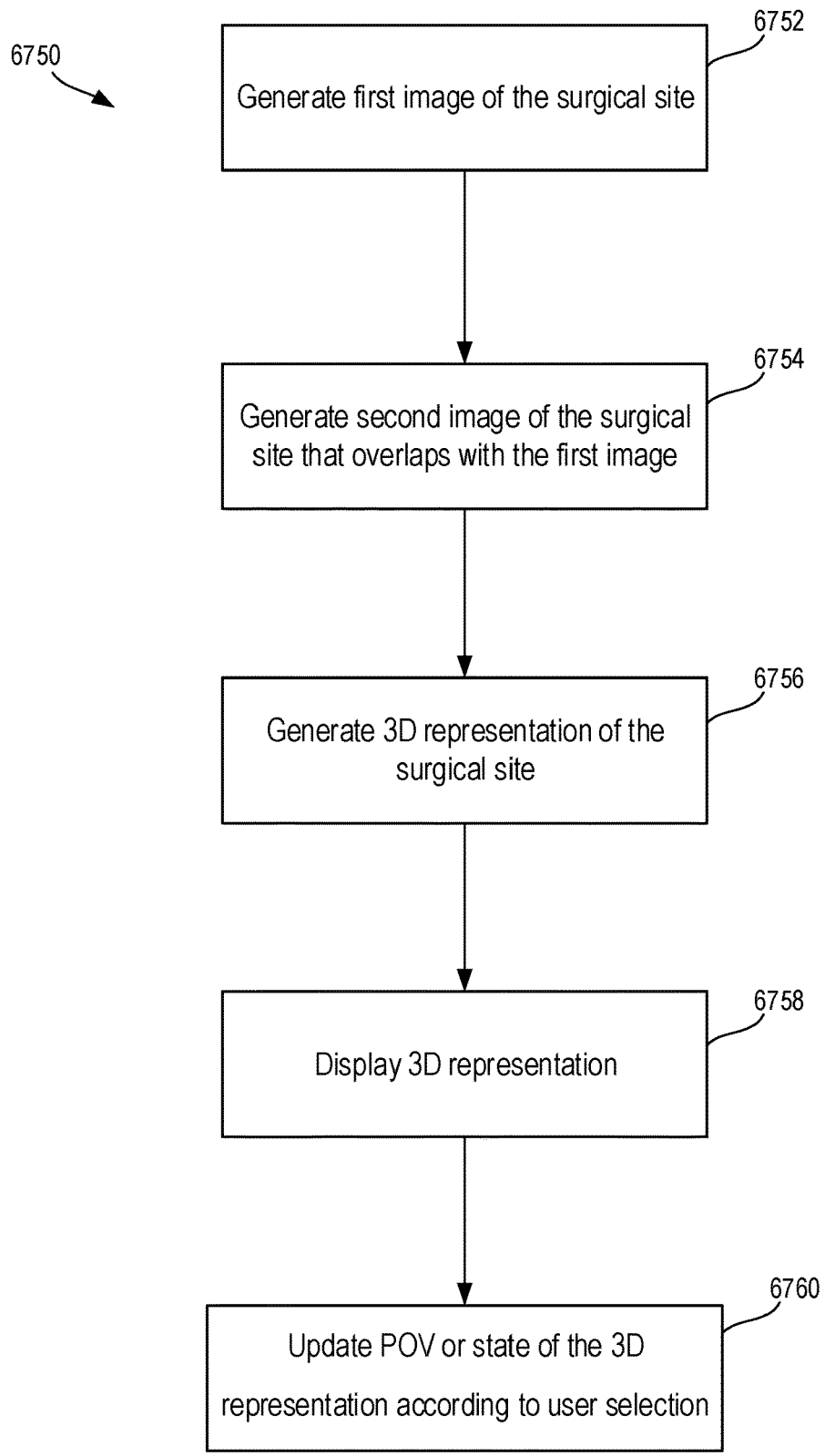

FIG. 39 is a logic flow diagram of a process of controlling a visualization display, in accordance with at least one aspect of the present disclosure.

Figure 40:
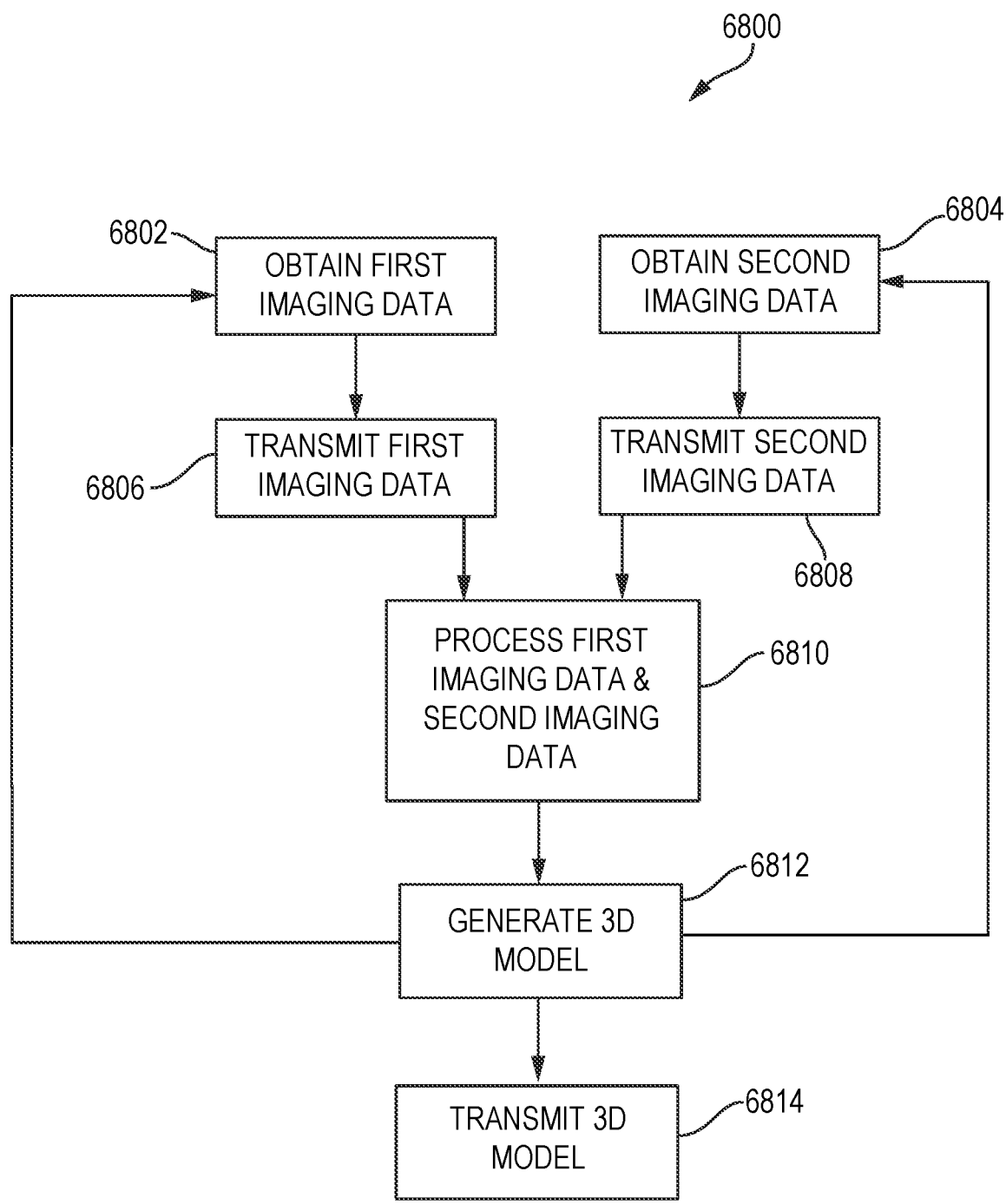

FIG. 40 is a logic flow diagram of a process of conveying three-dimensional models to a clinician, in accordance with at least one aspect of the present disclosure.

DESCRIPTION

Applicant of the present application owns the following U.S. patent applications, filed Dec. 30, 2019, each of which is herein incorporated by reference in its entirety:

U.S. patent application Ser. No. 16/729,807, titled METHOD OF USING IMAGING DEVICES IN SURGERY;

U.S. patent application Ser. No. 16/729,803, titled ADAPTIVE VISUALIZATION BY A SURGICAL SYSTEM;

U.S. patent application Ser. No. 16/729,790, titled SURGICAL SYSTEM CONTROL BASED ON MULTIPLE SENSED PARAMETERS;

U.S. patent application Ser. No. 16/729,796, titled ADAPTIVE SURGICAL SYSTEM CONTROL ACCORDING TO SURGICAL SMOKE PARTICLE CHARACTERISTICS;

U.S. patent application Ser. No. 16/729,737, titled ADAPTIVE SURGICAL SYSTEM CONTROL ACCORDING TO SURGICAL SMOKE CLOUD CHARACTERISTICS;

U.S. patent application Ser. No. 16/729,740, titled SURGICAL SYSTEMS CORRELATING VISUALIZATION DATA AND POWERED SURGICAL INSTRUMENT DATA;

U.S. patent application Ser. No. 16/729,751, titled SURGICAL SYSTEMS FOR GENERATING THREE DIMENSIONAL CONSTRUCTS OF ANATOMICAL ORGANS AND COUPLING IDENTIFIED;

U.S. patent application Ser. No. 16/729,735, titled SURGICAL SYSTEM FOR OVERLAYING SURGICAL INSTRUMENT DATA ONTO A VIRTUAL THREE DIMENSIONAL CONSTRUCT OF AN ORGAN;

U.S. patent application Ser. No. 16/729,729, titled SURGICAL SYSTEMS FOR PROPOSING AND CORROBORATING ORGAN PORTION REMOVALS;

U.S. patent application Ser. No. 16/729,778, titled SYSTEM AND METHOD FOR DETERMINING, ADJUSTING, AND MANAGING RESECTION MARGIN ABOUT A SUBJECT TISSUE;

U.S. patent application Ser. No. 16/729,747, titled DYNAMIC SURGICAL VISUALIZATION SYSTEMS; and U.S. patent application Ser. No. 16/729,772, titled ANALYZING SURGICAL TRENDS BY A SURGICAL SYSTEM.

Applicant of the present application owns the following U.S. patent applications, filed on Mar. 15, 2019, each of which is herein incorporated by reference in its entirety:

U.S. patent application Ser. No. 16/354,417, titled INPUT CONTROLS FOR ROBOTIC SURGERY, now U.S. Patent Application Publication No. 2020/0289219;

U.S. patent application Ser. No. 16/354,420, titled DUAL MODE CONTROLS FOR ROBOTIC SURGERY, now U.S. Patent Application Publication No. 2020/0289228;

U.S. patent application Ser. No. 16/354,422, titled MOTION CAPTURE CONTROLS FOR ROBOTIC SURGERY, now U.S. Patent Application Publication No. 2020/0289216;

U.S. patent application Ser. No. 16/354,440, titled ROBOTIC SURGICAL SYSTEMS WITH MECHANISMS FOR SCALING SURGICAL TOOL MOTION ACCORDING TO TISSUE PROXIMITY, now U.S. Patent Application Publication No. 2020/0289220;

U.S. patent application Ser. No. 16/354,444, titled ROBOTIC SURGICAL SYSTEMS WITH MECHANISMS FOR SCALING CAMERA MAGNIFICATION ACCORDING TO PROXIMITY OF SURGICAL TOOL TO TISSUE, now U.S. Patent Application Publication No. 2020/0289205;

U.S. patent application Ser. No. 16/354,454, titled ROBOTIC SURGICAL SYSTEMS WITH SELECTIVELY LOCKABLE END EFFECTORS, now U.S. Patent Application Publication No. 2020/0289221;

U.S. patent application Ser. No. 16/354,461, titled SELECTABLE VARIABLE RESPONSE OF SHAFT MOTION OF SURGICAL ROBOTIC SYSTEMS, now U.S. Patent Application Publication No. 2020/0289222;

U.S. patent application Ser. No. 16/354,470, titled SEGMENTED CONTROL INPUTS FOR SURGICAL ROBOTIC SYSTEMS, now U.S. Patent Application Publication No. 2020/0289223;

U.S. patent application Ser. No. 16/354,474, titled ROBOTIC SURGICAL CONTROLS HAVING FEEDBACK CAPABILITIES, now U.S. Patent Application Publication No. 2020/0289229;

U.S. patent application Ser. No. 16/354,478, titled ROBOTIC SURGICAL CONTROLS WITH FORCE FEEDBACK, now U.S. Patent Application Publication No. 2020/0289230; and U.S. patent application Ser. No. 16/354,481, titled JAW COORDINATION OF ROBOTIC SURGICAL CONTROLS, now U.S. Patent Application Publication No. 2020/0289217.

Applicant of the present application also owns the following U.S. patent applications, filed on Sep. 11, 2018, each of which is herein incorporated by reference in its entirety:

U.S. patent application Ser. No. 16/128,179, titled SURGICAL VISUALIZATION PLATFORM, now U.S. Patent Application Publication No. 2020/0015923;

U.S. patent application Ser. No. 16/128,180, titled CONTROLLING AN EMITTER ASSEMBLY PULSE SEQUENCE, now U.S. Patent Application Publication No. 2020/0015900;

U.S. patent application Ser. No. 16/128,198, titled SINGULAR EMR SOURCE EMITTER ASSEMBLY, now U.S. Patent Application Publication No. 2020/0015668;

U.S. patent application Ser. No. 16/128,207, titled COMBINATION EMITTER AND CAMERA ASSEMBLY, now U.S. Patent Application Publication No. 2020/0015925;

U.S. patent application Ser. No. 16/128,176, titled SURGICAL VISUALIZATION WITH PROXIMITY TRACKING FEATURES, now U.S. Patent Application Publication No. 2020/0015899;

U.S. patent application Ser. No. 16/128,187, titled SURGICAL VISUALIZATION OF MULTIPLE TARGETS, now U.S. Patent Application Publication No. 2020/0015903;

U.S. patent application Ser. No. 16/128,192, titled VISUALIZATION OF SURGICAL DEVICES, now U.S. Pat. No. 10,792,034;

U.S. patent application Ser. No. 16/128,163, titled OPERATIVE COMMUNICATION OF LIGHT, now U.S. Patent Application Publication No. 2020/0015897;

U.S. patent application Ser. No. 16/128,197, titled ROBOTIC LIGHT PROJECTION TOOLS, now U.S. Patent Application Publication No. 2020/0015924;

U.S. patent application Ser. No. 16/128,164, titled SURGICAL VISUALIZATION FEEDBACK SYSTEM, now U.S. Patent Application Publication No. 2020/0015898;

U.S. patent application Ser. No. 16/128,193, titled SURGICAL VISUALIZATION AND MONITORING, now U.S. Patent Application Publication No. 2020/0015906;

U.S. patent application Ser. No. 16/128,195, titled INTEGRATION OF IMAGING DATA, now U.S. Patent Application Publication No. 2020/0015907;

U.S. patent application Ser. No. 16/128,170, titled ROBOTICALLY-ASSISTED SURGICAL SUTURING SYSTEMS, now U.S. Pat. No. 10,925,598;

U.S. patent application Ser. No. 16/128,183, titled SAFETY LOGIC FOR SURGICAL SUTURING SYSTEMS, now U.S. Patent Application Publication No. 2020/0015901;

U.S. patent application Ser. No. 16/128,172, titled ROBOTIC SYSTEM WITH SEPARATE PHOTOACOUSTIC RECEIVER, now U.S. Patent Application Publication No. 2020/0015914; and U.S. patent application Ser. No. 16/128,185, titled FORCE SENSOR THROUGH STRUCTURED LIGHT DEFLECTION, now U.S. Patent Application Publication No. 2020/0015902.

Applicant of the present application also owns the following U.S. patent applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, now U.S. Patent Application Publication No. 2019/0201111;

U.S. patent application Ser. No. 15/940,676, titled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,711, titled SENSING ARRANGEMENTS FOR ROBOT-ASSISTED SURGICAL PLATFORMS, now U.S. Patent Application Publication No. 2019/0201120; and U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No. 2019/0200905.

Applicant of the present application owns the following U.S. patent applications, filed on Dec. 4, 2018, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Surgical Visualization System

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein.

Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. It should be noted that throughout the following disclosure, any reference to "light," unless specifically in reference to visible light, can include electromagnetic radiation (EMR) or photons in the visible and/or non-visible portions of the EMR wavelength spectrum. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
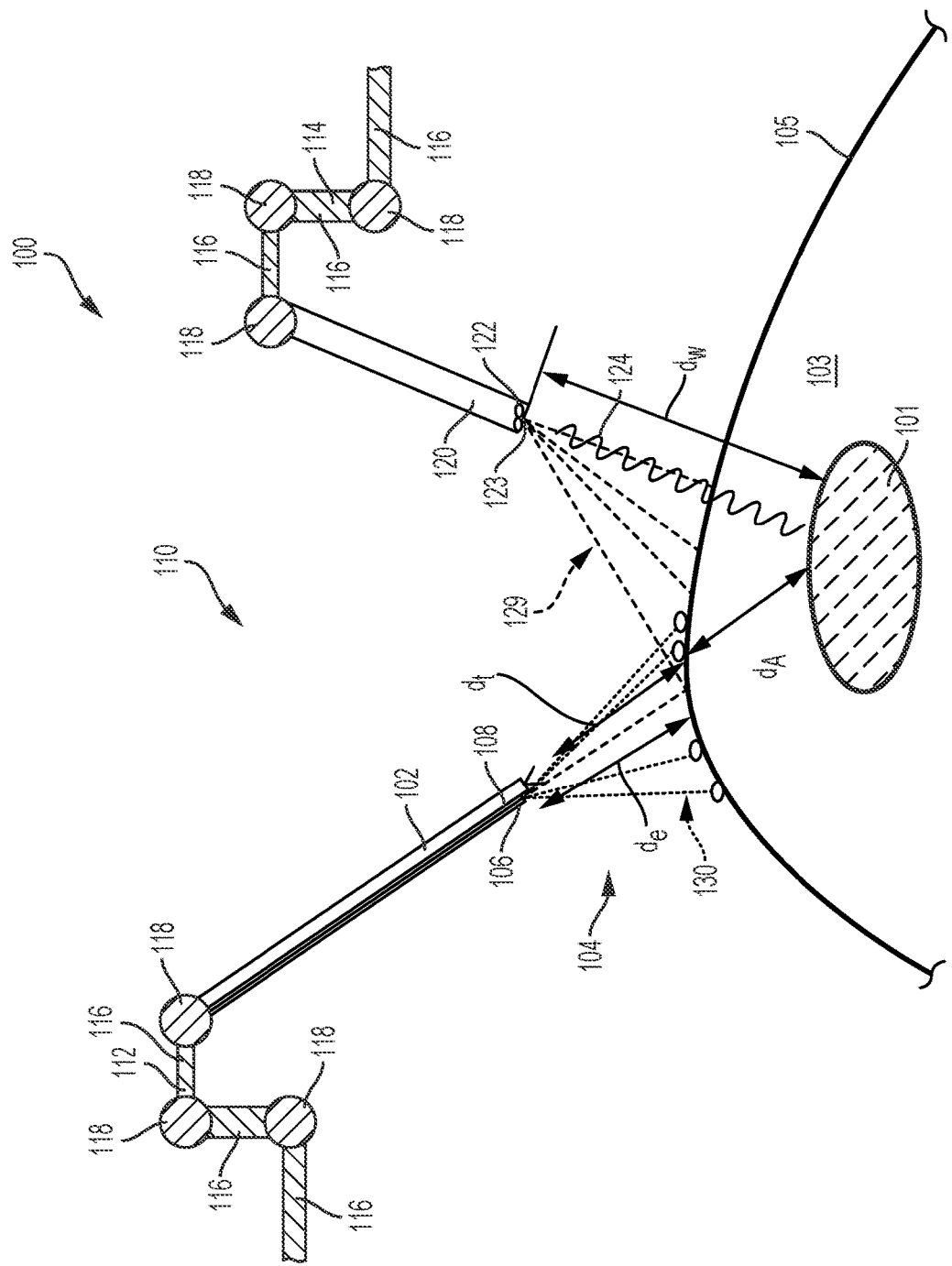
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
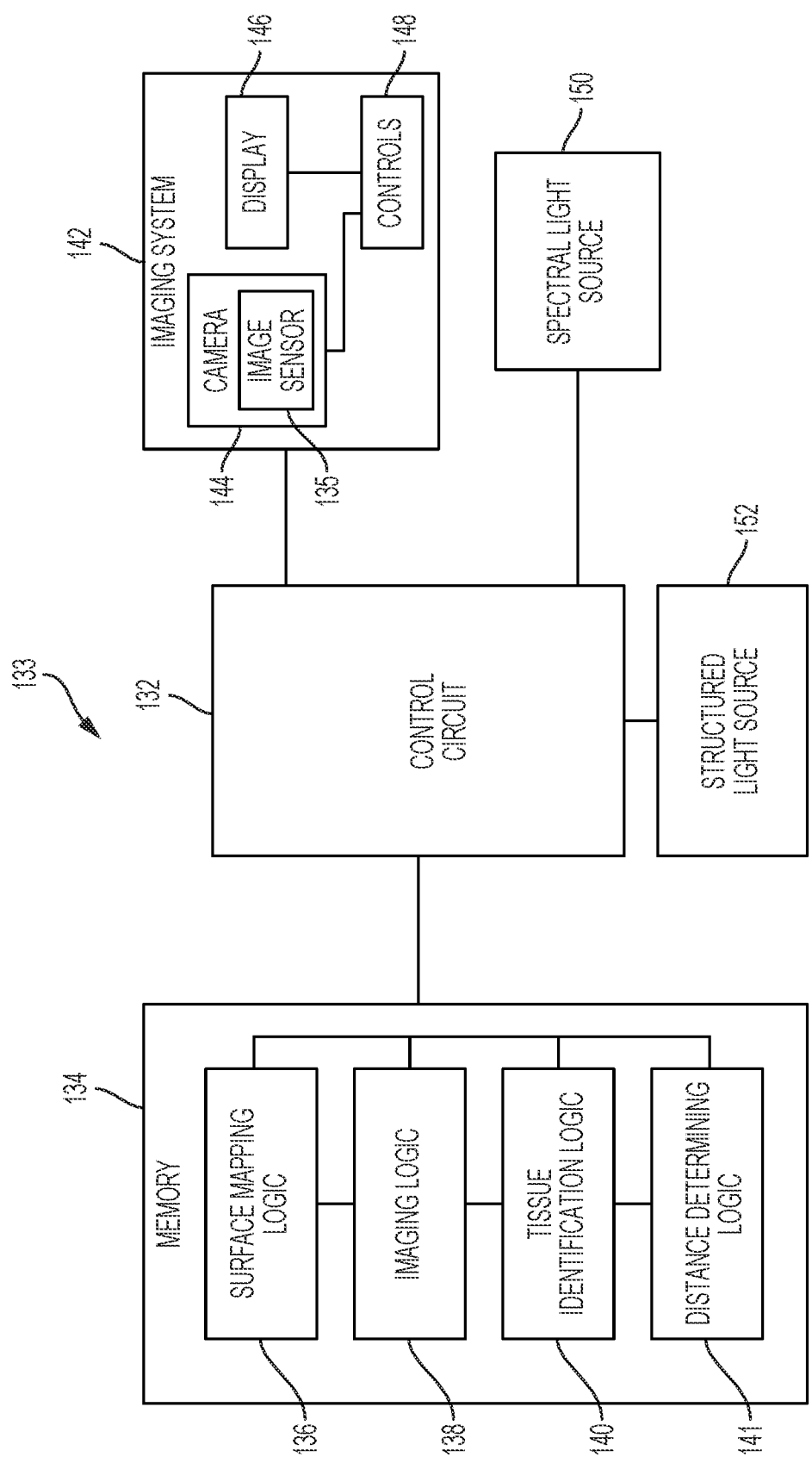
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
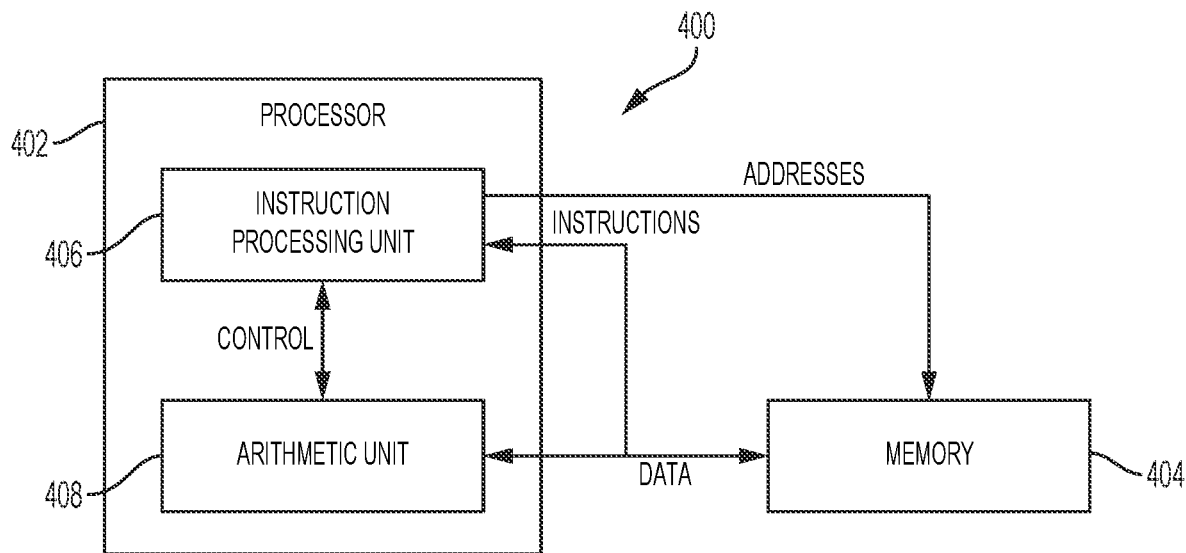
FIG. 2A illustrates a control circuit configured to control aspects of a surgical visualization system, according to at least one aspect of the present disclosure.
Figure 2B:
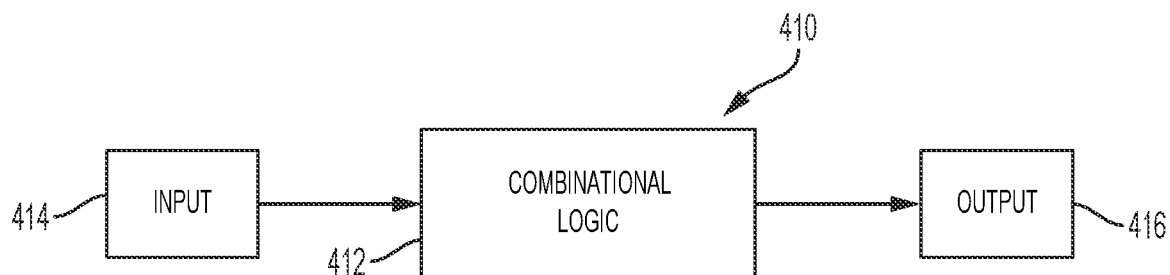
FIG. 2B illustrates a combinational logic circuit configured to control aspects of a surgical visualization system, according to at least one aspect of the present disclosure.
Figure 2C:
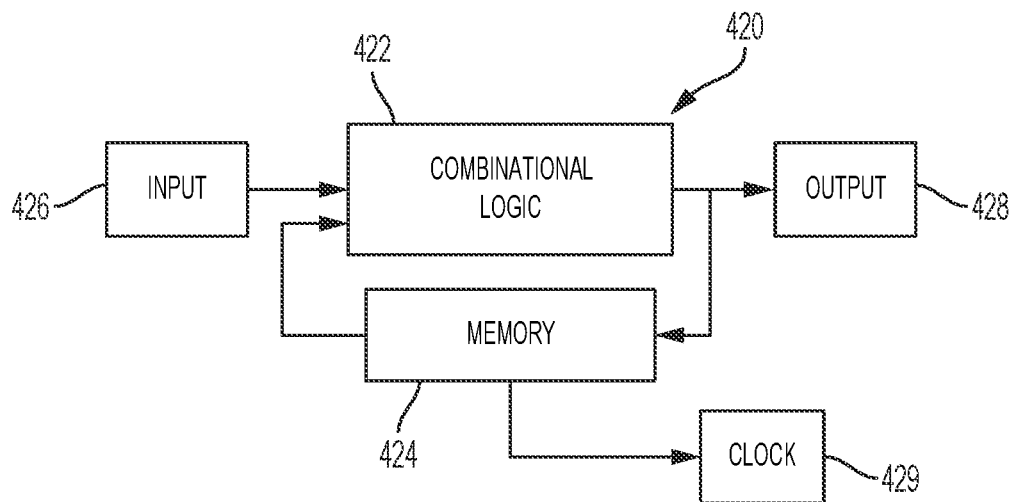
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned U.S. patent applications, including U.S. patent application Ser. No. 16/128,192, titled VISUALIZATION OF SURGICAL DEVICES, filed Sep. 11, 2018, for example, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
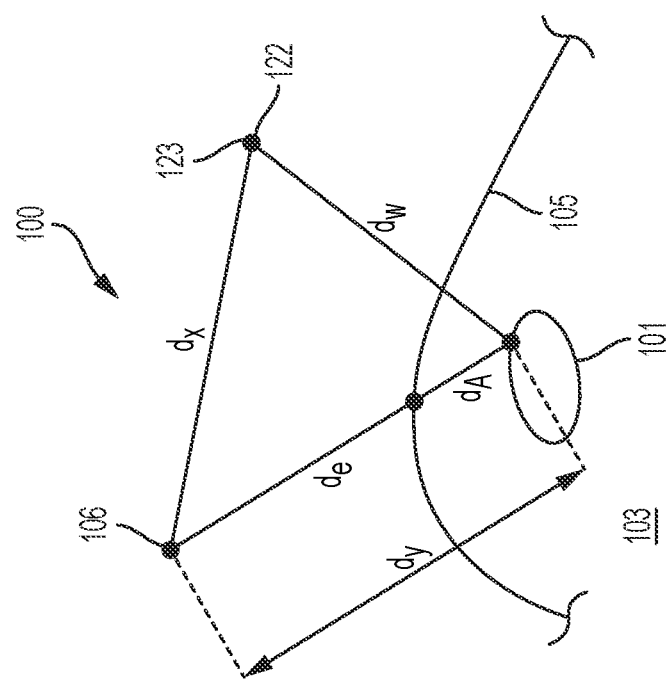
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
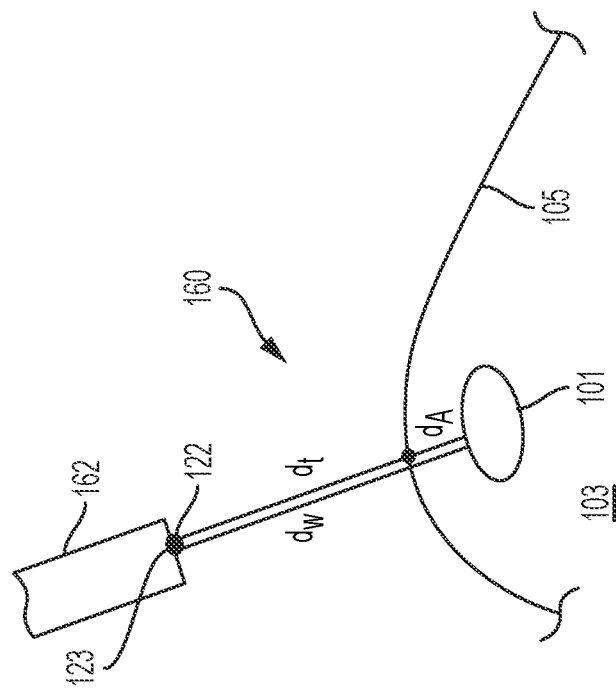
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figures 7A, 7B:
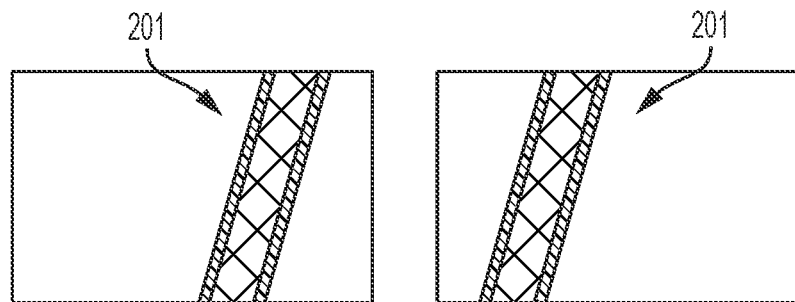
Figure 8:
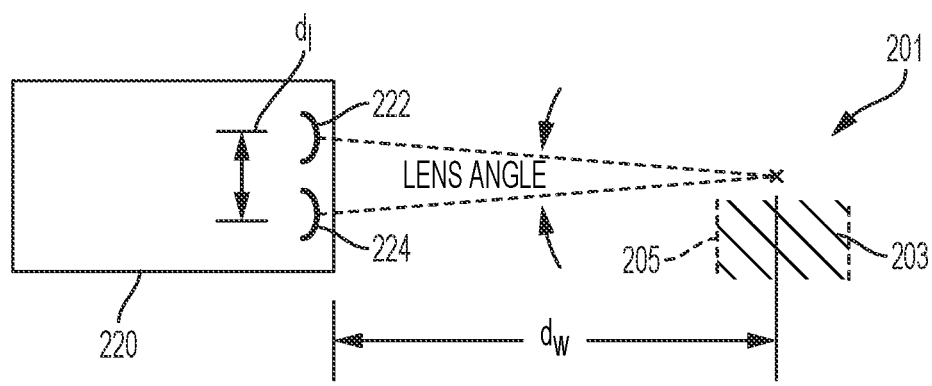
FIG. 8 is a schematic of the surgical visualization system of FIG. 6, in which a camera-to-critical structure distance $d_w$ from the three-dimensional camera to the critical structure can be determined, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
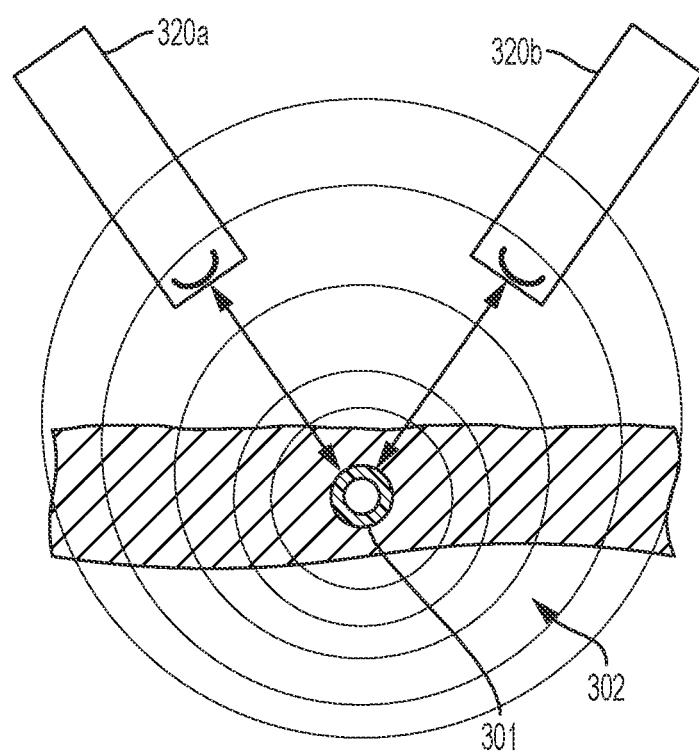
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
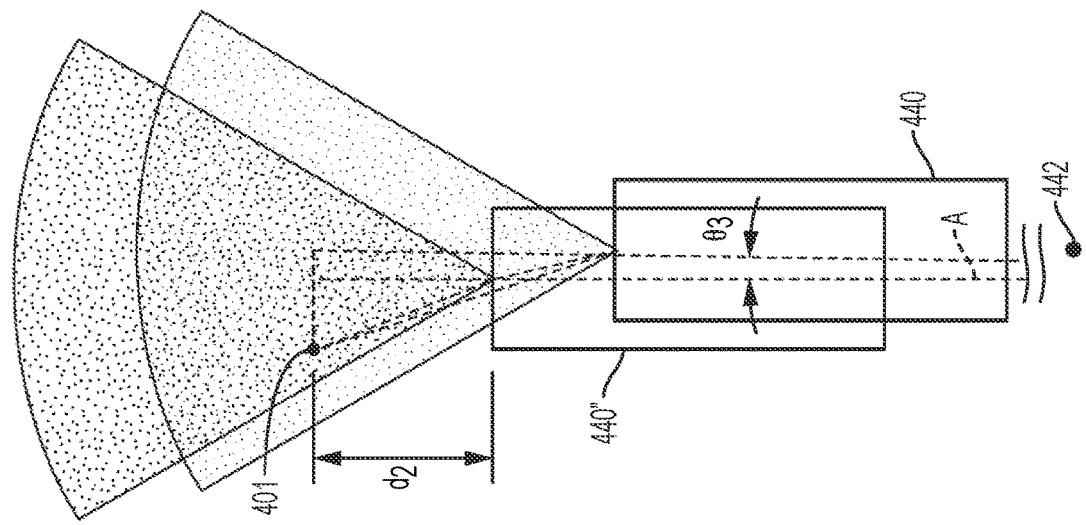
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
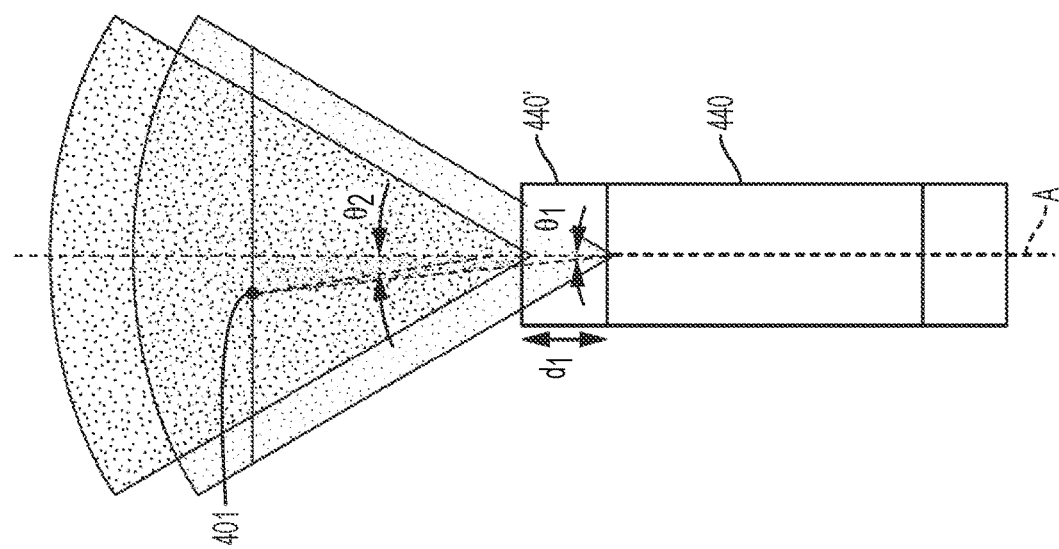
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
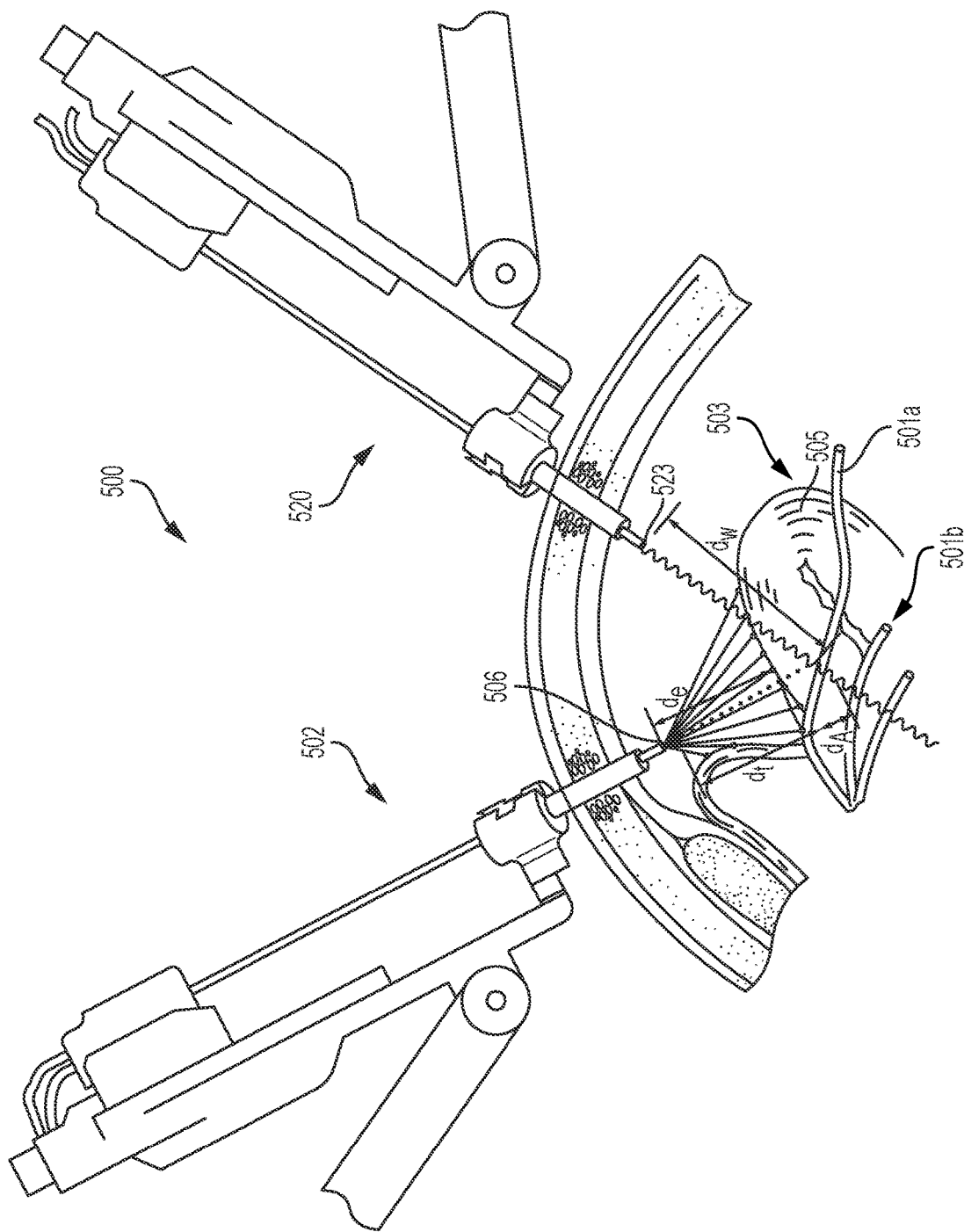
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera-to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
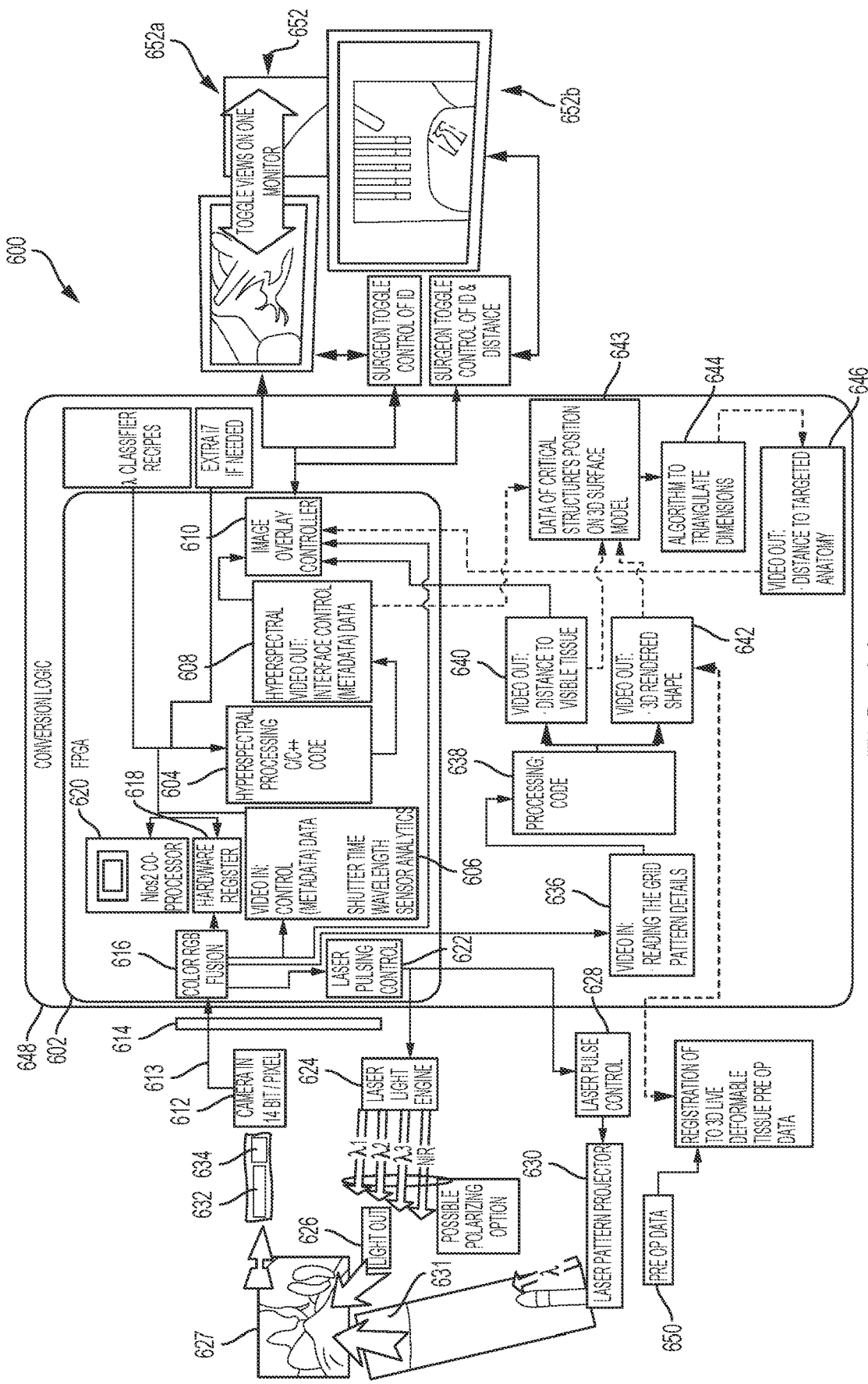
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned U.S. patent applications, including U.S. patent application Ser. No. 16/128,195, titled INTEGRATION OF IMAGING DATA, filed Sep. 11, 2018, now U.S. Patent Application Publication No. 2020/0015907, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
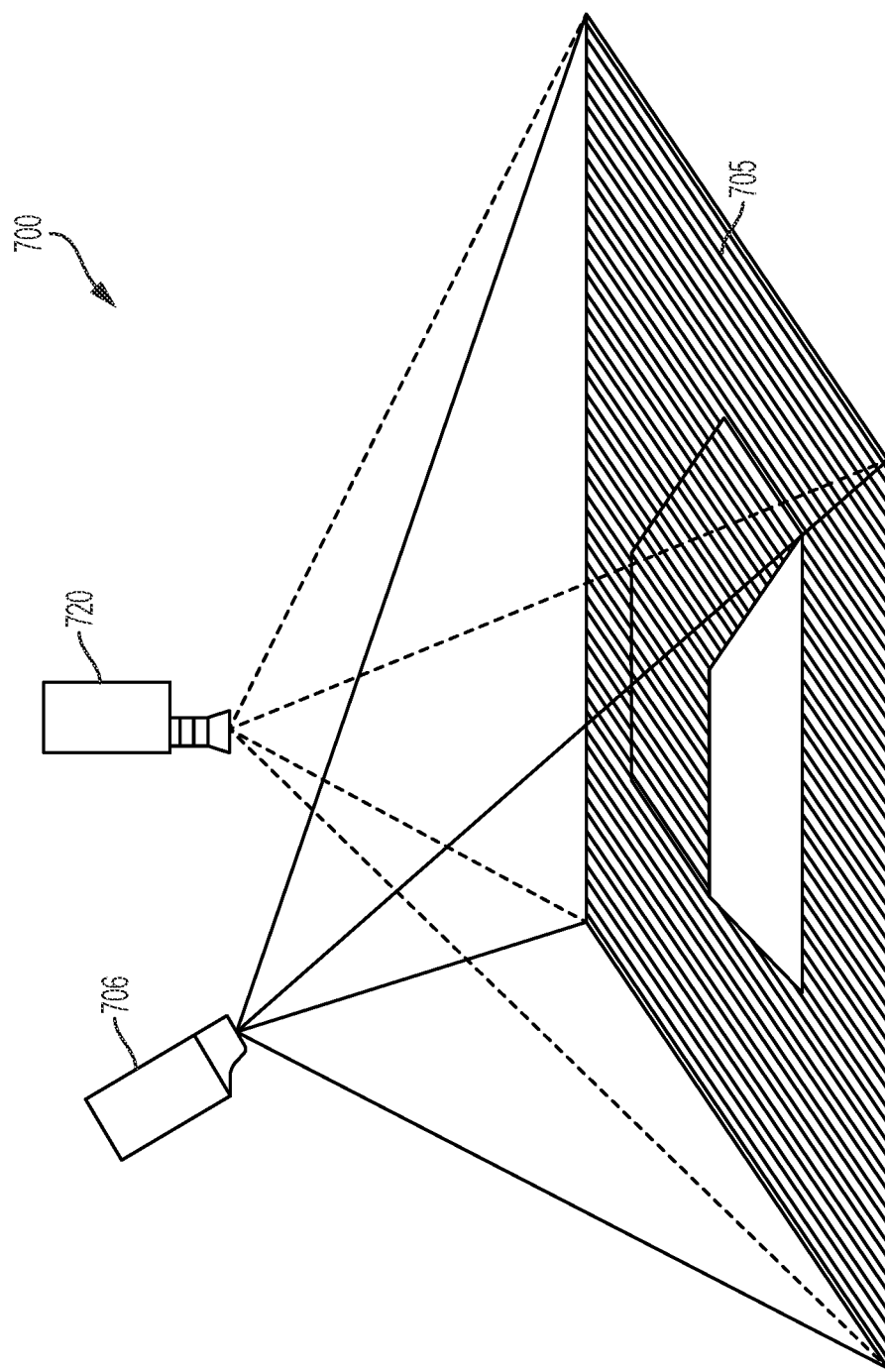
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13A:
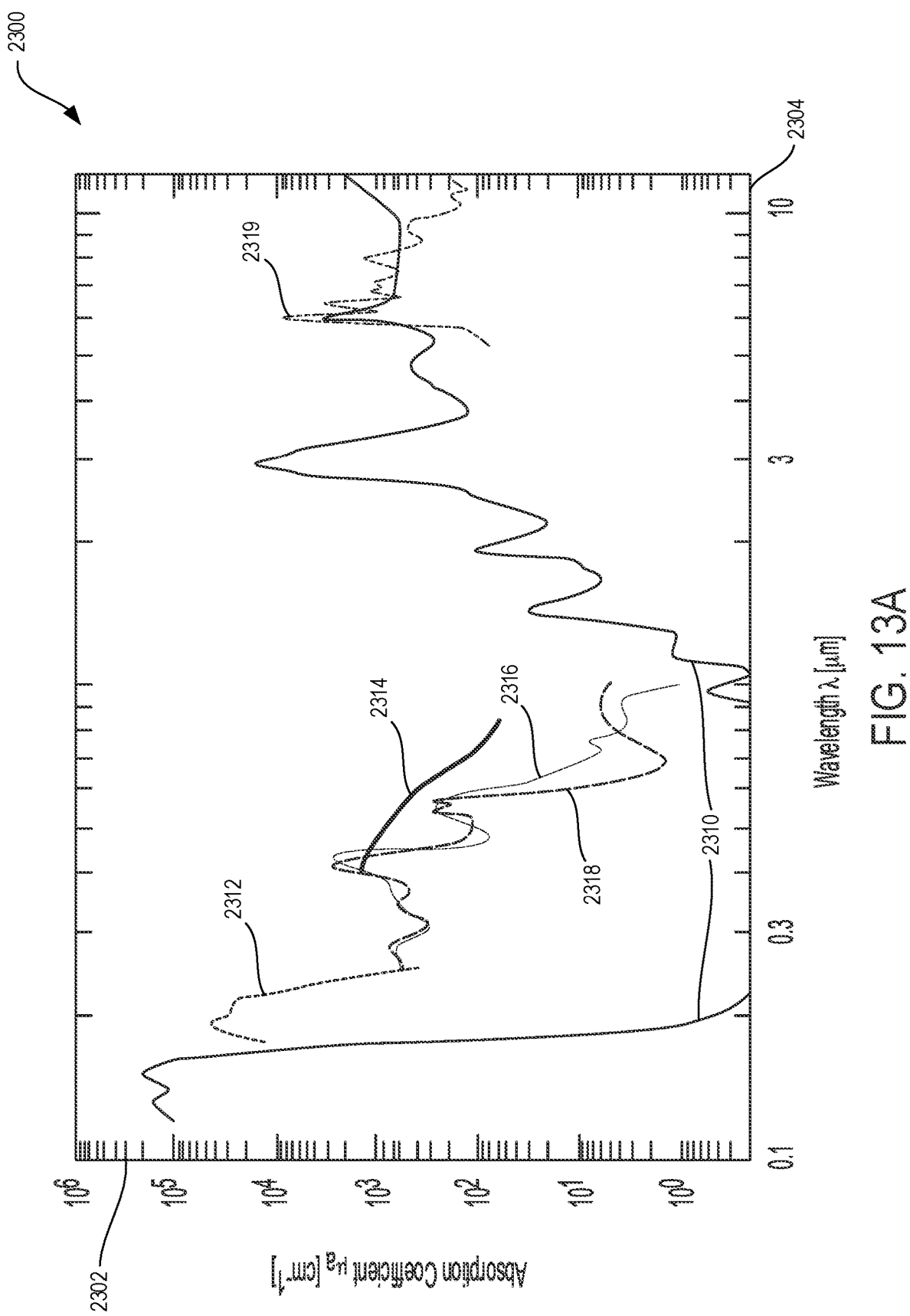
FIG. 13A is a graph of absorption coefficient verse wavelength for various biological materials, according to at least one aspect of the present disclosure.

As noted above, the various surgical visualization systems described herein can be utilized to visualize various different types of tissues and/or anatomical structures, including tissues and/or anatomical structures that may be obscured from being visualized by EMR in the visible portion of the spectrum. In one aspect, the surgical visualization systems can utilize a spectral imaging system to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be further configured to characterize the tissue type of the tissue being visualized based upon the particular combination of constituent materials. To illustrate, FIG. 13A is a graph 2300 depicting how the absorption coefficient of various biological materials varies across the EMR wavelength spectrum. In the graph 2300, the vertical axis 2303 represents absorption coefficient of the biological material (e.g., in $cm^{-1}$) and the horizontal axis 2304 represents EMR wavelength (e.g., in μm). The graph 2300 further illustrates a first line 2310 representing the absorption coefficient of water at various EMR wavelengths, a second line 2312 representing the absorption coefficient of protein at various EMR wavelengths, a third line 2314 representing the absorption coefficient of melanin at various EMR wavelengths, a fourth line 2316 representing the absorption coefficient of deoxygenated hemoglobin at various EMR wavelengths, a fifth line 2318 representing the absorption coefficient of oxygenated hemoglobin at various EMR wavelengths, and a sixth line 2319 representing the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 13B:
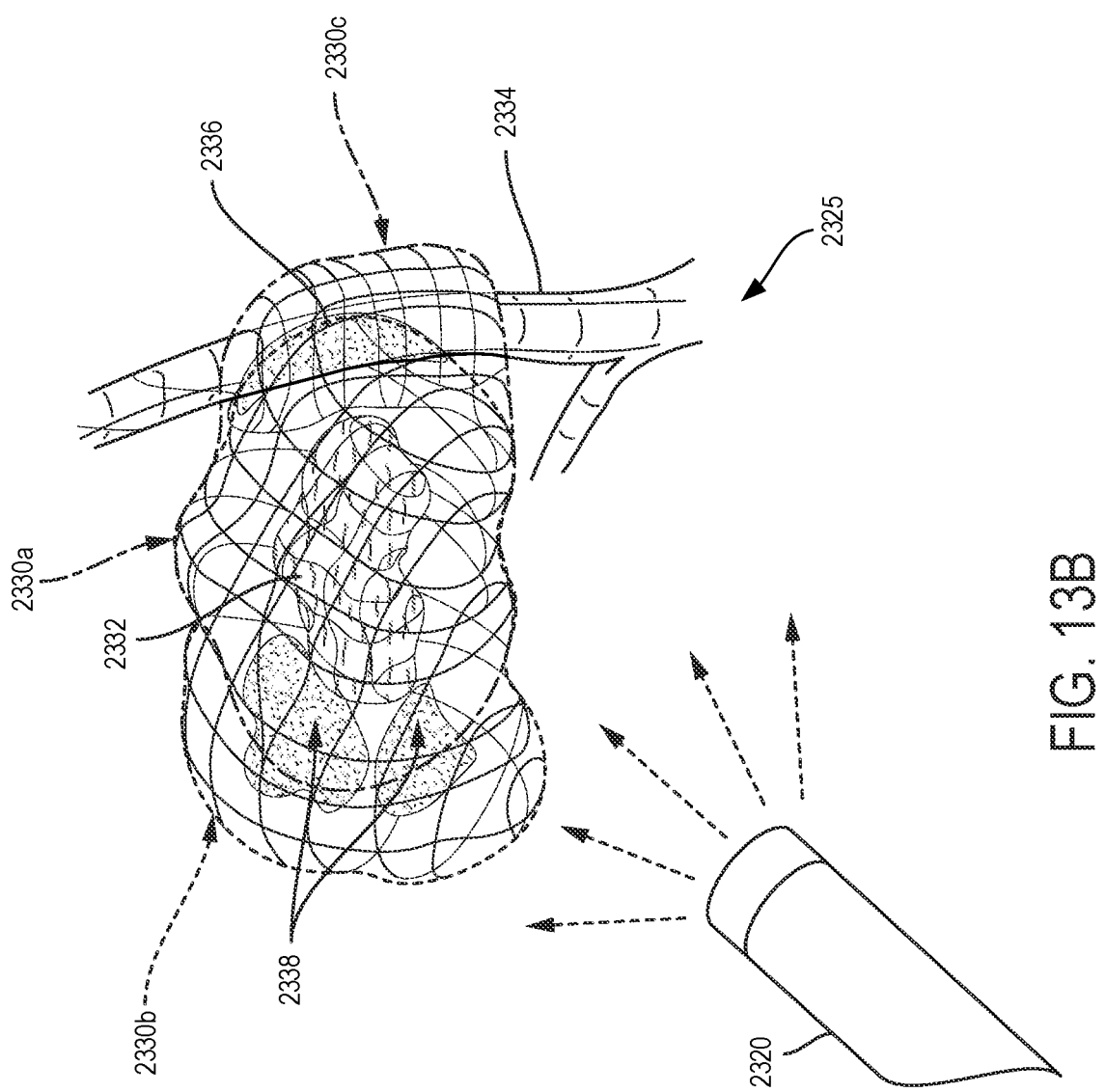
FIG. 13B is a schematic of the visualization of anatomical structures via a spectral surgical visualization system, according to at least one aspect of the present disclosure.

An illustration of the utilization of spectral imaging techniques to visualize different tissue types and/or anatomical structures is shown in FIG. 13B. In FIG. 13B, a spectral emitter 2320 (e.g., spectral light source 150) is being utilized by an imaging system to visualize a surgical site 2325. The EMR emitted by the spectral emitter 2320 and reflected from the tissues and/or structures at the surgical site 2325 can be received by an image sensor 135 (FIG. 2) to visualize the tissues and/or structures, which can be either visible (e.g., be located at the surface of the surgical site 2325) or obscured (e.g., underlay other tissue and/or structures at the surgical site 2325). In this example, an imaging system 142 (FIG. 2) can visualize a tumor 2332, an artery 2334, and various abnormalities 2338 (i.e., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system 142, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Further, the imaging system 142 can be configured to tailor or update the displayed surgical site visualization according to the identified tissue and/or structure types. For example, the imaging system 142 can display a margin 2330a associated with the tumor 2332 being visualized on a display screen (e.g., display 146). The margin 2330a can indicate the area or amount of tissue that should be excised to ensure complete removal of the tumor 2332. The control system 133 (FIG. 2) can be configured to control or update the dimensions of the margin 2330a based on the tissues and/or structures identified by the imaging system 142. In the illustrated example, the imaging system 142 has identified multiple abnormalities 2338 within the FOV. Accordingly, the control system 133 can adjust the displayed margin 2330a to a first updated margin 2330b having sufficient dimensions to encompass the abnormalities 2338. Further, the imaging system 142 has also identified an artery 2334 partially overlapping with the initially displayed margin 2330a (as indicated by the highlighted region 2336 of the artery 2334). Accordingly, the control system 133 can adjust the displayed margin 2330a to a second updated margin 2330c having sufficient dimensions to encompass the relevant portion of the artery 2334.

Tissues and/or structures can also be imaged or characterized according to their reflective characteristics, in addition to or in lieu of their absorptive characteristics described above with respect to FIGS. 13A and 13B, across the EMR wavelength spectrum. For example, FIGS. 13C-13E illustrate various graphs of reflectance of different types of tissues or structures across different EMR wavelengths. FIG. 13C is a graphical representation 1050 of an illustrative ureter signature versus obscurants. FIG. 13D is a graphical representation 1052 of an illustrative artery signature versus obscurants. FIG. 13E is a graphical representation 1054 of an illustrative nerve signature versus obscurants. The plots in FIGS. 13C-13E represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

In various instances, select wavelengths for spectral imaging can be identified and utilized based on the anticipated critical structures and/or obscurants at a surgical site (i.e., "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 14 and 15, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 15, for example, which can be measured by the receiver 1108.

Based on the delay between the emitted wave 1124 and the received wave 1125, the time-of-flight sensor system 1104 is configured to determine the distance d (FIG. 14). A time-of-flight timing diagram 1130 for the emitter 1106 and the receiver 1108 of FIG. 14 is shown in FIG. 15. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance din FIG. 14. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
$d_A$=the depth of the critical structure 1101;
$d_w$=the distance from the emitter 1106 to the critical structure 1101 (din FIG. 14); and
$d_t$=the distance from the emitter 1106 (on the distal end of the surgical device 1102) to the surface 1105 of the obscuring tissue 1103.

In one aspect of the present disclosure, referring now to FIG. 16, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described in various U.S. patent applications, which are incorporated by reference herein in the present disclosure.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}$, $d_{2a}$, $d_{3a}$, $d_{1b}$, $d_{2b}$, $d_{2c}$ indicated in FIG. 16.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}$, $d_{2a}$, $d_{3a}$, $d_{1b}$, $d_{2}b$, $d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}$, $d_{2a}$, $d_{3a}$, $d_{1b}$, $d_{2b}$, $d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 16, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 16, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-N IRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013, Vol. 138, No. 3, 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization systems disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure(s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

In various instances, clinicians may not know the location of a critical structure with respect to a surgical tool. For example, when a critical structure is embedded in tissue, the clinician may be unable to ascertain the location of the critical structure. In certain instances, a clinician may want to keep a surgical device outside a range of positions surrounding the critical structure and/or away from the visible tissue covering the hidden critical structure. When the location of a concealed critical structure is unknown, the clinician may risk moving too close to the critical structure, which can result in inadvertent trauma and/or dissection of the critical structure and/or too much energy, heat, and/or tension in proximity of the critical structure. Alternatively, the clinician may stay too far away from a suspected location of the critical structure and risk affecting tissue at a less desirable location in an effort to avoid the critical structure.

A surgical visualization system is provided that presents surgical device tracking with respect to one or more critical structures. For example, the surgical visualization system can track the proximity of a surgical device with respect to a critical structure. Such tracking can occur intraoperatively, in real-time, and/or in near real-time. In various instances, the tracking data can be provided to the clinicians via a display screen (e.g. a monitor) of an imaging system.

In one aspect of the present disclosure, a surgical visualization system includes a surgical device comprising an emitter configured to emit a structured light pattern onto a visible surface, an imaging system comprising a camera configured to detect an embedded structure and the structured light pattern on the visible surface, and a control circuit in signal communication with the camera and the imaging system, wherein the control circuit is configured to determine a distance from the surgical device to the embedded structure and provide a signal to the imaging system indicative of the distance. For example, the distance can be determined by computing a distance from the camera to the critical structure that is illuminated with fluoroscopy technology and based on a three-dimensional view of the illuminated structure provided by images from multiple lenses (e.g. a left-side lens and a right-side lens) of the camera. The distance from the surgical device to the critical structure can be triangulated based on the known positions of the surgical device and the camera, for example. Alternative means for determining the distance to an embedded critical structure are further described herein. For example, NIR time-of-flight distance sensors can be employed. Additionally or alternatively, the surgical visualization system can determine a distance to visible tissue overlaying/covering an embedded critical structure. For example, the surgical visualization system can identify a hidden critical structure and augment a view of the hidden critical structure by depicting a schematic of the hidden critical structure on the visible structure, such as a line on the surface of the visible tissue. The surgical visualization system can further determine the distance to the augmented line on the visible tissue.

By providing the clinician with up-to-date information regarding the proximity of the surgical device to the concealed critical structure and/or visible structure, as provided by the various surgical visualization systems disclosed herein, the clinician can make more informed decisions regarding the placement of the surgical device relative to the concealed critical structure. For example, the clinician can view the distance between the surgical device and the critical structure in real-time/intraoperatively and, in certain instances, an alert and/or warning can be provided by the imaging system when the surgical device is moved within a predefined proximity and/or zone of the critical structure. In certain instances, the alert and/or warning can be provided when the trajectory of the surgical device indicates a likely collision with a "no-fly" zone in the proximity of the critical structure (e.g. within 1 mm, 2 mm, 5 mm, 10 mm, 20 mm or more of the critical structure). In such instances, the clinician can maintain momentum throughout the surgical procedure without requiring the clinician to monitor a suspected location of the critical structure and the surgical device's proximity thereto. As a result, certain surgical procedures can be performed more quickly, with fewer pauses/interruptions, and/or with improved accuracy and/or certainty, for example. In one aspect, the surgical visualization system can be utilized to detect tissue variability, such as the variability of tissue within an organ to differentiate tumors/cancerous tissue/unhealthy tissue from healthy tissue. Such a surgical visualization system can maximize the removal of the unhealthy tissue while minimizing the removal of the healthy tissue.

Surgical Hub System

The various visualization or imaging systems described herein can be incorporated into a surgical hub system, such as is illustrated in connection with FIGS. 17-19 and described in further detail below.

Referring to FIG. 17, a computer-implemented interactive surgical system 2100 includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. In one example, as illustrated in FIG. 17, the surgical system 2102 includes a visualization system 2108, a robotic system 2110, and a handheld intelligent surgical instrument 2112, which are configured to communicate with one another and/or the hub 2106. In some aspects, a surgical system 2102 may include an M number of hubs 2106, an N number of visualization systems 2108, an O number of robotic systems 2110, and a P number of handheld intelligent surgical instruments 2112, where M, N, 0, and P are integers greater than or equal to one.

FIG. 18 depicts an example of a surgical system 2102 being used to perform a surgical procedure on a patient who is lying down on an operating table 2114 in a surgical operating room 2116. A robotic system 2110 is used in the surgical procedure as a part of the surgical system 2102. The robotic system 2110 includes a surgeon's console 2118, a patient side cart 2120 (surgical robot), and a surgical robotic hub 2122. The patient side cart 2120 can manipulate at least one removably coupled surgical tool 2117 through a minimally invasive incision in the body of the patient while the surgeon views the surgical site through the surgeon's console 2118. An image of the surgical site can be obtained by a medical imaging device 2124, which can be manipulated by the patient side cart 2120 to orient the imaging device 2124. The robotic hub 2122 can be used to process the images of the surgical site for subsequent display to the surgeon through the surgeon's console 2118.

Other types of robotic systems can be readily adapted for use with the surgical system 2102. Various examples of robotic systems and surgical tools that are suitable for use with the present disclosure are described in various U.S. patent applications, which are incorporated by reference herein in the present disclosure.

Various examples of cloud-based analytics that are performed by the cloud 2104, and are suitable for use with the present disclosure, are described in various U.S. patent applications, which are incorporated by reference herein in the present disclosure.

In various aspects, the imaging device 2124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 2124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 2124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in various U.S. patent applications that are incorporated by reference herein in the present disclosure. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 2124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 2108 includes one or more imaging sensors, one or more image-processing units, one or more storage arrays, and one or more displays that are strategically arranged with respect to the sterile field, as illustrated in FIG. 18. In one aspect, the visualization system 2108 includes an interface for HL7, PACS, and EMR. Various components of the visualization system 2108 are described in various U.S. patent applications that are incorporated by reference herein in the present disclosure.

As illustrated in FIG. 18, a primary display 2119 is positioned in the sterile field to be visible to an operator at the operating table 2114. In addition, a visualization tower 21121 is positioned outside the sterile field. The visualization tower 21121 includes a first non-sterile display 2107 and a second non-sterile display 2109, which face away from each other. The visualization system 2108, guided by the hub 2106, is configured to utilize the displays 2107, 2109, and 2119 to coordinate information flow to operators inside and outside the sterile field. For example, the hub 2106 may cause the visualization system 2108 to display a snapshot of a surgical site, as recorded by an imaging device 2124, on a non-sterile display 2107 or 2109, while maintaining a live feed of the surgical site on the primary display 2119. The snapshot on the non-sterile display 2107 or 2109 can permit a non-sterile operator to perform a diagnostic step relevant to the surgical procedure, for example.

In one aspect, the hub 2106 is also configured to route a diagnostic input or feedback entered by a non-sterile operator at the visualization tower 21121 to the primary display 2119 within the sterile field, where it can be viewed by a sterile operator at the operating table. In one example, the input can be in the form of a modification to the snapshot displayed on the non-sterile display 2107 or 2109, which can be routed to the primary display 2119 by the hub 2106.

Referring to FIG. 18, a surgical instrument 2112 is being used in the surgical procedure as part of the surgical system 2102. The hub 2106 is also configured to coordinate information flow to a display of the surgical instrument 2112, as is described in various U.S. patent applications that are incorporated by reference herein in the present disclosure. A diagnostic input or feedback entered by a non-sterile operator at the visualization tower 21121 can be routed by the hub 2106 to the surgical instrument display 2115 within the sterile field, where it can be viewed by the operator of the surgical instrument 2112. Example surgical instruments that are suitable for use with the surgical system 2102 are described in various U.S. patent applications that are incorporated by reference herein in the present disclosure.

FIG. 19 illustrates a computer-implemented interactive surgical system 2200. The computer-implemented interactive surgical system 2200 is similar in many respects to the computer-implemented interactive surgical system 2100. The surgical system 2200 includes at least one surgical hub 2236 in communication with a cloud 2204 that may include a remote server 2213. In one aspect, the computer-implemented interactive surgical system 2200 comprises a surgical hub 2236 connected to multiple operating theater devices such as, for example, intelligent surgical instruments, robots, and other computerized devices located in the operating theater. The surgical hub 2236 comprises a communications interface for communicably coupling the surgical hub 2236 to the cloud 2204 and/or remote server 2213. As illustrated in the example of FIG. 19, the surgical hub 2236 is coupled to an imaging module 2238 that is coupled to an endoscope 2239, a generator module 2240 that is coupled to an energy device 2421, a smoke evacuator module 2226, a suction/irrigation module 2228, a communication module 2230, a processor module 2232, a storage array 2234, a smart device/instrument 2235 optionally coupled to a display 2237, and a non-contact sensor module 2242. The operating theater devices are coupled to cloud computing resources and data storage via the surgical hub 2236. A robot hub 2222 also may be connected to the surgical hub 2236 and to the cloud computing resources. The devices/instruments 2235, visualization systems 2209, among others, may be coupled to the surgical hub 2236 via wired or wireless communication standards or protocols, as described herein. The surgical hub 2236 may be coupled to a hub display 2215 (e.g., monitor, screen) to display and overlay images received from the imaging module, device/instrument display, and/or other visualization systems 208. The hub display also may display data received from devices connected to the modular control tower in conjunction with images and overlaid images.

Situational Awareness

The various visualization systems or aspects of visualization systems described herein can be utilized as part of a situational awareness system that can be embodied or executed by a surgical hub 2106, 2236 (FIGS. 17-19). In particular, characterizing, identifying, and/or visualizing surgical instruments or other surgical devices (including their positions, orientations, and actions), tissues, structures, users, and other things located within the surgical field or the operating theater can provide contextual data that can be utilized by a situational awareness system to infer the type of surgical procedure or a step thereof being performed, the type of tissue(s) and/or structure(s) being manipulated by the surgeon, and so on. This contextual data can then be utilized by the situational awareness system to provide alerts to users, suggest subsequent steps or actions for the users to undertake, prepare surgical devices in anticipation for their use (e.g., activate an electrosurgical generator in anticipation of an electrosurgical instrument being utilized in a subsequent step of the surgical procedure), control surgical instruments intelligently (e.g., customize surgical instrument operational parameters based on each patient's particular health profile), and so on.

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control modular device incorrectly or suboptimally given the particular context-free sensed data. Modular devices can include any surgical devices that is controllable by a situational awareness system, such as visualization system devices (e.g., a camera or display screen), surgical instruments (e.g., an ultrasonic surgical instrument, an electrosurgical instrument, or a surgical stapler), and other surgical devices (e.g., a smoke evacuator). For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 20 illustrates a diagram of a situationally aware surgical system 2400, in accordance with at least one aspect of the present disclosure. In some exemplifications, the data sources 2426 include, for example, the modular devices 2402 (which can include sensors configured to detect parameters associated with the patient and/or the modular device itself), databases 2422 (e.g., an EMR database containing patient records), and patient monitoring devices 2424 (e.g., a blood pressure (BP) monitor and an electrocardiography (EKG) monitor).

A surgical hub 2404, which may be similar to the hub 106 in many respects, can be configured to derive the contextual information pertaining to the surgical procedure from the data based upon, for example, the particular combination(s) of received data or the particular order in which the data is received from the data sources 2426. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2404 to derive or infer information related to the surgical procedure from received data can be referred to as "situational awareness." In one exemplification, the surgical hub 2404 can incorporate a situational awareness system, which is the hardware and/or programming associated with the surgical hub 2404 that derives contextual information pertaining to the surgical procedure from the received data.

The situational awareness system of the surgical hub 2404 can be configured to derive the contextual information from the data received from the data sources 2426 in a variety of different ways. In one exemplification, the situational awareness system includes a pattern recognition system, or machine learning system (e.g., an artificial neural network), that has been trained on training data to correlate various inputs (e.g., data from databases 2422, patient monitoring devices 2424, and/or modular devices 2402) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2402. In one exemplification, the contextual information received by the situational awareness system of the surgical hub 2404 is associated with a particular control adjustment or set of control adjustments for one or more modular devices 2402. In another exemplification, the situational awareness system includes a further machine learning system, lookup table, or other such system, which generates or retrieves one or more control adjustments for one or more modular devices 2402 when provided the contextual information as input.

A surgical hub 2404 incorporating a situational awareness system provides a number of benefits for the surgical system 2400. One benefit includes improving the interpretation of sensed and collected data, which would in turn improve the processing accuracy and/or the usage of the data during the course of a surgical procedure. To return to a previous example, a situationally aware surgical hub 2404 could determine what type of tissue was being operated on; therefore, when an unexpectedly high force to close the surgical instrument's end effector is detected, the situationally aware surgical hub 2404 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2404 could infer whether a surgical procedure being performed is a thoracic or an abdominal procedure, allowing the surgical hub 2404 to determine whether the tissue clamped by an end effector of the surgical stapling and cutting instrument is lung (for a thoracic procedure) or stomach (for an abdominal procedure) tissue. The surgical hub 2404 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2404 could determine whether the surgical site is under pressure (by determining that the surgical procedure is utilizing insufflation) and determine the procedure type. As a procedure type is generally performed in a specific body cavity, the surgical hub 2404 could then control the motor rate of the smoke evacuator appropriately for the body cavity being operated in. Thus, a situationally aware surgical hub 2404 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 2404 could determine whether the surgical procedure is an arthroscopic procedure. The surgical hub 2404 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2404 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2404 can be configured to adjust the energy level for the ultrasonic surgical instrument or RF electrosurgical instrument throughout the course of a surgical procedure, rather than just on a procedure-by-procedure basis. A situationally aware surgical hub 2404 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2426 to improve the conclusions that the surgical hub 2404 draws from one data source 2426. A situationally aware surgical hub 2404 could augment data that it receives from the modular devices 2402 with contextual information that it has built up regarding the surgical procedure from other data sources 2426. For example, a situationally aware surgical hub 2404 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2404 can be further configured to compare a physiologic measurement (e.g., blood pressure sensed by a BP monitor communicably connected to the surgical hub 2404) with the visual or image data of hemostasis (e.g., from a medical imaging device 124 (FIG. 2) communicably coupled to the surgical hub 2404) to make a determination on the integrity of the staple line or tissue weld. In other words, the situational awareness system of the surgical hub 2404 can consider the physiological measurement data to provide additional context in analyzing the visualization data. The additional context can be useful when the visualization data may be inconclusive or incomplete on its own.

Another benefit includes proactively and automatically controlling the paired modular devices 2402 according to the particular step of the surgical procedure that is being performed to reduce the number of times that medical personnel are required to interact with or control the surgical system 2400 during the course of a surgical procedure. For example, a situationally aware surgical hub 2404 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2404 could determine whether the current or subsequent step of the surgical procedure requires a different view or degree of magnification on the display according to the feature(s) at the surgical site that the surgeon is expected to need to view. The surgical hub 2404 could then proactively change the displayed view (supplied by, e.g., a medical imaging device for the visualization system 108) accordingly so that the display automatically adjusts throughout the surgical procedure.

As yet another example, a situationally aware surgical hub 2404 could determine which step of the surgical procedure is being performed or will subsequently be performed and whether particular data or comparisons between data will be required for that step of the surgical procedure. The surgical hub 2404 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2404 could determine whether the operating theater is setup properly or optimally for the surgical procedure to be performed. The surgical hub 2404 can be configured to determine the type of surgical procedure being performed, retrieve the corresponding checklists, product location, or setup needs (e.g., from a memory), and then compare the current operating theater layout to the standard layout for the type of surgical procedure that the surgical hub 2404 determines is being performed. In one exemplification, the surgical hub 2404 can be configured to compare the list of items for the procedure scanned by a suitable scanner for example and/or a list of devices paired with the surgical hub 2404 to a recommended or anticipated manifest of items and/or devices for the given surgical procedure. If there are any discontinuities between the lists, the surgical hub 2404 can be configured to provide an alert indicating that a particular modular device 2402, patient monitoring device 2424, and/or other surgical item is missing. In one exemplification, the surgical hub 2404 can be configured to determine the relative distance or position of the modular devices 2402 and patient monitoring devices 2424 via proximity sensors, for example. The surgical hub 2404 can compare the relative positions of the devices to a recommended or anticipated layout for the particular surgical procedure. If there are any discontinuities between the layouts, the surgical hub 2404 can be configured to provide an alert indicating that the current layout for the surgical procedure deviates from the recommended layout.

As another example, a situationally aware surgical hub 2404 could determine whether the surgeon (or other medical personnel) was making an error or otherwise deviating from the expected course of action during the course of a surgical procedure. For example, the surgical hub 2404 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2404 determined is being performed. In one exemplification, the surgical hub 2404 can be configured to provide an alert indicating that an unexpected action is being performed or an unexpected device is being utilized at the particular step in the surgical procedure.

Overall, the situational awareness system for the surgical hub 2404 improves surgical procedure outcomes by adjusting the surgical instruments (and other modular devices 2402) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2402 in the surgical theater according to the specific context of the procedure.

Referring now to FIG. 21, a timeline 2500 depicting situational awareness of a hub, such as the surgical hub 106 or 206 (FIGS. 1-11), for example, is depicted. The timeline 2500 is an illustrative surgical procedure and the contextual information that the surgical hub 106, 206 can derive from the data received from the data sources at each step in the surgical procedure. The timeline 2500 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 2502 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 2504, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 2506, the medical personnel scan the patient band via a scanner that is communicably connected to the surgical hub 106, 206. The surgical hub 106, 206 can then confirm the patient's identity based on the scanned data.

Fourth step 2508, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 2510, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 2512, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 2512, the pre-operative portion of the lung segmentectomy procedure is completed and the operative portion begins.

Seventh step 2514, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 2516, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 2504 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 2518, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 2520, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 2522, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 2524, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 2524, the incisions are closed up and the post-operative portion of the procedure begins.

Thirteenth step 2526, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 2528 is that the medical personnel remove the various patient monitoring devices from the patient. The surgical hub 2106, 2236 can thus infer that the patient is being transferred to a recovery room when the hub loses EKG, BP, and other data from the patient monitoring devices. As can be seen from the description of this illustrative procedure, the surgical hub 2106, 2236 can determine or infer when each step of a given surgical procedure is taking place according to data received from the various data sources that are communicably coupled to the surgical hub 2106, 2236.

Situational awareness is further described in various U.S. patent applications that are incorporated by reference herein in the present disclosure, which is herein incorporated by reference in its entirety. In certain instances, operation of a robotic surgical system, including the various robotic surgical systems disclosed herein, for example, can be controlled by the hub 2106, 2236 based on its situational awareness and/or feedback from the components thereof and/or based on information from the cloud 2104 (FIG. 17).

Visualization with Structured Light to Extrapolate Metadata from Imaged Tissue

Surface irregularities (e.g. deformations and/or discontinuities) on tissue can be difficult to capture and portray in a visualization system. Additionally, tissue often moves and/or changes during a surgical procedure. In other words, the tissue is dynamic. For example, the tissue may be distorted, stressed, or become otherwise deformed by a surgical fastening operation. The tissue may also be transected and/or certain portions and/or layers of tissue may be removed. Underlying tissue and/or structures may become exposed during the surgical procedure. As the tissue moves, embedded structures underlying the visible tissue and/or hidden tissue margins within an anatomical structure may also move. For example, a resection margin may be concentrically positioned around a tumor prior to tissue deformation; however, as the anatomical structure is deformed during a surgical procedure, the resection margin may also become deformed. In certain instances, adjacent portions of tissue can shift, including those portions with previously-identified physical characteristics or properties. Generating three-dimensional digital representations or models of the tissue as it is deformed, transected, moved, or otherwise changed during a surgical procedure presents various challenges; however, such dynamic visualization imaging may be helpful to a clinician in certain instances.

In various aspects of the present disclosure, a visualization system can include a plurality of light sources in combination with structured light patterns to extrapolate additional tissue characteristics or metadata related to the imaged tissue. For example, surface irregularities of tissue can be identified with the combination of structured light and multiple coherent light sources. Additionally or alternatively, the surface irregularities can be identified with the combination of structured light and non-coherent or diffuse light and stereoscopic image sensors. In one instance, the plurality of light sources can emit patterns of structured light at different wavelengths. The different wavelengths can reach different surfaces of an anatomical structure, such as an outer surface and an underlying subsurface. An image sensor of the visualization system can receive imaging data from the image sensor indicative of the different surfaces of the anatomical structure. The visualization system can then generate a three-dimensional digital representation of the anatomical structure based on the structured light patterns on the different surfaces of the anatomical structure imaged by the image sensor. In certain instances, subsurface contours can be utilized to fill-in gaps in a visualization of the surface due to tissue irregularities thereon. Additionally or alternatively, subsurface contours can be analyzed to determine and track movement of embedded structures and/or tissue layers.

As the tissue moves during a surgical procedure, it may be useful in certain circumstances to update information in a visualization display. For example, it can be helpful to show tissue velocity, tissue distortion, tissue irregularities, tissue vascularization, and/or updated identification of one or more embedded structures. By comparing imaging frames of the tissue at different points in time, a control circuit of the surgical system can analyze the additional tissue characteristics or metadata and provide updated visualization images to the clinician to communicate the same.

In various instances, a situational awareness module can inform the identification of tissue irregularities based on expectations at the surgical site. For example, the situational awareness module may expect to identify a row of staples or a scar at a particular location based on the type of surgical procedure, the step in the surgical procedure, the type(s) of tissue, and/or various tissue characteristics, for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional patent Application Ser. No. 62/611,340, titled CLOUD-BASED MEDICAL ANALYTICS, filed Dec. 28, 2017, the disclosure of each of which is herein incorporated by reference in its entirety.

Imaging by a visualization system can be converted into measurable data and information for the clinician(s) and/or surgical hub(s). For example, visualization can be utilized to analyze surgical device usage and to provide opportunities for improvement or device optimization in certain instances. In various instances, situational awareness can inform the visualization system. For example, a surgical system including a situational awareness module communicatively coupled to a visualization system, as described herein, can be configured to provide updated information, such as updated tissue characteristics and/or metadata, for example, to a clinician via a display during a surgical procedure. Updated visualization imaging or other data can be provided automatically based on input from the situational awareness module and/or can be suggested by the situational awareness module based on an awareness of the surgical procedure, patient, and/or tissue. Such a visualization system is adaptive to the surgical scenario.

More specifically, the visualization images can be updated in accordance with input from the situational awareness module. For example, the situational awareness module can determine the type of surgical procedure, the step in the surgical procedure, the type(s) of tissue, and/or various tissue characteristics, as further described herein. Updates to the visualization images can be automated and/or recommended to a clinician based on inputs from the situational awareness module. For example, if the situational awareness module becomes aware that a staple line has been fired into tissue, the situational awareness module can order or suggest updating the visualization imaging to show the tissue compression along the staple line. As another example, if the situational awareness module becomes aware that visible tissue has shifted during a surgical procedure, the situational awareness module can order or suggest updating the visualization imaging to show the updated configuration of a resection margin. Additional surgical scenarios are contemplated and various examples are provided throughout the present disclosure.

Referring now to FIG. 22, portions of a computer-implemented interactive surgical system are shown. The computer-implemented interactive surgical system includes a cloud-based system 6004 and at least one surgical hub 6006 in communication with the cloud-based system 6004. Various elements of the computer-implemented interactive surgical system can be identical to those of the computer-implemented interactive surgical system 2100 (FIG. 17). For example, the surgical hub 6006 can be identical to the surgical hub 2106 and the cloud-based system 6004 can be identical to the cloud-based system 2104. The computer-implemented interactive surgical system in FIG. 22 also includes a visualization system 6008 having a control circuit 6032, which is configured to communicate with the hub 6006 and/or a situational awareness module such as the situational awareness module 6007 of the hub 6006, for example.

The visualization system 6008 can be similar in many respects to the visualization system 100 (FIG. 1) and the visualization system 2108 (FIG. 17). For example, the visualization system 6008 includes a memory 6034 communicatively coupled to the control circuit 6032. The visualization system 6008 also includes multiple light sources 6050, an imaging system 6042 having a camera 6044, a display 6046, and controls 6048. The camera 6044 includes at least one image sensor 6035. In other instances, the adaptive visualization system 6008 can include multiple cameras, for example.

The visualization system 6008 is configured to adapt in response to input from the hub 6006. In such instances, the visualization system 6008 is an adaptive visualization system. For example, the hub 6006 includes the situational awareness module 6007, which is configured to synthesize data from multiple sources to determine an appropriate response to a surgical event. For example, the situational awareness module 6007 can determine the type of surgical procedure, step in the surgical procedure, type of tissue, and/or tissue characteristics, as further described herein. Moreover, such a situational awareness module 6007 can recommend a particular course of action or possible choices to a system based on the synthesized data. In various instances, a sensor system encompassing a plurality of sensors distributed throughout a surgical system can provide data, images, and/or other information to the situational awareness module 6007. Such a situational awareness module 6007 can be incorporated into a control unit of the surgical hub 6006, for example. In various instances, the visualization system 6008 is configured to update or otherwise modify the visualization(s) provided to the clinician(s) based on the input from the situational awareness module 6007.

The light sources 6050 can include at least one structured light source for determining the surface geometry and contours of an anatomical structure. 3DIntegrated, Inc. (3Di) of Copenhagen, Denmark, provides a platform based on structured light, deep learning, and structure from motion principles to obtain three-dimensional data in real-time. For example, in certain instances, 3Di software can be utilized to determine the three-dimensional position of surgical tools, generate the three-dimensional reconstruction of surgical surfaces, and obtain coordinates for computer-driven surgery, for example. In various instances, a structured light pattern utilizing a single imaging array can be utilized to determine surface contouring, for example. Reliance on a single structured light pattern can provide an incomplete digital model. Certain portions of a surface can be obstructed if there are surface irregularities, for example. In certain instances, as further described herein, multiple structured light arrays can be employed, such as multiple arrays on the same laparoscopy camera, for example, to generate a more complete digital model.

The visualization system 6008, for example, can include multiple light sources in combination with structured light patterns to extrapolate additional aspects, characterizations, or metadata of the imaged tissue. As further described herein, the additional aspects can be tissue velocity, tissue distortion, tissue irregularity, tissue vascularization, and identification of an embedded structure within the anatomical structure, for example. Vascularization can be analyzed by tracking the underlying moving particles, for example. In one aspect, Doppler imaging may be used to determine the velocity flow of particles such as blood cells flowing within a blood vessel such as a vein, capillary, or artery. Doppler imaging may provide a direction and velocity of cell flow through the blood vessel. Additionally or alternatively, infrared (IR) absorption may identify the red blood cells as being oxygen-rich—thereby identifying the blood vessel as an artery—or oxygen-depleted—thereby identifying the blood vessel as a vein. Tissue characterization is further described in U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No 2019/0200905, and U.S. patent application Ser. No. 15/940,704, titled USE OF LASER LIGHT AND RED-GREEN-BLUE COLORATION TO DETERMINE PROPERTIES OF BACK SCATTERED LIGHT, both filed Mar. 29, 2018, now U.S. Patent Application Publication No 2019/0206050, which are incorporated by reference herein in their respective entireties.

In certain aspects of the present disclosure, certain portions of the imaging frames with structured light can be utilized to add three-dimensional tissue variances. These portions can provide additional tissue characteristics and/or metadata of the imaged tissue. In various instances, the structured light source can include a multi-source structured light. For example, the light sources 6050 (FIG. 22) can be multiple coherent light sources or lasers. The use of coherent light can enable the differentiation and separation of the surface refractivity from the three-dimensional distortion of the structured light pattern. Additionally or alternatively, phase shift data from the multiple coherent light sources can be utilized to characterize tissue properties.

In one example, coherent light can be projected onto visible tissue in a predefined two-dimensional structured light pattern (i.e., a spatial intensity pattern such as a series of lines or a grid). The structured light pattern of coherent light can be cycled. In one aspect, the coherent light patterns may be cycled among a variety of grids having different line spacings or orientations. In another aspect, the coherent light patterns may be cycled among a variety of parallel lines at a variety of line spacings. In yet another aspect, the light patterns may be cycled among a variety of light wavelengths. For example, at 480 frames-per-second (FPS), sixty frames can be used for each of eight different color segments or wavelengths. In some aspects, multiple sequential frames may be taken at the same light wavelength. Alternatively, sequential frames may be taken using alternating light wavelengths for each frame. A portion of the frames can be digitally removed from the three-dimensional surface mapping visualization. For example, ten frames for each of the sixty frames of each wavelength can be digitally removed. If the visualized tissue remains stationary throughout a group of frames, the digitally removed frames may be used to produce an averaged image. Though the digitally-removed frames may not be utilized for three-dimensional surface mapping, the surface refractivity (or other properties) of those portions can be utilized to determine additional tissue characteristics and/or metadata. Examples of such tissue characteristics may include, without limitation, a tissue composition and/or a tissue sub-structure orientation (for example, the underlying orientation of collagen or elastin fibers). Tissue characterization is further described in U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, now U.S. Patent Application Publication No. 2019/0200905, which is incorporated by reference herein in its entirety.

In various instances, the light source 6050 can includes red, green, blue, infrared, and ultraviolet lasers. Multiple wavelengths can be utilized for certain light, such as infrared and/or ultraviolet, for example. In some aspects, multiple infrared light sources within the range of about 700 nm to about 1400 nm may be used. In some examples, the infrared light may have a wavelength of about 705 nm, about 730 nm, about 761 nm, about 780 nm, about 785 nm, about 800 nm, about 830 nm, 850 nm, 940 nm, 980 nm, 1064 nm, or 1370 nm. In some aspects, multiple ultraviolet light sources within the range of about 200 nm to about 400 nm may be used. In some examples, the ultraviolet light may have a wavelength of about 211 nm, about 236 nm, about 263 nm, about 266 nm, about 351 nm, or about 351 nm. In certain instances, nine sources can be utilized. For example, the infrared and ultraviolet frame sets can be alternated as they are displayed in a 60 Hz visualization portion in real time and the metadata obtained from these frame sets can be superimposed on the image as needed.

In various instances, the light sources 6050 can include non-coherent or broad spectrum sources, which can be imaged with stereoscopic imaging sensors. Stereoscopic imaging of structured light can provide a three-dimensional image of the distorted structured light pattern. A three-dimensional image of the distorted pattern can lessen the need for a calculative adjustment of the two-dimensional image, for example. However, the distorted pattern can still be compared with the surface refractivity to determine if the surface of the anatomical structure, or the tissue just under the surface, contains a three-dimensional irregularity.

In certain aspects of the present disclosure, multiple CMOS arrays and FPGA conversion circuits can be incorporated into the visualization system to acquire time-synced interrelated metadata about the imaged tissue. For example, the resolution of an image obtained by a CMOS sensor can be enhanced by combining a multi-color structured light image received by the CMOS sensor with an image obtained by a higher resolution grey scale imaging sensor to enable the micronization of the specific array such that more than one array can be positioned on the same laparoscopy camera. The multiple arrays enable stereoscopic replication of the same image as well as independent FPGAs or independent sensors to monitor different aspects of the image or related metadata in real-time. Multi-array imaging is further described in U.S. patent application Ser. No. 15/940,742, titled DUAL CMOS ARRAY IMAGING, filed Mar. 29, 2018, now U.S. Patent Application Publication No 2019/0200906, which is incorporated by reference herein in its entirety.

Referring now to FIG. 23, portions of a visualization system 6108 are shown. The visualization system 6108 is similar in many respects to the visualization system 6008 in FIG. 22. For example, the visualization system 6108 includes a structured light projector 6150 for projecting structured light patterns onto tissue T at a plurality of different wavelengths and a camera 6144 having at least one image sensor. The structured light projector 6150 and the camera 6144 are communicatively coupled to a control circuit, such as the control circuit 6032 (FIG. 22). The camera 6144 is configured to detect imaging data from the structured light projector 6150 and convey the imaging data to the control circuit for processing.

In various instances, surface irregularities of the tissue T can be identified with the imaging data obtained by the camera 6144 and sent to the control circuit. For example, the structured light pattern reflected from the surface of the tissue T may provide an incomplete picture of the surgical site due to irregularities along the surface of the tissue T in certain instances. When the surface has one or more irregularities such as a tear, cut, and/or deformation that interferes with the structured light pattern, the entire structured light pattern may not be reflected by the surface and, thus, may not be detected by the image sensor of the camera 6144. For example, a surface deformation can cast a shadow that obstructs a portion of the structured light pattern. In such instances, structured light patterns penetrating the surface of the tissue and reflected from a sub-surface thereof can be utilized to fill gaps in the three-dimensional digital rendering. For example, one or more wavelengths of coherent light that penetrate the surface of the tissue can be utilized to determine the contours of the subsurface. As further described herein, the structured light pattern or patterns can be emitted at different wavelengths and captured by the image sensor. Certain subsurface light patterns may be digitally removed from the three-dimensional digital rendering; however, such patterns can be used to extrapolate the contours of the tissue surface. More specifically, the geometry of the tissue surface can be extrapolated from the curvature of one or more tissue sub-surfaces.

Referring again to FIG. 23, the visualization system 6108 can be configured to identify the surface geometry of an organ 6160, such as a stomach, for example, as further described herein. However, irregularities 6164 on the surface of the organ 6160 can inhibit the generation of a complete three-dimensional model of the organ 6160. For example, the irregularity 6164, which may be a scar or other tissue malformation, can block the structured light pattern emitted by the structured light projector 6150 from reaching portions of the tissue T surface. However, a pattern of structured light at a tissue-penetrating wavelength can be configured to penetrate the irregularity 6164 and can be detected at a sub-surface layer by the image sensor of the camera 6144. The tissue-penetrating structured light pattern can be utilized by the control circuit to determine a curvature of the underlying tissue surface and, thus, extrapolate the surface of the organ 6160 including the irregularity 6164 thereof.

In certain instances, a tissue-penetrating structured light pattern can be utilized to determine compression of tissue. For example, tissue can be compressed along a staple line. In various instances, uniform tissue compression is desired to obtain a reliable tissue seal. The tissue-penetrating structured light patterns can be utilized by the control circuit to generate a subsurface three-dimensional visualization of tissue compression along an embedded staple line. More specifically, the movement of tissue layers, include one or more subsurface layers, can be monitored and tracked to analyze the compression thereof along a staple line.

Additionally or alternatively, the refractivity R of the structured light pattern, as detected by the image sensor of the camera 6144, can provide supplemental information and/or metadata regarding the tissue characteristics of the imaged tissue in certain instances. Also, in certain instances, phase shift data for multiple coherent lights from the structured light projector 6150 can provide supplemental information and/or metadata regarding the imaged tissue. For example, irregularities 6164 can be identified based on refractivity and/or phase shift data. In certain instances, an irregularity 6164 can include one or more key anatomical structures 6162, which can be tracked by the structured light pattern reflected thereon and mapped to the digital model thereof.

Another visualization system 6208 is shown in FIG. 24. The visualization system 6208 can be similar to the visualization system 6108 (FIG. 23) and can be configured to visualize the organ 6160, including irregularities 6164 along the surface and/or key anatomical structures 6162 thereof. The visualization system 6208 comprises a single surgical device including both a structured light source 6250 and a camera 6244. In various instances, the structured light source 6250 can be configured to emit coherent light and the camera 6244 can be configured to detect the phase shift of the coherent light reflected back from the surface of the tissue T. The tissue can be characterized by the phase shift data. For example, the phase shift data can be a supplementary source of information regarding the visualized tissue. Different degrees of phase shift can correspond to different physical properties. In some aspects, a phase shift of the reflected light may indicate motion of the surface or subsurface structures. In other aspects, a phase shift of the reflected light may indicate subsurface layers.

Referring now to FIG. 40, a logic flow diagram of a process 6800 of conveying a three dimensional model to a clinician is shown. In the following description of the process 6800, reference should be made to the control circuit 132 (FIG. 2) and/or the visualization system 6008 (FIG. 22). In one aspect, the process 6800 can be embodied as a set of computer-executable instructions embodied as software (e.g., as stored in the memory 134) or hardware that are executed by the control circuit 132 of the control system 133 and/or the control circuit 6032.

The visualization system 6008 executing the process 6800 can obtain, at block 6802, first imaging data from an image sensor, such as the image sensor 6035, for example. The first imaging data can be indicative of an outer surface contour of an anatomical structure from a first pattern of structured light detected by the image sensor 6035. At block 6804, the visualization system 6008 can obtain second imaging data from the image sensor 6035. The second imaging data can be indicative of a subsurface contour of the anatomical structure from a second pattern of structured light. The second pattern of structured light can comprise a different wavelength than the first pattern of structured light. The first imaging data and the second imaging data can be transmitted to the control circuit 6032, for example, at blocks 6806 and 6808, respectively. The control circuit 6032 can generate a three-dimensional digital representation of the anatomical structure at block 6812. The digital representation or model can include the outer surface contour and the subsurface contour. In various instances, additional layers of tissue can be imaged with the process 6800. Upon completing the three-dimensional model, the control circuit 6032 can transmit, at block 6814, the three-dimensional model to a display 6046, for example.

In one aspect, the control circuit 6032 is also configured to receive a signal from the situational awareness module 6007 of the surgical hub 6006 and, in response to the signal from the situational awareness module 6007, update the three-dimensional model of the anatomical structure. In various aspects, the control circuit 6032 is further configured to obtain metadata from at least one of the first imaging data and the second imaging data at the processing block 6810. The control circuit 6032 can be configured to overlay the metadata with the three-dimensional model at block 6812 and transmit the additional information to the clinician at block 6814. The metadata can correspond to at least one of tissue velocity, tissue distortion, tissue irregularity, tissue vascularization, or identification of an embedded structure within the anatomical structure, as further described herein. In one aspect, the metadata can be indicative of tissue compression, such as embedded tissue along a staple line, for example. The situational awareness module 6007 can dictate or suggest when metadata is processed and conveyed to the clinicians based on a detected surgical scenario and corresponding information that may be helpful to the clinician in each surgical scenario.

In various instances, an adaptive visualization system can provide visualization of motion at the surgical site. Structured light can be used with stereoscopic imaging sensors and multi-source coherent light to map light pattern distortions from one time frame to another time frame. The mapping of light pattern distortions across frames can be used to visualize and analyze anatomic distortion. Moreover, as the three-dimensional digital representations or models are deformed, any superimposed three-dimensional imaging—such as embedded structures, tissue irregularities, and/or hidden boundaries and/or tissue margins—can be proportionately deformed with the three-dimensional model. In such instances, the visualization system can convey movement of the superimposed three-dimensional imaging to a clinician as the tissue is manipulated, e.g. dissected and/or retracted.

In various aspects of the present disclosure, an adaptive visualization system can obtain baseline visualization data based on situational awareness (e.g. input from the situational awareness module 6007). For example, a baseline visualization of an anatomical structure and/or surgical site can be obtained before initiation of a surgical procedure— such as before the manipulation and dissection of tissue at the surgical site. The baseline visualization image of the anatomical geometry can include a visualization of the surface of the anatomical structure and its boundaries. Such a baseline visualization image can be used to preserve overall orientation of the surgical site and anatomic structure even as local regions within the anatomic structure are progressively disrupted, altered, or otherwise manipulated during the surgical procedure. Maintaining the baseline visualization image can allow the disrupted regions to be ignored when mapping other imaging irregularities. For example, when mapping or overlaying structures and/or features obtained by other imaging sources, the baseline visualization image can be used and the distorted regions ignored to appropriately position the additional structures and/or features in the updated visualization image.

Situational awareness can be used to instruct and/or recommend an update to a baseline visualization image. For example, referring again to FIG. 22, the situational awareness module 6007 can instruct the control circuit 6032 to update the baseline visualization image upon identifying a particular type of surgical procedure, step in the surgical procedure, type of tissue, and/or one or more specific tissue characteristics. In one example, an updated baseline visualization image can be helpful after a transection or after the application of one or more rows of staples. In certain instances, distorted sub-regions within an original anatomical structure can separately create a new baseline visualization image or update an existing baseline visualization image for the distorted sub-region(s) to properly inform image overlays. For example, a key region of a patient's anatomy can be updated after removal of a tumor or growth therein.

In various instances, a frame-to-frame comparison can be used to calculate the deformation of the tissue. For example, surface features can be tracked and compared against subsequent frames with a reference frame set by the user or by an external data source. For example, the pattern of structured light on the surface can deflect and move as the tissue surface moves. Stereoscopic image sensors can detect the deflection of the structured light patterns. A user can set the reference frame with a manual timestamp, for example. A ventilator (i.e. external data source) can set the reference frame in other instances. For example, the ventilator timestamp can correspond to the expiratory pressure to denote an expired lung. Non-rigid iterative closest point algorithms can be used to compute correspondences between the frames. In one aspect, an initial image frame may be taken as a baseline image and subsequent image frames may be geometrically transformed so that the subsequent images are referenced to the baseline image. From this comparison, deformation between the frames can be computed. Such a technique can become more robust with increased strain rates, for example.

In various instances, the model can be analyzed to compute estimated changes in deformation for a proposed resection. For example, before a clinician resects a portion of tissue, the proposed resection line(s) can be added to the digital model, which can be updated to show the anatomical structure with the hypothetical resection. Referring again to FIG. 13B, in one example, a clinician may intend to remove a wedge-shaped portion from the tissue at the surgical site 2325 to remove the tumor 2332 along with the tissue abnormalities 2338. In such instances, the model can be updated to show the organ with the wedge-shaped portion removed therefrom. The updated model can depict the deformation of the tissue, as well as the computed stress and/or strain in the tissue based on the known tissue mechanical properties and the deformation induced by the surgery. For example, the tissue can be shaded or otherwise layered with the stress and/or strain data so that the clinician is informed regarding how a particular resection may impact strain on the tissue. In some aspects, the stress/strain data may be overlaid on the image as a set of vector lines indicating stress/strain direction and line type or color to indicate the value of the stress/strain. Based on the computed stresses and strains, a clinician may modify the proposed resection and consider an alternative strategy to reduce and/or better distribute the stresses and strains within the tissue. For example, the angles of the resections can be modified. In certain instances, the clinician can reorient a staple line with a preferred strain direction.

In various instances, the deformation data can be used to effect resection margins. For example, a resection margin can be distorted in the same distortion pattern as the tissue boundary. Referring again to FIG. 13B, after a first transection to remove a portion of the tissue at the surgical site 2325, the digital model can be updated by comparing the frames and computing the deformation of the tissue. As the tissue visualized with the structured light moves, the underlying resection margins 2330a, 2330b, 2330c can also shift and/or move. In various instances, the digital model can be updated to show the surgical site 2325 including the computed updated position of the resection margins 2330a, 2330b, 2330c, which can be modeled with the same distortion pattern as the visible tissue at the surgical site 2325. It can be assumed the resection margins 2330a, 2330b, 2330c deform along with the visible tissue, for example. Additionally, with the use of tissue penetrating laser light, the structure or orientation of the underlying tissue components, such as collagen or elastin fibers, may be determined. Such fiber orientation may provide additional information regarding the stress and/or strain applied to the tissue.

The projected distorted resection margins, i.e. distortions based on frame-to-frame comparisons of structured light patterns on a tissue surface, may be modified as new underlying layers of tissue are exposed and the refractivity of the newly exposed tissue is also checked for refractivity changes. The newly-identified tissue characteristics can be indicated to the user in real-time during tissue dissections and/or as the clinician approaches the margin boundaries. For example, referring to FIGS. 25A and 25B, a surgical site 6325 includes tissue T and a surgical device includes a structured light source 6350 and image sensor 6344, similar to the surgical device in FIG. 24. A first refractivity R can be expected (FIG. 25A); however, the actual deflected reflected light R' (FIG. 25B) can be different as new layers of tissue are exposed. The different refractivity can be indicative of different tissue characteristics. For example, upon complete removal of a tumor 2332 and/or tissue abnormalities 2338, the refractivity can indicate different, i.e. healthy, tissue properties. In various instances, refractivity within a boundary 6330 of an irregularity can be different than the refractivity outside the boundary 6330 of the irregularity.

Adjustment of Surgical Instrument Controls According to POV Coordinate System

In one general aspect, a surgical system can be configured to communicate a locally displayed coordinate system from an imaging system to a surgical instrument or other medical device to enable the instrument/device controls to be adapted to control motion relative to a local visualization coordinate system. In particular, at least one measurement derived from the imaging system can be utilized to define the local coordinate system. Further, the surgical instrument or other medical device can be provided a transfer function from the visualization system 2108 and/or the surgical hub 2106 (e.g., as described in connection with FIGS. 17-19) coupled to the visualization system 2108 to enable the surgical instrument or other medical device to orient the user controls relative to the local coordinate system, rather than a standard global coordinate system or another coordinate system.

As an example, handheld surgical instruments that have a rotatable shaft and/or an articulatable end effector require the user to understand how the shaft and the end effector are oriented relative to the patient when deciding which articulation control (e.g., left or right articulation controls) will articulate the end effector in the desired direction with respect to the patient. Accordingly, the surgical instrument or a control system coupled to the surgical instrument can be configured to automatically reorient the function of the articulation controls based on the shaft and the end effector's position relative to the handle. However, linking the reorientation of the controls directly to a change in the orientation of the surgical instrument handle assembly or rotation of the surgical instrument shaft can be undesirable in certain instances because the particular orientation of the handle assembly, shaft, and/or other surgical instrument components relative to the user may not necessarily correspond to how those components are oriented on a display screen in a video-assisted surgical procedure, such as a VATS procedure. Surgeons utilize display screens or video monitors as their sole POV for controlling the surgical instrument(s) during a video-assisted surgical procedure. Causing the surgical instrument controls to automatically change in response to reorientation or rotation of the surgical instrument could cause the functions of the controls to change unpredictably for users and would not necessarily correspond to the POV provided on the display for the surgeon.

To address this issue, the orientation of the surgical instrument (i.e., the shaft and/or end effector of the surgical instrument) currently displayed to the surgeon by the imaging system on a display screen could be utilized as a reference relative to a global coordinate system associated with the patient. Accordingly, the displayed orientation of the surgical instrument relative to the global coordinate system could be utilized to adjust the function of the controls on the surgical instrument, which would in turn cause the controls to correspond to the orientation displayed on the display screen. Having the surgical instrument's controls be automatically adjusted so that they correspond to how the surgical instrument is shown on the display screen would improve the ease of using the surgical instruments and reduce user confusion and disorientation by obviating the need for surgeons to be constantly aware of how the handle, shaft, and/or end effector of the surgical instrument is oriented relative to the patient before controlling the articulation or movement of the surgical instrument. Further, for surgical instruments that have built-in display screens, the orientation of the display screens could likewise be controlled in the same manner as the controls of the surgical instrument. In sum, the functions of the controls, such as the left/right articulation controls and/or display screen of a surgical instrument, could be adjusted according to, or to coincide with, the locally displayed coordinate system.

In one aspect, the present disclosure is directed to a control system for a surgical instrument that includes a user control. The control system can include an imaging system and a control circuit connected to the imaging system and connectable to the surgical instrument (e.g., via wired or wireless connections). The imaging system can be configured to visualize a surgical site, as described above. The control circuit can be configured to generate an image of the surgical site utilizing the imaging system, define a first coordinate system with respect to the surgical site according to the image thereof, receive a second coordinate system defined by the surgical instrument, determine a transfer function to translate a coordinate in the second coordinate system to the first coordinate system, and provide the transfer function to the surgical instrument to cause the surgical instrument to adjust the user control according to the transfer function. In another aspect, the present disclosure is directed to a surgical instrument operably in signal communication with the control system, including the imaging system that is configured to generate an image of the surgical site based on the electromagnetic radiation (EMR) reflected therefrom and define a first coordinate system with respect to the surgical site according to the image thereof. The surgical instrument can include a user control configured to control a function of the surgical instrument and/or a display screen. The surgical instrument can further include a control circuit coupled to the user control and/or the display screen. The control circuit can be configured to determine a second coordinate system with respect to the surgical instrument that can be provided to the control system, receive the transfer function to translate a coordinate in the second coordinate system to the first coordinate system from the control system, and adjust the user control and/or the display screen according to the transfer function.

In order to assist in the understanding of the aforementioned systems and methods, various examples will be described within the context of a VATS procedure. It should be understood that this is simply for illustrative purposes. The described systems and methods are applicable to other contexts and/or surgical procedures, however. A VATS procedure is a surgical procedure whereby one or more surgical instruments and one or more thoracoscopes (i.e., cameras) are inserted into the patient's chest cavity through slits positioned between the patient's ribs. The cameras are utilized to provide the surgeons with a view of the interior of the patient's chest cavity to allow the surgeon to properly position/move the surgical instrument(s) and manipulate tissue/structures within the chest cavity. Because the surgeon controls the surgical instrument(s) based on what is displayed by the imaging system via the camera(s) and because the surgical instrument(s) may not be aligned with the viewing perspective of the camera(s), the spatial relationship between the surgical instrument and the POV displayed by the imaging system can be potentially disorienting, especially for imaging systems that allow users to pan, manipulate, and reorient the displayed visualization, as described below under the headings "Fusion of Images from Different Sources to Expand Visualization Field Scope" and "Fusion of Overlapping Images to Expand Visualization Field Scope", for example. Accordingly, the present disclosure is directed to surgical instruments and control systems associated therewith that are configured to intelligently adapt the surgical instrument controls so that they correspond to the POV displayed to the surgeon.

To illustrate further, FIGS. 26 and 27 are diagrams of aspects of a VATS procedure. In this particular VATS procedure, the surgeon is seeking to remove a tumor 6506 located within the apical segment of the superior lobe of a lung 6508. In this particular illustrative procedure, the surgeon has placed a port 6502 between the second rib 6501 and the third rib 6503 to provide an access path 6504 for a surgical instrument 6510 (e.g., a surgical stapler) insertable through the port 6502 to access the tumor 6506 and/or the surrounding area within the chest cavity. Once the location of the access for the surgical instrument 6510 has been selected, the surgeon can place one or more cameras 6520a, 6520b through other ports 6502 that are positioned to allow the camera(s) 6520a, 6520b to visualize the interior of the patent chest cavity in the vicinity of the surgical site. Visualizing the surgical site in this manner allows the surgeon to position and orient an end effector 6514 of the surgical instrument 6510 to manipulate the tissue as needed (e.g., excise a portion of the lung 6508 around the tumor 6506). In the particular illustrated example, two cameras 6520a, 6520b are utilized, although a different number of cameras can be utilized and/or one or more of the cameras 6520a, 6520b can be oriented in a different manner depending upon the particular type of surgical procedure that is being performed and/or the region within the body of the patient 6500 that needs to be visualized.

As shown in FIG. 27 and set forth below in TABLE 1, a variety of different coordinate systems can be defined with respect to the differing POVs of the patient, devices, or device components. Further, for imaging systems that allow users to manipulate the displayed visualization, as described below under the headings "Fusion of Images from Different Sources to Expand Visualization Field Scope" and "Fusion of Overlapping Images to Expand Visualization Field Scope", for example, "virtual" POVs can be defined that correspond to the virtual or predicted visualization being displayed to the surgeon and coordinate systems can also be defined according to these POVs. The generation and control of such visualizations are further described herein.

TABLE 1

| Coordinate System | Description |
| --- | --- |
| $x_p, y_p, z_p$ | Patient anatomical plane POV |
| $x_d, y_d, z_d$ | Handle assembly POV |
| $x_j, y_j, z_j$ | End effector/cartridge POV |
| $x_{c1}, y_{c1}, z_{c1}$ | Camera #1 POV |
| $x_{c2}, y_{c2}, z_{c2}$ | Camera #2 POV |
| $x_{L1}, y_{L1}, z_{L1}$ | Virtual local POV #1 |
| $x_{L2}, y_{L2}, z_{L2}$ | Virtual local POV #2 |
| $x_{L3}, y_{L3}, z_{L3}$ | Virtual local POV #3 |

In one aspect, the coordinate systems can be defined based upon sensor measurements and/or measurements by the imaging system 142 (FIG. 2). For example, a coordinate system with respect to a surgical instrument handle assembly 6512, a shaft 6513, or the end effector 6514 could be defined according to measurements by an accelerometer or another such sensor associated with the respective components. As another example, any of the aforementioned coordinate systems could be defined based upon measurements of the relative distances and/or positions of objects with respect to each other or a global coordinate system as determined by imaging the objects via the imaging system 142.

Referring now to FIG. 29, a logic flow diagram of a process 6550 of adjusting a display screen 6516 and/or user control 6518 (e.g., articulation control 6519a, 6519b) of a surgical instrument 6510 according to a displayed coordinate system is shown. In the following description of the process 6550, reference should also be made to the control circuit 132 in FIG. 2. In one aspect, the process 6550 can be embodied as a set of computer-executable instructions embodied as software (e.g., as stored in the memory 134) or hardware that are executed by the control circuit 132 of the control system 133. In the following description of the process, reference should also be made to the exemplary procedure of FIGS. 26-28.

The control circuit 132 executing the process 6550 can generate, at block 6552, an image of the surgical site utilizing the imaging system 142. As noted above, the imaging system 142 can be configured to generate images (including of both visible and nonvisible structures) and take measurements of or characterize imaged objects by emitting structured or non-structured EMR, emitting EMR in both the visible and nonvisible spectrums, and so on. The generated image can include an image directly captured by an image sensor 135 representing the POV of one of the cameras 6520a, 6520b, as shown in FIG. 30, for example. Alternatively, the generated image can include a virtual image, as are shown in FIGS. 33 and 34, for example.

The control circuit 132 can define, at block 6554, a local or POV coordinate system based on the imaging system 142 for the generated image. The local coordinate system can be defined based on sensor measurements, imaging system measurements, tracking movement relative to an established coordinate system (e.g., a camera coordinate system $x_c$, $y_c$, $z_c$ as shown in FIG. 32), and so on.

The control circuit 132 can receive, at block 6556, a coordinate system from the surgical instrument 6510. In one aspect, the control circuit 132 is operably in signal communication with the surgical instrument 6510 via a wireless connection (e.g., a Bluetooth connection), for example. In one aspect, the control circuit 132 can be embodied as a control circuit of a surgical hub 2106, 2236 (FIGS. 17-19) and the surgical instrument 6510 can be paired with the surgical hub 2106, 2236 to transmit data therebetween.

The control circuit 132 can determine, at block 6558, a transfer function to translate a coordinate in one of the surgical instrument coordinate system or the local coordinate system to the other coordinate system. For example, the transfer function can be configured to translate. The transfer function can be embodied as an algorithm, an equation, a lookup table, and so on.

The control circuit 132 can provide, at block 6560, the transfer function to the surgical instrument 6510. As noted above, the control circuit 132 can be communicatively coupled to the surgical instrument 6510 via a wireless connection, for example, for transferring data therebetween. Once received by the surgical instrument 6510, the surgical instrument 6510 can utilize the transfer function to translate the coordinates in its coordinate system to the displayed coordinate system and determine whether to adjust its controls 6518 and/or display screen 6516 based upon the updated coordinates, which indicate how the surgical instrument 6510 or components thereof are being visualized by the surgeon.

In the example shown in FIG. 28, the surgical instrument 6510 has utilized the provided transfer function to determine that the controls 6518 and display screen 6516 should be adjusted based on the updated coordinates. In various instances, situational awareness, as further described herein, can inform when the controls 6518 and/or the display screen 6516 are updated. The display screen 6516 can display a GUI 6517 that is adjusted from a first orientation, shown on the left side of FIG. 28, to a second orientation, shown on the right side of FIG. 28, to ensure that the GUI 6517 is oriented properly for the surgeon controlling the surgical instrument 6510. In one aspect, the GUI 6517 can further include a GUI element 6524 (e.g., an icon) indicating the POV or coordinate system being utilized by the surgical instrument 6510.

In this example, the GUI element 6524 shifts to indicate that the POV displayed by the visualization system 2108 has changed from the device coordinate system ("DVC") to the local coordinate system ("Local") associated with the image/video displayed by the visualization system 2108.

As an example, the surgical instrument controls 6518 adjusted according to the updated coordinates can include articulation controls. The articulation controls can include a first control 6519a configured to cause the surgical instrument 6510 to articulate in a first direction and a second control 6519b configured to cause the surgical instrument 6510 to articulate in a second direction, for example. The articulation controls 6519a, 6519b can be embodied as a rocker, toggle, or separate actuators and/or buttons, for example. In this example, the surgical instrument 6510 has caused the first articulation control 6519a and the second articulation control 6519b to swap functions in response to the change in orientation of the surgical instrument 6510. In other words, actuating the first articulation control 6519a would instead cause the surgical instrument 6510 to articulate in the second direction, and actuating the second articulation control 6519b would cause the surgical instrument 6510 to articulate in the first direction. Accordingly, the functions of the articulation controls 6519a, 6519b can be set according to the orientation of the surgical instrument 6510 or a component thereof (e.g., the end effector 6514) as displayed to the user, such as shown in FIGS. 30 and 32-34.

Additionally or alternatively, in certain instances, the GUI 6517 on the display screen 6516 can be adjusted. For example, the GUI 6517 can be inverted when the handle assembly 6512 is inverted. In certain instances, the GUI 6517 can include a touch screen such that the surgeon can switch between coordinate systems by interacting with the GUI 6517. For example, the surgeon can toggle between a device POV, local POV, and/or one or more other POVs by interacting with the GUI 6517.

Fusion of Images from Different Sources to Expand Visualization Field Scope

One issue that can arise during video-assisted surgical procedures is that the field of view (FOV) offered by the visualization system can be inadequate in certain circumstances because the cameras are necessarily limited in number and fixed in position due the surgical constraints of the procedure. In particular, the POV offered by the cameras could be non-ideal for performing particular steps of the surgical procedure (e.g., dissecting a vessel), hiding particular tissues and/or structures from view, and so on. In one general aspect, a surgical system comprising an imaging system can be configured to create 3D representations of objects within the visualization field of the imaging system and characterize the 3D shapes to allow users to alter the displayed visualization with respect to the established coordinate system to better visualize the surgical site. The 3D representations can be generated from images generated from real-time sources (e.g., the imaging system 142) or non-real-time sources (e.g., CT scans or MRIs). In one aspect, the imaging system 142 can be configured to project structured light, or structured EMR, to create structured 3D shapes that can be tracked in real time. These 3D shapes could be generated in such a manner as to allow the POV displayed by the imaging system 142 to be moved or rotated away from the scanning source's local coordinate system to improve the perspective view of the user through the display.

Various aspects of the present disclosure can address the various technical problems described above. In one aspect, the present disclosure is directed to a control system, including an imaging system, a display screen, and a control circuit coupled to the imaging system and the display screen. The imaging system can be configured to image tissues, structures, and objects at the surgical site using a variety of different imaging techniques, including structured EMR. Further, the control circuit can be configured to generate a first image of the surgical site based on the structured EMR reflected therefrom received by the image sensor, receive a second image of the surgical site, generate a 3D representation of the surgical site based on the first image and the second image as aligned, display the 3D representation on the display screen, receive a user selection to manipulate the 3D representation, and update the 3D representation as displayed on the display screen from a first state to a second state according to the user selection.

Various examples will be described herein within the context of a VATS procedure; however, alternative surgical procedures are also contemplated. In particular, FIG. 30 illustrates a FOV 6570 of a camera 6520 (FIG. 32) during a VATS procedure. The target of this particular illustrative procedure is a tumor 6506 located within the apical segment of the superior lobe 6580 of a lung 6508. A number of biological structures are identifiable within this FOV 6570, including the thoracic wall 6509, veins 6574, arteries 6576, bronchi 6578, the fissure 6582 delineating the superior lobe 6580, a pulmonary artery 6584, and a pulmonary vein 6586. Non-biological objects are also viewable within the FOV 6570, including the end effector 6514 and the shaft 6513 of the surgical instrument 6510 being controlled by the surgeon. In a conventional imaging system, such a view, in combination with any corresponding views from any additional camera(s) 6520 being utilized, would be the sole view(s) available to surgeons performing a video-assisted procedure. Although the cameras are placed with the intent to provide the surgeon with an adequate visualization field scope for performing the surgical procedure, the visualization field scope provided by the camera(s) 6520 may ultimately not provide the ideal FOV 6570 for performing each step or task in the surgical procedure, or unexpected obstructions may be present at the surgical site that impede the surgeon's view. Further, intraoperatively repositioning or reorienting the camera(s) 6520 can be impractical or undesirable in certain instances due to the surgical constraints of the procedure.

In one aspect, a surgical system can be configured to expand the visualization field scope provided by the camera(s) 6520 by combining multiple images of the surgical site, including preoperative images and intraoperative images, to generate 3D representations of the surgical site or tissues and/or structures located at the surgical site. During the surgical procedure, the user can then manipulate the 3D representations displayed by the imaging system 142 to visualize the surgical site from orientations that are outside the scope of the FOV 6570 of the camera(s) 6520 being utilized in the procedure. Such reoriented views can be referred to as "virtual POVs," as noted above. Accordingly, the surgical system can supplement the FOV 6570 provided by the camera(s) 6520 and allow surgeons to dynamically adjust the displayed visualization of the surgical site during the surgical procedure to find ideal viewing POVs for performing one or more of the surgical tasks.

FIG. 31 is a diagram of image sources from which a 3D representation of a surgical site can be generated. In order to generate the 3D representations and thereby allow users to manipulate the visualization field scope to POVs extending beyond the FOV 6570 of the camera(s) 6520, the patient cavity would need to be viewed from multiple reference points (e.g., camera positions). These different reference points or perspectives can in turn be utilized to construct the 3D representations that can be intraoperatively manipulated by the surgeon to extend the visualization field scope beyond the fixed perspectives of the camera(s) 6520. In one aspect, at least some of the images can be captured utilizing structured EMR to map the surface of the tissues and/or structures located at the surgical site for generating the 3D representations. In one aspect, intraoperative images 6600 can be utilized in constructing the 3D representations. For example, as a camera 6520 is initially placed, the user may be prompted by the surgical system to pan the camera 6520 around the patient cavity to observe all of the anatomy and thereby establish a baseline set of images that can be fused together to form a 3D representation of the surgical site. This baseline can be updated automatically throughout the procedure as tissues are manipulated, the patient is moved, and so on. Alternatively, the baseline can be generated automatically as the camera 6520 is panned and/or reoriented during the surgical procedure and updated as more regions of the patient anatomy are exposed to the FOV 6570 of the camera 6520. In certain instances, situational awareness, as further described herein, can provide update instructions and/or suggestions to the surgeon based on the detected surgical scenario. In another aspect, preoperative images, such as CT scans 6602 and MRIs 6604 can be utilized in constructing the 3D representations. For example, images from non-real-time sources (e.g., CT scans 6602 and MRIs 6604) can be incorporated into the real-time mapping of the surgical site in its baseline coordinate system. The corresponding fused images provided by the non-real-time image sources can then be utilized to generate the 3D representation and manipulated in a similar fashion as described above.

The 3D representations can be generated from any combination of preoperative and intraoperative image sources. In one aspect, the 3D representations can be generated by aligning two-dimensional images and then constructing the 3D representation using photogrammetry techniques and/or 3D scanning software. Further, some captured images can include or indicate a 3D topography of the tissues and/or structures that can aid in constructing the 3D representations, such as images captured via structured EMR. Further details regarding the generation of 3D representations of tissues and/or structures can be found in U.S. patent application Ser. No. 16/128,195, titled INTEGRATION OF IMAGING DATA, filed on Sep. 11, 2018, now U.S. Patent Application Publication No. 2020/0015907, which is hereby incorporated by reference herein in its entirety.

In various aspects, the imaging system 142 can display the 3D representations generated from the fused images and provide users with controls (e.g., a GUI) for manipulating the displayed visualization POV. As one example, FIG. 32 is a visualization display 6620 and GUI 6622 of the surgical procedure of FIG. 27 provided by an imaging system 142. The visualization display 6620 and GUI 6622 can be displayed on a display 146 (FIG. 2), for example. The visualization display 6620 can include a real-time video feed from the camera(s) 6520 supplemented with the generated 3D representation of the surgical site, for example. The video feed provided by the camera(s) 6520 can be overlaid on or otherwise displayed in conjunction with the generated 3D representations on the visualization display 6620. The visualization display 6620 can be configured to display the video feed and transition to the 3D representations when the user causes the visualization display 6620 to display a POV that differs from the real-time video feed POV provided by the camera(s) 6520. In this particular example, the visualization display 6620 displays 3D representations of a lung 6508, a tumor 6506, and various structures 6610 (e.g., vessels). The 3D representations can be generated from non-real-time image sources and real-time images 6600 captured via the camera 6520, for example. The 3D representations can include portions that lie at least partially outside of the FOV of the camera 6520 and that can be displayed on the visualization display 6620 when desired by the user, as shown in FIG. 32.

In one aspect, the display 146 can include an interactive control, such as a GUI 6622, which allows the user to select portions of the visualization display 6620, particular camera POVs, or underlying 3D structures and then highlight, zoom in or out, rotate, or otherwise manipulate the visualization display 6620 to visualize the surgical site from a different perspective or approach than the view provided by the camera(s) 6520. The GUI 6622 can be configured to allow the user to select a surface, point, coordinate system, instrument, or superimposed scanned image and then adjust the visualization display 6620 with respect to that selection resulting in a view or visualization that is not directly aligned with the real-time image/video being provided by the camera(s) 6520 coupled to the imaging system 142.

For example, FIG. 33 illustrates the visualization display 6620 as shifted by a user to a first updated perspective 6530 corresponding to a first virtual POV $x_{L1}$, $y_{L1}$, $z_{L1}$ to view 3D representations of the lung 6508, the tumor 6506, and/or the end effector 6514 of the surgical instrument 6510 from a different, "local" perspective that may be more beneficial for the particular surgical procedure step. As indicated in FIG. 33, the first virtual POV $x_{L1}$, $y_{L1}$, $z_{L1}$ is shifted relative to the camera POV $x_c$, $y_c$, $z_c$ (e.g., as shown in FIG. 30) and the user is thus viewing, at least partially, 3D representations of the corresponding tissues, structures, and/or objects as displayed. As another example, FIG. 34 illustrates the visualization display 6620 as shifted by a user to a second updated perspective 6632 corresponding to a second virtual POV $x_{L2}$, $y_{L2}$, $z_{L2}$ to view the lung 6508, the tumor 6506, and/or the end effector 6514 of the surgical instrument 6510 from yet a different "local" perspective that is likewise shifted relative to the camera POV $x_c$, $y_c$, $z_c$ (e.g., as shown in FIG. 30). In one aspect, the GUI 6622 can include a perspective control widget 6628 that can be actuated by the user to shift, pan, or otherwise manipulate the perspective being shown on the visualization display 6620. Further, the GUI 6622 can include a coordinate GUI element 6626 that can indicate the shift in the displayed perspective relative to a reference perspective (e.g., the camera POV $x_c$, $y_c$, $z_c$). The GUI 6622 can also include various other controls for controlling the visualization display 6620, such as a zoom widget 6625 configured to cause the visualization display 6620 to zoom in our out on a particular point, structure, or object within the visualization display 6620.

In one aspect, the imaging system 142 can be configured to display the 3D representation in a different color than the real-time video feed, highlight the structure of the 3D representation, or otherwise indicate that the user is no longer viewing the real-time video feed when the user shifts the displayed POV of the visualization display 6620 away from the real-time video feed POV provided by the camera(s) 6520. Further, the imaging system 142 can be configured to allow users to shift back to the real-time video feed POV provided by the camera(s) 6520. In one aspect, the GUI 6622 includes a POV selection widget 6624 that allows the user to shift between various POVs, including camera POVs ("CAMERA"), device POVs ("DEVICE 1" and "DEVICE 2"), and virtual POVs defined by the user ("LOCAL"). In various instances, by selecting one of the POVs from the POV selection widget 6624, the visualization image can snap to the selected POV.

The visualization display 6620 can be further configured to calculate and/or display various measurements or parameters associated with the displayed tissues, structures, and objects. In one aspect, the surgical system can be configured to determine and display a tumor margin 6572 about the tumor 6506. The tumor margin 6572 can define the minimum volume of tissue that should be excised by the surgeon to ensure complete removal of the tumor 6506. The tumor margin 6572 can be calculated as a set distance extending about the tumor 6506 in three dimensions or can vary according to the size, geometry, location, and other such factors associated with the tumor 6506. In one aspect, the surgical system can be configured to determine and display relative distances between tissues, structures, and objects within the visualization display 6620. In the illustrated example, the visualization display 6620 includes the distance $d_1$ between the surgical instrument 6510 and the tumor margin 6572 and the distance $d_2$ between the surgical instrument 6510 and the surface of the tissue over which the surgical instrument end effector 6514 is located (which, in the illustrated example, is a lung 6508). In another aspect, the GUI 6622 can include a distance GUI element 6627 indicating the calculated distances between the various tissues, structures, and/or objects being visualized, i.e. between the corresponding elements in column A and column B. The aforementioned measurements are provided for illustrative purposes and the surgical system can calculate and display a variety of other measurements or parameters.

Referring now to FIG. 35, a logic flow diagram of a process 6650 of controlling a visualization display 6620 is shown. In the following description of the process 6650, reference should also be made to the control circuit 132 in FIG. 2. In one aspect, the process 6650 can be embodied as a set of computer-executable instructions embodied as software (e.g., as stored in the memory 134) or hardware that are executed by the control circuit 132 of the control system 133. In the following description of the process, reference should also be made to FIGS. 30-34.

The control circuit 132 executing the process 6650 can generate, at block 6652, a first image of the surgical site. The first image can be generated via the imaging system 142 utilizing structured or non-structured EMR to generate a 3D surface map of the imaged region, multispectral imaging techniques to identify and characterize nonvisible tissues and/or structures, and any other visualization techniques described above. Further, the first image can be generated as a series of images obtained by panning a camera about a surgical site to generate a 3D representation of the surgical site, as shown in FIG. 31, for example.

The control circuit 132 can receive, at block 6654, a second image of the surgical site. The second image can be a non-real-time image, such as a CT scan 6602 or MRI 6604, as shown in FIG. 31, for example.

The control circuit 132 can generate, at block 6656, a 3D representation of the surgical site from the first image, the second image, and any other images obtained from various image sources and then display, at block 6658, the 3D representation on a display screen coupled to the imaging system, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Once the 3D representation is displayed (either alone or in conjunction with a video feed from the cameras 6520), the control circuit 132 can update, at block 6660, the POV or state of the 3D representation according to a user selection. For example, the user could update the visualization display 6620 from the camera POV shown in FIG. 30 to a first virtual POV shown in FIG. 33 or a second virtual POV shown in FIG. 34. The user can provide the input to update the visualization display 6620 via a perspective control widget 6628 provided via a GUI 6622 associated with the visualization display 6620, for example.

Fusion of Overlapping Images to Expand Visualization Field Scope

As noted above, one issue that can arise during video-assisted surgical procedures is that the FOV offered by the visualization system can be inadequate in certain circumstances because the cameras are necessarily limited in number and fixed in position due the surgical constraints of the procedure. Systems and methods for addressing this and other technical problems can include, in one aspect, the use of two independent image scanning sources and sensors (e.g., cameras) having scanned regions that at least partially overlap or intersect. This enables the surgical system to generate 3D surfaces and volumes that have aspects that are not fully captured by only one of the fixed image scanning sources. Accordingly, the surgical system can create a virtual display visualization POV that can be moved relative to the surgical site, allowing the user to see around structures, tissues, or objects (e.g., surgical instruments) at the surgical site that may be obstructing one of the imaging devices.

Various aspects of the present disclosure can address the various technical problems described above. In one aspect, the present disclosure is directed to a control system, including an imaging system, a display screen, and a control circuit coupled to the imaging system and the display screen. The imaging system can include a first image sensor having a first FOV and a second image sensor having a second FOV that at least partially overlaps with the first FOV. The imaging system can be configured to image tissues, structures, and objects at the surgical site using a variety of different imaging techniques, including structured EMR. The control circuit can be configured to generate a first image of the surgical site based on the first image sensor, generate a second image of the surgical site based on the second image sensor, align the first image and the second image according to overlapping portions thereof, generate a 3D representation of a structure based on the first image and the second image as aligned, cause the display screen to display the 3D representation, and cause the display screen to adjust a displayed portion of the 3D representation according to a user selection.

In one aspect, a computational image generator could also be used to select clear image frames between the imaging devices and to display only the clear image frames in the areas where the FOVs of the imaging devices overlap. In another aspect, the surgical system can be configured to remove obstructions from the visualization display or render the obstructions semi-transparent in the areas where the FOVs of the imaging devices overlap. A visualization display 6620 (FIG. 38) and/or a GUI 6622 (FIG. 38) associated therewith can be configured to indicate to the user when the advanced visualization features are active to make the user aware that portions of the visualization display 6620 are simulated or have been adjusted from the "real" video feed provided by the cameras 6520a, 6520b (FIG. 38).

In one aspect, one of the cameras 6520*a*, 6520*b* can be designated as the default or primary camera, and images generated therefrom can likewise be considered to be the default or primary images displayed via the visualization display 6620. In this aspect, the images or other sensed information (e.g., multispectral tissue data) from the primary imaging device can be compared against that of the secondary imaging device to confirm the consistency of the images generated by the first imaging device. Further, differences between the two sets of images that are within a certain magnitude can be interpolated by the surgical system. Still further, differences between the two sets of images above a threshold can prevent calculated information from being displayed to the user (e.g., due to concerns of the accuracy of the calculated information caused by the lack of consistency between the images within the primary image set). In certain instances, situational awareness, as further described herein, can determine a suitable accuracy range or tolerance based on the detected surgical scenario, for example.

In one aspect, the surgical site surface information obtained by the imaging devices can be used to inform the superposition of underlying structures (e.g., a tumor) imaged via another imaging source (e.g., a CT scan). The superposition of the underlying structures can be adjusted to account for tissue deformation in the computational image against the data from the alternative or secondary imaging source in order to confirm the projected location of the underlying structures with respect to the imaged surface.

Referring now to FIGS. 36-38, various diagrams and a visualization display 6620 of a VATS procedure being performed utilizing two cameras 6520*a*, 6520*b* that have overlapping FOVs are shown. In particular, the first camera 6520*a* can have a first FOV 6700 and the second camera 6520*b* can have a second FOV 6702. The FOVs 6700, 6702 can further define an overlapping portion 6704 therebetween. Due to the overlapping portion 6704 of the images generated by the cameras 6520*a*, 6520*b*, the images can be aligned and then utilized to generate a 3D representation of the surgical site using the various techniques described above. Further, the control system 133 (FIG. 2) can be configured to remove an obstruction or correct an imaging artifact present within the overlapping portion 6704 of one of the generated images and replace the offending image portion with an interpolation of the corresponding unobstructed or correct portion of the other image. In this way, the control system 133 can dynamically update and maximize the visualization scope provided by the visualization display 6620. For example, the control system 133 can be configured to remove objects laying within the FOV of one or both of visualization FOVs 6700, 6702, such as the cameras 6520*a*, 6520*b* as shown in FIG. 38 or other surgical devices present at the surgical site, from the visualization display 6620.

Referring now to FIG. 39, a logic flow diagram of a process 6750 of controlling a visualization display 6620 (FIG. 38) is shown. In the following description of the process 6750, reference should also be made to the control circuit 132 in FIG. 2. In one aspect, the process 6750 can be embodied as a set of computer-executable instructions embodied as software (e.g., as stored in the memory 134) or hardware that are executed by the control circuit 132 of the control system 133. In the following description of the process, reference should also be made to FIGS. 36-38.

The control circuit 132 executing the process 6750 can generate, at block 6752, a first image of the surgical site and can generate, at block 6754, a second image of the surgical site. The images can be generated via the imaging system 142 utilizing structured or non-structured EMR to generate a 3D surface map of the imaged region, multispectral imaging techniques to identify and characterize nonvisible tissues and/or structures, and any other visualization techniques described above. Further, the first and second images can be generated by respective cameras 6520*a*, 6520*b* having overlapping FOVs. Therefore, the first and second images can correspondingly overlap with each other.

The control circuit 132 can generate, at block 6756, a 3D representation of the surgical site from the first image, the second image, and any other images obtained from various image sources and then display, at block 6758, the 3D representation on a display screen coupled to the imaging system, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Once the 3D representation is displayed (either alone or in conjunction with a video feed from at least one of the cameras 6520*a*, 6520*b*), the control circuit 132 can update, at block 6760, the POV or state of the 3D representation according to a user selection. The user can provide the input to update the visualization display 6620 via a perspective control widget 6628 provided via a GUI 6622 associated with the visualization display 6620, for example.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

Various aspects of the subject matter described herein are set out in the following numbered examples.

Example 1—A surgical visualization system comprising a first light source configured to emit a first pattern of structured light at a first wavelength, a second light source configured to emit a second pattern of structured light at a second wavelength that is different than the first wavelength, an image sensor configured to detect the first pattern of structured light and the second pattern of structured light on an anatomical structure, and a control circuit. The control circuit is configured to receive first imaging data from the image sensor. The first imaging data is indicative of an outer surface contour of the anatomical structure from the first pattern of structured light detected by the image sensor. The control circuit is further configured to receive second imaging data from the image sensor. The second imaging data is indicative of a subsurface contour of the anatomical structure from the second pattern of structured light. The control circuit is further configured to generate a three-dimensional digital representation of the anatomical structure including the outer surface contour and the subsurface contour.

Example 2—The surgical visualization system of Example 1, wherein the control circuit is further configured to receive a signal from a situational awareness module and in response to the signal from the situational awareness module, update the three-dimensional digital representation of the anatomical structure.

Example 3—The surgical visualization system of Example 1 or 2, wherein the image sensor is configured to detect phase shift data for the first light source.

Example 4—The surgical visualization system of Example 1, 2, or 3, wherein the image sensor is configured to detect phase shift data for the second light source.

Example 5—The surgical visualization system of Example 1, 2, 3, or 4, wherein the control circuit is further configured to obtain metadata from the first and second imaging data and overlay the metadata with the three-dimensional digital representation.

Example 6—The surgical visualization system of Example 5, wherein the metadata comprises at least one of tissue velocity, tissue distortion, tissue irregularity, tissue vascularization, or identification of an embedded structure within the anatomical structure.

Example 7—The surgical visualization system of Example 5 or 6, wherein the metadata is indicative of tissue compression along a staple line.

Example 8—A non-transitory computer-readable medium storing computer readable instructions, which when executed, cause a machine to detect, by an image sensor, a first pattern of structured light on an anatomical surface contour and a second pattern of structured light on a subsurface contour of the anatomical surface contour. The non-transitory computer-readable medium storing computer readable instructions, which when executed, further cause the machine to transmit, to a control circuit, first imaging data indicative of the first pattern of structured light and second imaging data indicative of the second pattern of structured light. The non-transitory computer-readable medium storing computer readable instructions, which when executed, further cause the machine to process, by the control circuit, the first imaging data and the second imaging data. The non-transitory computer-readable medium storing computer readable instructions, which when executed, further cause the machine to generate, by the control circuit a three-dimensional digital representation of an anatomical structure including the anatomical surface contour and the subsurface contour. The non-transitory computer-readable medium storing computer readable instructions, which when executed, further cause the machine to transmit, to a monitor, the three-dimensional digital representation of the anatomical structure.

Example 9—The non-transitory computer-readable medium storing computer readable instructions of Example 8, which when executed, further cause the machine to update, by the control circuit, the three-dimensional digital representation of the anatomical structure in real time in response to changes to the first pattern of structured light and changes to the second pattern of structured light detected by the image sensor, and transmit, to the monitor, the updated three-dimensional digital representation of the anatomical structure in real time.

Example 10—A surgical system comprising a situational awareness module configured to determine a surgical scenario based on input signals from multiple surgical devices. The surgical system further comprises a visualization system comprising a plurality of light sources, an image sensor configured to detect imaging data from the plurality of light sources, and a control circuit communicatively coupled to the situational awareness module. At least one of the plurality of light sources is configured to emit a pattern of structured light onto an anatomical structure. The control circuit is configured to receive the imaging data from the image sensor, generate a three-dimensional digital representation of the anatomical structure from the pattern of structured light detected by the imaging data, obtain metadata from the imaging data, overlay the metadata on the three-dimensional digital representation, receive updated imaging data from the image sensor, generate an updated three-dimensional digital representation of the anatomical structure based on the updated imaging data, and in response to a surgical scenario determined by the situational awareness module, update the overlaid metadata on the updated three-dimensional digital representation of the anatomical structure.

Example 11—The surgical system of Example 10, wherein the plurality of light sources comprises a plurality of coherent light sources.

Example 12—The surgical system of Example 11, wherein the metadata comprises phase shift data for the plurality of coherent light sources.

Example 13—The surgical system of Example 11 or 12, wherein the plurality of coherent light sources are configured to emit the pattern of structured light.

Example 14—The surgical system of Example 13, wherein the pattern of structured light is emitted from the coherent light sources at a plurality of different wavelengths having different tissue penetration depths.

Example 15—The surgical system of Example 14, wherein the image sensor is configured to capture the pattern of structured light at the different tissue penetration depths, and wherein the three-dimensional digital representation is generated from a surface pattern of structured light and a sub-surface pattern of structured light.

Example 16—The surgical system of Example 10, 11, 12, 13, 14, or 15, wherein the overlaid metadata is indicative of a tissue irregularity.

Example 17—The surgical system of Example 16, wherein the tissue irregularity comprises a sub-surface irregularity.

Example 18—The surgical system of Example 10, 11, 12, 13, 14, 15, 16, or 17, wherein the overlaid metadata is indicative of tissue compression along a staple line.

Example 19—The surgical system of Example 10, 11, 12, 13, 14, 15, 16, 17, or 18, wherein the overlaid metadata is indicative of a margin around an embedded structure.

Example 20—The surgical system of Example 10, 11, 12, 13, 14, 15, 16, 17, 18, or 19, wherein the overlaid metadata comprises at least one of tissue velocity, tissue distortion, tissue irregularity, tissue vascularization, and identification of an embedded structure within the anatomical structure.

Example 21—A control system for a surgical instrument comprising a user control. The control system comprises an imaging system and a control circuit. The imaging system comprises an emitter configured to emit electromagnetic radiation (EMR) and an image sensor configured to receive the EMR reflected from a surgical site. The control circuit is operably in signal communication with the imaging system and the surgical instrument. The control circuit is configured to generate an image of the surgical site based on the EMR received by the image sensor, define a first coordinate system with respect to the surgical site according to the image, receive a second coordinate system defined by the surgical instrument, determine a transfer function to translate a coordinate in the second coordinate system to the first coordinate system, and provide the transfer function to the surgical instrument to cause the surgical instrument to adjust the user control according to the transfer function.

Example 22—The control system of Example 21, further comprising a surgical hub, the surgical hub comprising the control circuit.

Example 23—The control system of Example 22, wherein the surgical hub comprises a situational awareness module configured to provide the transfer function to the surgical instrument according to a surgical context determined by the situational awareness module.

Example 24—The control system of Example 21, 22, or 23, wherein the transfer function is configured to cause the surgical instrument to adjust at least one articulation control actuator of the surgical instrument.

Example 25—The control system of Example 21, 22, 23, or 24, wherein the transfer function is configured to cause the surgical instrument to adjust a graphical user interface of the surgical instrument.

Example 26—A control system comprising an imaging system, a display screen, and a control circuit. The imaging system comprises an emitter configured to emit structured electromagnetic radiation (EMR) and an image sensor configured to receive the structured EMR reflected from a surgical site. The control circuit is communicatively coupled to the imaging system and the display screen. The control circuit is configured to generate a first image of the surgical site based on the structured EMR received by the image sensor, receive a second image of the surgical site, align the first image and the second image, generate a three-dimensional representation of the surgical site based on the first image and the second image as aligned, display the three-dimensional representation on the display screen, receive a user selection to manipulate the three-dimensional representation, and update the three-dimensional representation as displayed on the displayed screen from a first state to a second state according to the user selection.

Example 27—The control system of Example 26, wherein the update to the three-dimensional representation comprises at least one of a magnification or a rotation thereof relative to the first image.

Example 28—The control system of Example 26 or 27, wherein the control circuit is further configured to isolate an irregularity from at least one of the first image or the second image based on the other of the first image or the second image, and wherein the three-dimensional representation generated from the first image and the second image lacks the irregularity.

Example 29—The control system of Example 28, wherein the irregularity comprises at least one of a tissue, a biological structure, or an object.

Example 30—The control system of Example 26, 27, 28, or 29, wherein the control circuit is further configured to generate a third image of the surgical site based on the structured EMR received by the image sensor and update the three-dimensional representation based on the third image.

Example 31—The control system of Example 26, 27, 28, 29, or 30, wherein the second image is received from a non-real-time image source.

Example 32—The control system of Example 31, wherein the non-real-time image source comprises at least one of a CT scan or an MRI.

Example 33—A control system comprising an imaging system, a display screen, and a control circuit. The imaging system comprises a first image sensor comprising a first field of view of a surgical site and a second image sensor comprising a second field of view of the surgical site. The first field of view and the second field of view at least partially overlap. The control circuit is operably in signal communication with the imaging system and the display screen. The control circuit is configured to generate a first image of the surgical site based on the first image sensor, generate a second image of the surgical site based on the second image sensor, align the first image and the second image according to overlapping portions thereof, generate a three-dimensional representation of a structure based on the first image and the second image as aligned, cause the display screen to display the three-dimensional representation, and cause the display screen to adjust a displayed portion of the three-dimensional representation according to a user selection.

Example 34—The control system of Example 33, wherein the control circuit is further configured to receive a third image of the surgical site and update the three-dimensional representation of the structure based on the third image.

Example 35—The control system of Example 34, wherein the third image comprises tissue metadata detected by one of the first image sensor or the second image sensor.

Example 36—The control system of Example 34 or 35, wherein the third image is received from a non-real-time image source.

Example 37—The control system of Example 36, wherein the non-real-time image source comprises at least one of a CT scan or an MRI.

Example 38—The control system of Example 33, 34, 35, 36, or 37, wherein the control circuit is further configured to determined an accuracy of the first image based on a comparison to the second image and cause the display screen to convey the accuracy of the first image in the three-dimensional representation.

Example 39—The control system of Example 33, 34, 35, 36, 37, or 38, wherein the control circuit is further configured to remove an irregularity in the first image, replace the irregularity in the first image with an interpolation of a corresponding portion of the second image to generate an updated first image, and cause the display screen to display the updated first image.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical virtualization system comprising:
   an imaging device comprising:
      a first light source configured to emit light in first spectral wavelengths in a first structured light pattern;
      a second light source configured to emit light in second spectral wavelengths in a second structured light pattern; and
      a light sensor configured to detect the first structured light pattern and the second structure light pattern of an anatomical structure;
   a user interface comprising:
      a user input device; and
      an output display; and
   a control circuit comprising one or more processors coupled to at least one memory unit; wherein the control circuit is communicably coupled to the imaging device and the user interface, and wherein the control circuit is configured to:
      receive, from the imaging device, a first signal corresponding to an anatomical structure, and a second signal corresponding to the anatomical structure;
      identify, from the first and second signals, a critical structure within a predetermined proximity of the anatomical structure;
      generate a three-dimensional model of the anatomical structure and the critical structure;
      display the three-dimensional model on the output display; and
      augment an object within the anatomical structure and render a resultant three-dimensional model.

2. The surgical virtualization system of claim 1, wherein the object is a visual obstruction in a clinician's field of view.

3. The surgical virtualization system of claim 2, wherein the object is removed from the anatomical structure of the generated three-dimensional model, and wherein the resultant three-dimensional model image is an interpolation of an unobstructed model of the anatomical structure.

4. The surgical virtualization system of claim 2, wherein the object is rendered semi-transparent in the resultant three-dimensional model, and wherein the resultant three-dimensional model is an interpolation of the anatomical structure with the semi-transparent object.

5. The surgical virtualization system of claim 1, wherein the user interface enables a clinician to toggle between different views of the anatomical structure, and wherein the different views comprise:
different angles of the generated three-dimensional model, and different views of the resultant three-dimensional model.

6. The surgical virtualization system of claim 1, wherein the control circuit is further configured to:
identify a subject tissue for removal;
determine a first resection margin about the subject tissue;
recommend an adjusted resection margin based on the identified critical structure; and
render the three-dimensional model of the anatomical structure with the subject tissue, the critical structure, and the first resection margin or the adjusted resection margin.

7. The surgical virtualization system of claim 6, wherein a clinician can toggle a view on the output display between the first resection margin and the adjusted resection margin.

8. The surgical virtualization system of claim 6, wherein the control circuit is configured to:
receive an instruction associated with parameters of a surgical procedure; and wherein the adjusted resection margin is determined based on the instruction associated with the parameters of the surgical procedure.

9. A method for generating and augmenting a three-dimensional model of an anatomical structure comprising:
receiving, from an imaging device, a first signal corresponding to an anatomical structure, and a second signal corresponding to the anatomical structure;
identifying, from the first and second signals, a critical structure within a predetermined proximity of the anatomical structure;
generating a three-dimensional model of the anatomical structure and the critical structure;
displaying the three-dimensional model on an output display; and
augmenting an object within the anatomical structure and rendering a resultant three-dimensional model.

10. The method of claim 9, wherein the object is a visual obstruction in a clinician's field of view.

11. The method of claim 10, wherein the object is removed from the anatomical structure of the generated three-dimensional model, and wherein the resultant three-dimensional model is an interpolation of an unobstructed model of the anatomical structure.

12. The method of claim 10, wherein the object is rendered semi-transparent in the resultant three-dimensional model, and wherein the resultant three-dimensional model is an interpolation of the anatomical structure with the semi-transparent object.

13. The method of claim 9, wherein a user interface enables a clinician to toggle between different views of the anatomical structure, and wherein the different views comprise:
different angles of the generated three-dimensional model, and different views of the resultant three-dimensional model.

14. The method of claim 9, further comprising:
identifying a subject tissue for removal;
determining a first resection margin about the subject tissue;
recommending an adjusted resection margin based on the identified critical structure; and
rendering the three-dimensional model of the anatomical structure with the subject tissue, the critical structure, and the first resection margin or the adjusted resection margin.

15. The method of claim 14, wherein a clinician can toggle a view on the output display between the first resection margin and the adjusted resection margin.

16. The method of claim 14, further comprising:
receiving an instruction associated with parameters of a surgical procedure, and wherein the adjusted resection margin is determined based on the instruction associated with the parameters of the surgical procedure.

17. A non-transitory computer readable medium comprising instructions stored thereon, when executed by one or more processors, perform operations comprising:
receiving, from an imaging device, a first signal corresponding to an anatomical structure, and a second signal corresponding to the anatomical structure;
identifying, from the first and second signals, a critical structure within a predetermined proximity of the anatomical structure;
generating a three-dimensional model of the anatomical structure and the critical structure;
displaying the three-dimensional model on an output display; and
augmenting an object within the anatomical structure and rendering a resultant three-dimensional model.

18. The non-transitory computer readable medium of claim 17, wherein the object is a visual obstruction in a clinician's field of view.

19. The non-transitory computer readable medium of claim 18, wherein the object is removed from the anatomical structure of the generated three-dimensional model, and wherein the resultant three-dimensional model is an interpolation of an unobstructed model of the anatomical structure.

20. The non-transitory computer readable medium of claim 18, wherein the object is rendered semi-transparent in the resultant three-dimensional model, and wherein the resultant three-dimensional model is an interpolation of the anatomical structure with the semi-transparent object.

21. The non-transitory computer readable medium of claim 17, wherein a user interface enables a clinician to toggle between different views of the anatomical structure, and where the different views comprise:
different angles of the generated three-dimensional model, and different views of the resultant three-dimensional model.

22. The non-transitory computer readable medium of claim 17, further comprising instructions stored thereon, when executed by one or more processors, perform operations comprising:
identifying a subject tissue for removal;
determining a first resection margin about the subject tissue;
recommending an adjusted resection margin based on the identified critical structure; and
rendering the three-dimensional model of the anatomical structure with the subject tissue, the critical structure, and the first resection margin or the adjusted resection margin.

23. The non-transitory computer readable medium of claim 22, wherein a clinician can toggle a view on the output display between the first resection margin and the adjusted resection margin.

24. The non-transitory computer readable medium of claim 22, further comprising instructions stored thereon, when executed by one or more processors, perform operations comprising:

receive an instruction associated with parameters of a surgical procedure; and wherein the adjusted resection margin is determined based on the instruction associated with the parameters of the surgical procedure.

* * * * *

UNITED STATES PATENT AND TRADEMARK OFFICE
CERTIFICATE OF CORRECTION

PATENT NO. : 11,589,731 B2
APPLICATION NO. : 17/215235
DATED : February 28, 2023
INVENTOR(S) : Frederick E. Shelton, IV et al.

Page 1 of 1

It is certified that error appears in the above-identified patent and that said Letters Patent is hereby corrected as shown below:

On the Title Page

Page 1 and 2, Related U.S. Application Data item (63), Lines 1-5, replace "Continuation of application No. 16/729,737, filed on Dec. 30, 2019, and a continuation of application No. 16/729,778, filed on Dec. 30, 2019, and a continuation of application No. 16/729,744, filed on Dec. 30, 2019, now Pat. No. 11,219,501." with "Continuation in part of application No. 16/729,737, filed on Dec. 30, 2019, and a continuation in part of application No. 16/729,778, filed on Dec. 30, 2019, and a continuation in part of application No. 16/729,744, filed on Dec. 30, 2019, now Pat. No. 11,219,501."

Signed and Sealed this
Fifteenth Day of October, 2024

Katherine Kelly Vidal
*Director of the United States Patent and Trademark Office*